(12) United States Patent
Edgar et al.

(10) Patent No.: US 9,247,802 B2
(45) Date of Patent: Feb. 2, 2016

(54) SYSTEM AND METHOD FOR MEDICAL MONITORING AND TREATMENT THROUGH COSMETIC MONITORING AND TREATMENT

(75) Inventors: Albert D. Edgar, Austin, TX (US);
David C. Iglehart, Austin, TX (US);
Rick B. Yeager, Austin, TX (US)

(73) Assignee: TCMS Transparent Beauty LLC, Austin, TX (US)

(*) Notice: Subject to any disclaimer, the term of this patent is extended or adjusted under 35 U.S.C. 154(b) by 1043 days.

(21) Appl. No.: 11/503,629

(22) Filed: Aug. 14, 2006

(65) Prior Publication Data
US 2007/0049832 A1 Mar. 1, 2007

Related U.S. Application Data

(60) Provisional application No. 60/708,118, filed on Aug. 12, 2005.

(51) Int. Cl.
*G06K 9/00* (2006.01)
*A45D 44/00* (2006.01)
(Continued)

(52) U.S. Cl.
CPC .............. *A45D 44/005* (2013.01); *A45D 40/30* (2013.01); *A61B 5/0064* (2013.01); *A61B 5/442* (2013.01);
(Continued)

(58) Field of Classification Search
CPC .............. A61B 18/203; A61B 19/5202; A61B 19/5212; A61B 2018/00452; A61B 2018/202; A61B 5/0059; A61B 5/6888; A61B 5/442; G01N 21/4795
USPC .......................................... 600/407, 473–479
See application file for complete search history.

(56) References Cited

U.S. PATENT DOCUMENTS 4,190,056 A 2/1980 Tapper et al.
4,401,122 A 8/1983 Clark
(Continued)

FOREIGN PATENT DOCUMENTS

CN 101287607 B 9/2010
DE 202004003148 U1 4/2005
(Continued)

OTHER PUBLICATIONS

"Lehrstuhl für Optik 2004 Annual Report" Jun. 2005 (2005-2006), Lehrstuhl Für Optik, Institute Für Optik, Information und Photonik, Max-Planck-Forschungsgruppe, Universität Erlangen-Nürnberg, Erlangen, Germany, XP002460048, 2 pages.
(Continued)

*Primary Examiner* — Elmer Chao
(74) *Attorney, Agent, or Firm* — Fish & Richardson P.C.

(57) ABSTRACT

A system and method that scans areas of a human body to identify unattractive characteristics and make cosmetic enhancements is modified for medical monitoring and optionally for treatment. A 3-D model of the exterior surface of the human body is created, and the scanned data is analyzed by characteristics of reflectance and surface topology to identify unhealthy characteristics. Because people will use a cosmetics system widely and frequently, base lines of patients' conditions can be created through frequent monitoring over a long time period, so that potentially dangerous changes from the base line can identified quickly and reported on. When appropriate, precise applications of medications to treat affected areas may be made automatically. Controlled and precisely directed dosages of medications may be applied to reduce the risk of undesirable side effects. Medicines may also be applied over a large area of skin and during a long period of time to achieve desired treatments.

11 Claims, 52 Drawing Sheets

(51) Int. Cl.

| | | |
|---|---|---|
| *A61B 5/00* | (2006.01) | |
| *B41J 3/36* | (2006.01) | |
| *B41J 3/407* | (2006.01) | |
| *H04N 1/62* | (2006.01) | |
| *A45D 40/30* | (2006.01) | |
| *A61M 35/00* | (2006.01) | |

(52) U.S. Cl.
CPC .............. *A61B 5/444* (2013.01); *A61B 5/6888* (2013.01); *B41J 3/36* (2013.01); *B41J 3/407* (2013.01); *H04N 1/628* (2013.01); *A61M 35/00* (2013.01)

(56) References Cited

U.S. PATENT DOCUMENTS

| | | | |
|---|---|---|---|
| 4,628,356 | A | 12/1986 | Spillman et al. |
| 4,807,991 | A * | 2/1989 | Carew ............................ 356/72 |
| 4,882,492 | A | 11/1989 | Schlager |
| 5,027,817 | A | 7/1991 | John |
| 5,156,479 | A | 10/1992 | Iizuka |
| 5,241,468 | A | 8/1993 | Kenet |
| 5,268,166 | A | 12/1993 | Barnett et al. |
| 5,836,872 | A | 11/1998 | Kenet et al. |
| 5,931,166 | A | 8/1999 | Weber et al. |
| 6,021,344 | A | 2/2000 | Lui et al. |
| 6,067,996 | A | 5/2000 | Weber et al. |
| 6,111,653 | A | 8/2000 | Bucknell et al. |
| 6,122,042 | A | 9/2000 | Wunderman et al. |
| 6,151,031 | A | 11/2000 | Atkins et al. |
| 6,208,749 | B1 | 3/2001 | Gutkowicz et al. |
| 6,250,927 | B1 | 6/2001 | Narlo |
| 6,286,517 | B1 | 9/2001 | Weber et al. |
| 6,292,277 | B1 | 9/2001 | Kikinis |
| 6,293,284 | B1 | 9/2001 | Rigg |
| 6,295,737 | B2 | 10/2001 | Patton et al. |
| 6,312,124 | B1 | 11/2001 | Desormeaux |
| 6,341,831 | B1 | 1/2002 | Weber et al. |
| 6,436,127 | B1 * | 8/2002 | Anderson et al. ................. 607/89 |
| 6,487,440 | B2 | 11/2002 | Deckert et al. |
| 6,502,583 | B1 | 1/2003 | Utsugi |
| 6,543,893 | B2 * | 4/2003 | Desormeaux ................. 347/109 |
| 6,554,452 | B1 | 4/2003 | Bourn et al. |
| 6,575,751 | B1 | 6/2003 | Lehmann et al. |
| 6,578,276 | B2 | 6/2003 | Patton et al. |
| 6,641,578 | B2 | 11/2003 | Mukai |
| 6,706,035 | B2 | 3/2004 | Cense et al. |
| 6,719,467 | B2 | 4/2004 | Hess et al. |
| 6,810,130 | B1 | 10/2004 | Aubert |
| 7,027,619 | B2 | 4/2006 | Pavlidis |
| 7,233,693 | B2 | 6/2007 | Momma |
| 7,369,692 | B2 | 5/2008 | Shirai et al. |
| 7,382,400 | B2 | 6/2008 | Sablak |
| 7,433,102 | B2 | 10/2008 | Takahashi |
| 7,602,942 | B2 | 10/2009 | Bazakos |
| 7,890,152 | B2 | 2/2011 | Edgar et al. |
| 8,027,505 | B2 | 9/2011 | Edgar et al. |
| 8,582,830 | B2 | 11/2013 | Edgar et al. |
| 8,610,767 | B2 | 12/2013 | Uzenbajakava et al. |
| 2001/0040982 | A1 | 11/2001 | Kim et al. |
| 2002/0054714 | A1 | 5/2002 | Hawkins et al. |
| 2002/0064302 | A1 | 5/2002 | Massengill |
| 2002/0081003 | A1 | 6/2002 | Sobol |
| 2002/0105662 | A1 | 8/2002 | Patton et al. |
| 2002/0107456 | A1 | 8/2002 | Leveque |
| 2002/0128780 | A1 | 9/2002 | De Rigal et al. |
| 2002/0155069 | A1 | 10/2002 | Pruche et al. |
| 2002/0172419 | A1 | 11/2002 | Lin et al. |
| 2002/0176926 | A1 | 11/2002 | Pletcher et al. |
| 2003/0045799 | A1 | 3/2003 | Bazin et al. |
| 2003/0050561 | A1 | 3/2003 | Bazin et al. |
| 2003/0053664 | A1 | 3/2003 | Pavlidis et al. |
| 2003/0053685 | A1 | 3/2003 | Lestideau |
| 2003/0060810 | A1 | 3/2003 | Syrowicz et al. |
| 2003/0062058 | A1 | 4/2003 | Utsugi |
| 2003/0063102 | A1 | 4/2003 | Rubinstenn et al. |
| 2003/0067545 | A1 * | 4/2003 | Giron et al. ................. 348/223.1 |
| 2003/0100837 | A1 | 5/2003 | Lys et al. |
| 2003/0108228 | A1 | 6/2003 | Garnier |
| 2003/0130575 | A1 | 7/2003 | Desai |
| 2003/0208190 | A1 | 11/2003 | Roberts et al. |
| 2003/0223622 | A1 | 12/2003 | Simon et al. |
| 2003/0229514 | A2 | 12/2003 | Brown |
| 2004/0005086 | A1 | 1/2004 | Wolff et al. |
| 2004/0078278 | A1 | 4/2004 | Dauga et al. |
| 2004/0125996 | A1 | 7/2004 | Eddowes et al. |
| 2004/0170337 | A1 | 9/2004 | Simon et al. |
| 2004/0174525 | A1 | 9/2004 | Mullani |
| 2004/0179101 | A1 | 9/2004 | Bodnar et al. |
| 2004/0201694 | A1 | 10/2004 | Gartstein et al. |
| 2004/0236229 | A1 * | 11/2004 | Freeman et al. ............... 600/474 |
| 2004/0254546 | A1 | 12/2004 | Lefebvre |
| 2004/0257439 | A1 | 12/2004 | Shirai et al. |
| 2004/0267189 | A1 | 12/2004 | Mavor et al. |
| 2005/0004475 | A1 | 1/2005 | Giron |
| 2005/0010102 | A1 * | 1/2005 | Marchesini et al. ........... 600/408 |
| 2005/0019285 | A1 | 1/2005 | Lee et al. |
| 2005/0053628 | A1 | 3/2005 | Montanari et al. |
| 2005/0053637 | A1 | 3/2005 | Ma Or et al. |
| 2005/0063197 | A1 | 3/2005 | Nightingale et al. |
| 2005/0154382 | A1 * | 7/2005 | Altshuler et al. ................... 606/9 |
| 2006/0153470 | A1 | 7/2006 | Simon et al. |
| 2006/0228037 | A1 | 10/2006 | Simon et al. |
| 2006/0228038 | A1 | 10/2006 | Simon et al. |
| 2006/0228039 | A1 | 10/2006 | Simon et al. |
| 2006/0228040 | A1 | 10/2006 | Simon et al. |
| 2006/0282137 | A1 | 12/2006 | Nightingale et al. |
| 2007/0016078 | A1 | 1/2007 | Hoyt et al. |
| 2007/0035815 | A1 | 2/2007 | Edgar et al. |
| 2007/0047761 | A1 | 3/2007 | Wasilunas et al. |
| 2007/0049832 | A1 | 3/2007 | Edgar et al. |
| 2007/0203413 | A1 * | 8/2007 | Frangioni ..................... 600/478 |
| 2008/0192999 | A1 | 8/2008 | Edgar et al. |
| 2008/0193195 | A1 | 8/2008 | Edgar et al. |
| 2008/0194971 | A1 | 8/2008 | Edgar et al. |
| 2008/0219528 | A1 | 9/2008 | Edgar et al. |
| 2009/0025747 | A1 | 1/2009 | Edgar et al. |
| 2009/0209833 | A1 | 8/2009 | Waagen et al. |
| 2010/0139682 | A1 | 6/2010 | Edgar et al. |
| 2010/0224205 | A1 | 9/2010 | Mitra et al. |
| 2010/0224211 | A1 | 9/2010 | Rabe et al. |
| 2011/0124989 | A1 | 5/2011 | Edgar et al. |
| 2011/0270200 | A1 | 11/2011 | Edgar et al. |
| 2013/0149365 | A1 | 6/2013 | Rajagopal et al. |
| 2014/0050377 | A1 | 2/2014 | Edgar et al. |
| 2015/0196109 | A1 | 7/2015 | Edgar et al. |

FOREIGN PATENT DOCUMENTS

| | | |
|---|---|---|
| EP | 1 184 663 A2 | 3/2002 |
| EP | 1210909 A2 | 6/2002 |
| EP | 1304056 A2 | 4/2003 |
| EP | 1495781 A2 | 1/2005 |
| EP | 1677254 A1 | 7/2006 |
| EP | 1763380 A1 | 3/2007 |
| FR | 2810761 A1 | 12/2001 |
| JP | 59171280 U | 9/1984 |
| JP | 5281041 A | 10/1993 |
| JP | 6201468 A | 7/1994 |
| JP | 11019050 A | 1/1999 |
| JP | 11019051 A | 1/1999 |
| JP | 2000139846 A | 5/2000 |
| JP | 2000331167 A | 11/2000 |
| JP | 2001112722 A | 4/2001 |
| JP | 2002017689 A | 1/2002 |
| JP | 2002263084 A | 9/2002 |
| JP | 2003052642 A | 2/2003 |
| JP | 2003057169 A | 2/2003 |
| JP | 2003057170 A | 2/2003 |
| JP | 2003513735 | 4/2003 |
| JP | 2003519019 A | 6/2003 |
| JP | 2003210248 A | 7/2003 |
| JP | 2004105748 A | 4/2004 |
| JP | 2004315426 A | 11/2004 |

(56) References Cited

FOREIGN PATENT DOCUMENTS

| | | | |
|---|---|---|---|
| JP | 2006271654 A | 10/2006 | |
| JP | 2007231883 A | 9/2007 | |
| JP | 2008526241 A | 7/2008 | |
| JP | 2008526284 A | 7/2008 | |
| JP | 2004501707 A5 | 8/2008 | |
| RU | 2336866 C2 | 10/2008 | |
| WO | WO0126735 A1 | 4/2001 | |
| WO | WO0149360 A1 | 7/2001 | |
| WO | WO0177976 A2 | 10/2001 | |
| WO | WO2004028420 A1 | 4/2004 | |
| WO | WO2004091590 A1 | 10/2004 | |
| WO | 2004/095372 | 11/2004 | |
| WO | WO2005123172 A1 | 12/2005 | |
| WO | WO2006008414 A1 | 1/2006 | |
| WO | WO2006074881 A1 | 7/2006 | |
| WO | WO2007022095 A1 | 2/2007 | |

OTHER PUBLICATIONS

EPO Office Action in Application No. 06 801 295.4, mailed Feb. 3, 2010, 3 pages.

EPO Office Action in Application No. 06 801 295.4, mailed Jun. 10, 2008, 3 pages.

International Preliminary Report on Patentability (1 page) and Written Opinion of the International Searching Authority (8 pages) for International Application No. PCT/US2006/031441, mailed Aug. 12, 2005.

International Search Report for International Application No. PCT/US2006/031441, mailed Dec. 7, 2007, 2 pages.

Russian Official Action (including translation) in Application No. 2008109234, mailed Apr. 2, 2009, 7 pages.

Notification of the First Office Action (including translation) in Application No. 200680037564.6, mailed Jul. 31, 2009, 7 pages.

Examiner's First Report in Application No. 2006279800, mailed Feb. 2, 2011, 2 pages.

Authorized Officer Lars-Oliver Romich, International Search Report and the Written Opinion for International Application No. PCT/US2006/031441, mailed Dec. 7, 2007, 14 pages.

Russian Deputy Chief S.V. Artamonov, Decision on Grant Patent for Invention (including translation) in Application 2008109235, dated Feb. 19, 2009.

Authorized Officer Dorothee Mulhausen, International Preliminary Report on Patentability for International Application No. PCT/US2006/031657, mailed Feb. 12, 2008, 7 pages.

Authorized Officer Laure Acquaviva, Invitation to Pay Additional Fees and, where applicable, Protest Fees International Application No. PCT/US2008/053527, mailed Jul. 7, 2008, 8 pages.

Examiner's First Report in Application No. 2006279652, mailed Jan. 28, 2011, 2 pages.

Notification of the First Office Action (including translation) in Application No. 200680037560.8, mailed Jul. 17, 2009, 8 pages.

EPO Office Action in Application No. 06 789 746.2, mailed Apr. 3, 2009, 3 pages.

Authorized Officer Wolfhard Wehr, International Search Report for International Application No. PCT/US2006/031657, mailed Dec. 20, 2006, 2 pages.

Authorized Officer Athina Nickitas-Etienne, International Preliminary Report on Patentability for International Application No. PCT/US2008/053640, mailed Aug. 19, 2009, 5 pages.

Authorized Officer Michael Eberwein, International Search Report and Written Opinion for International Application No. PCT/US2008/053640, mailed Jun. 3, 2008, 9 pages.

European Patent Office Action for Application No. 08 729 481.5, dated Aug. 23, 2010, 5 pages.

Authorized Officer Jens Clevorn, International Search Report for Application No. PCT/US2008/053528, dated Nov. 13, 2008, 4 pages.

Authorized Officer Jens Clevorn, International Preliminary Report on Patentability and Written Opinion of the International Searching Authority for Application No. PCT/US2008/053528, dated Aug. 11, 2009, 9 pages.

Notification of First Office Action for Application No. 200880009579.0, dated Jul. 14, 2010, 10 pages.

Authorized Officer Simin Baharlou, International Preliminary Report on Patentability and Written Opinion of the International Searching Authority for Application No. PCT/US2008/065168, mailed Dec. 1, 2009, 8 pages.

Anonymous, "Circular Polarizer Films," Internet Article, [Online] 2005, http://www.optigrafix.com/circular.htm [retrieved on Sep. 5, 2008].

Authorized Officer Carlos Nicolas, International Search Report and Written Opinion for Application No. PCT/US2008/065168, mailed Sep. 19, 2008, 13 pages.

Mike Topping et al., "The Development of Handy 1, A Robotic System to Assist the Severely Disabled," ICORR '99, Sixth International Conference of Rehabilitation Robotics, Stanford, CA, Jul. 1-2, 1999, pp. 244-249.

Notification of the First Office Action (including translation) in Application No. 200880009069.3, mailed Jul. 1, 2011, 8 pages.

Mike Topping, "An Overview of the Development of Handy 1, a Rehabilitation Robot to Assist the Severely Disabled" Journal of Intelligent and Robotic Systems, vol. 34, No. 3, 2002, pp. 253-263.

Notice of Reasons for Rejection for Application No. 2008-526241, dated Aug. 31, 2011, 7 pages.

Robot News, "Handy1-Rehabilitation robot for the severely disabled; helping you to eat and drink and brush and even do make-up!", posted on Apr. 3, 2006, http://robotnews.wordpress.com/2006/04/03/handy1-rehabiliation-robot-for-the-severely-disabledhelping-you-to-eat-and-drink-and-brush-and-even-do-make-up/, 6 pages.

Second Examiner's Report in Application No. 2006279652, mailed Nov. 3, 2011, 2 pages.

Railan et al; Laser Treatment of Acne, Psoriasis, Leukoderma and Scars; Seminars in Cutaneous Medicine and Surgery; Dec. 2008; 285-291.

Chiu et al; Fractionated Photothermolysis: The Fraxel 1550-nm Glass Fiber Laser Treatment; Facial Plastic Surgery Clinics of North America (2007), vol. 15, Issue 2; May 2007, 229-237.

Cula et al; Bidirectional Imaging and Modeling of Skin Texture; IEEE Engineering of Medicine and Biology Society; Nov. 2004; 1-6.

Laubach et al; Effects of Skin Temperature on Lesion Size in Fractional Photothermolysis; Lasers in Surgery and Medicine; Jan. 2007; 14-18.

Bon et al; Quantitative and Kinetic Evolution of Wound Healing through Image Analysis; 2000 IEEE Transactions on Medical Imaging, vol. 19, No. 7; Jul. 2000; 767-772.

Examiner's First Report in Application No. 2008260040, mailed Apr. 13, 2012, 2 pages.

EPO Office Action in App. No. 06 801 295.4, mailed Oct. 10, 2011, 5 pages.

Cula O G et al., "Bidirectional Imaging and Modeling of Skin Texture," IEEE Transactions on Biomedical Engineering, IEEE Service Center, Piscataway, NJ, USA, vol. 51, No. 12, Dec. 1, 2004, pp. 2148-2159.

Notice to File a Response in Application No. 10-2008-7006079, dated Aug. 6, 2012, 10 pages.

Notice of Reasons for Rejection for Application No. 2008-526284, dated Apr. 18, 2012, 10 pages.

Notification of the Second Office Action for Application No. 200880009579.0, dated Mar. 1, 2012, 4 pages.

Office Action for Application No. 2009148819, mailed May 30, 2012, 7 pages.

Examination Report for European Application No. 08769826.2, dated Jul. 16, 2013, 6 pages.

Notice to File a Response in Application No. 10-2008-7006079, dated Jun. 25, 2013, 5 pages.

Notification of the Third Office Action for Application No. 200880009579.0, dated Jan. 7, 2013, 8 pages.

Notice to File a Response in Application No. 10-2008-7006041, dated Jan. 29, 2013, 10 pages.

Chujit Jeamsinkul, "MasqueArray Automatic Makeup Selector/Applicator", Nov. 11, 1998, Rochester Institute of Technology, 79 pages.

Office Action for Japanese Patent Application No. 2009-549296, Apr. 30, 2013, 12 pages.

(56) References Cited

OTHER PUBLICATIONS

Office Action for Korean Patent Application No. 10-2009-7019063, Mar. 24, 2014, 8 pages.

Examiner Saadia Khan, Examination Report for Canadian Patent Application No. 2,618,706, Jul. 31, 2014, 3 pages.

Weyrich et al., "Analysis of Human Faces using a Measurement-Based Skin Reflectance Model," Association for Computing Machinery, Inc. 2006, pp. 1-12 (1013-1024).

Donner et al., "A Layered, Heterogeneous Reflectance Model for Acquiring and Rendering Human Skin" ACM Transactions on Graphics, vol. 27, No. 5, Article 140, Publication date: Dec. 2008 pp. 1-12.

Examiner Victoria J. Depster, Examination Report for Canadian Patent Application No. 2,618,519, Jan. 16, 2015, 2 pages.

Examiner Mani Ramachandran, Examination Report for Australian Patent Application No. 2013200395, Feb. 5, 2015, 4 pages.

\* cited by examiner

Setting up an application system 200 based on scanning an area of skin 302 to determine attributes and applying RMAs 264 to that area of skin 302 in registers responsive to or in opposition to the determined attributes.
1000

Providing an application algorithm 230.
1010

Providing the application algorithm 230 on a computing environment 100.
1020

Providing storage 250 on the computing environment.
1030

Integrating a means of scanning 220 an area of skin 302.
1040

Integrating a means of application 240 of RMAs 264.
1050

FIG. 7

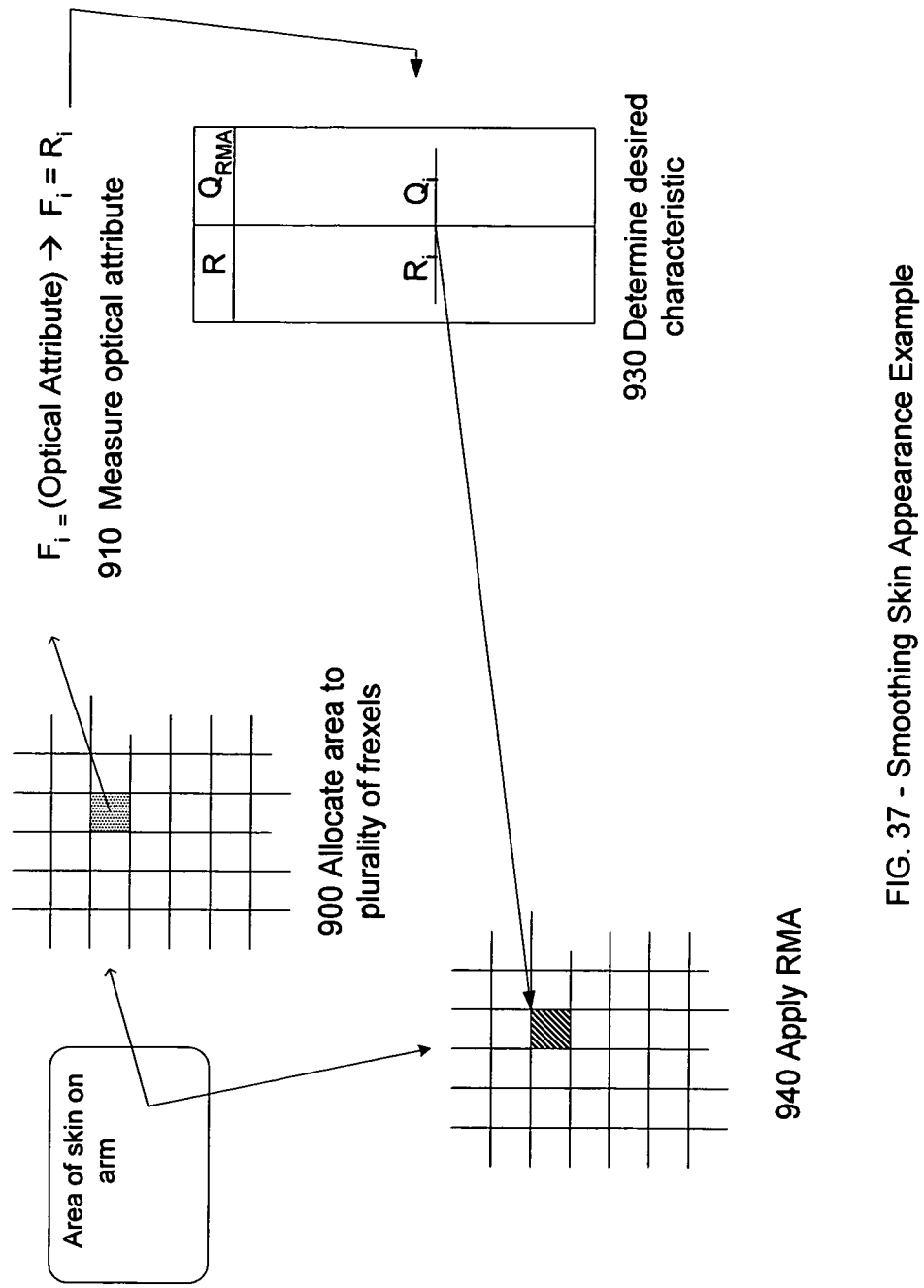
FIG. 37 - Smoothing Skin Appearance Example

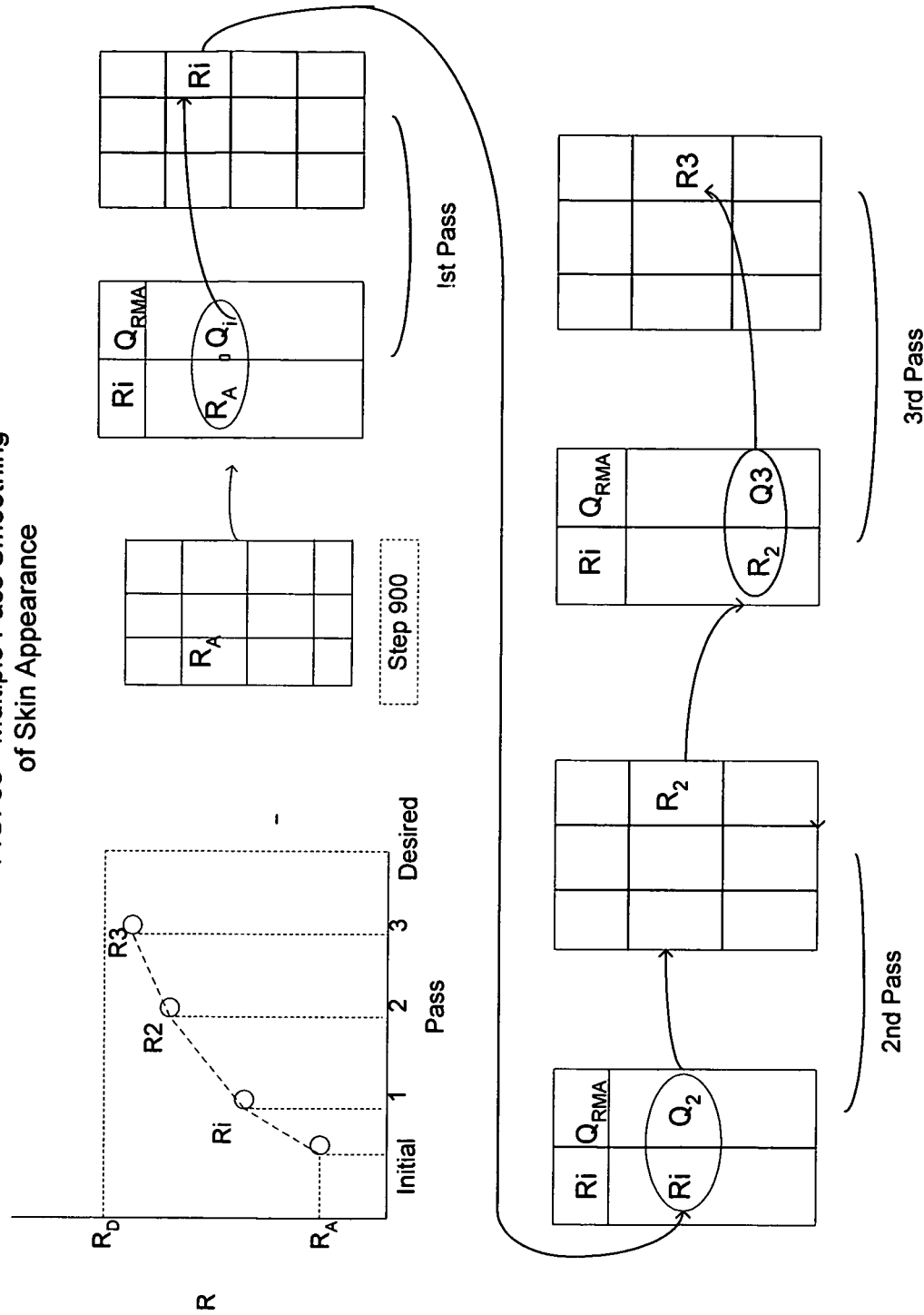
FIG. 38 - Multiple Pass Smoothing of Skin Appearance

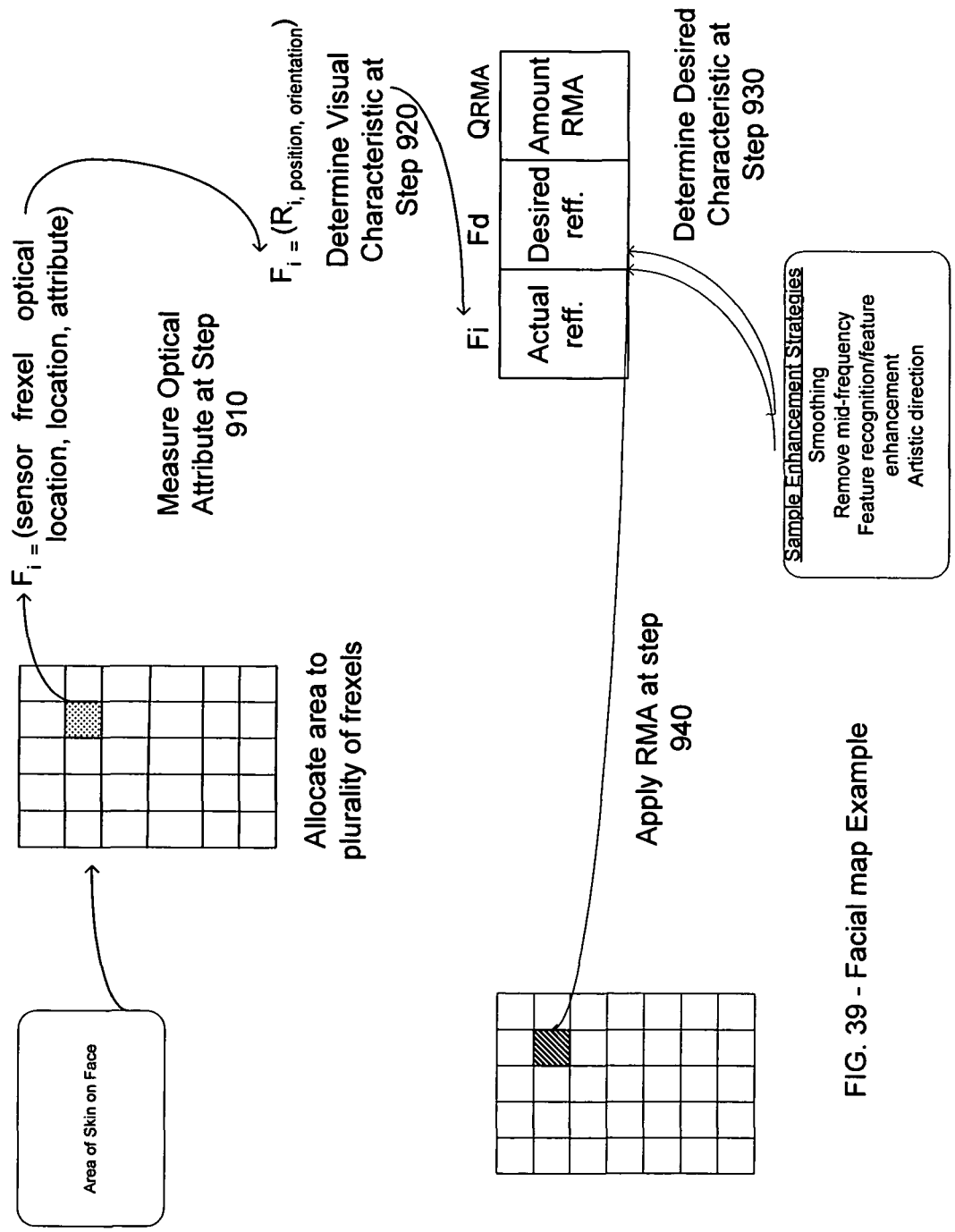
FIG. 39 - Facial map Example

FIG. 40A - Sensor and LED Arrangement
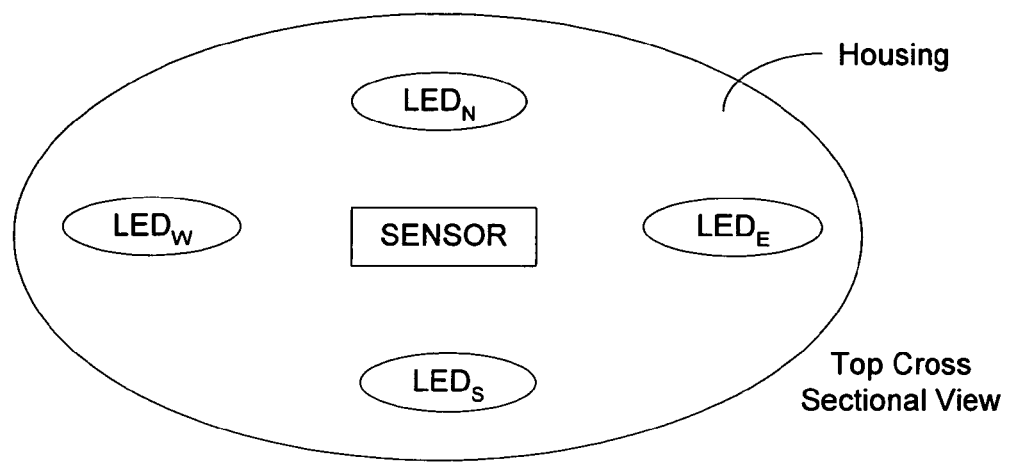
FIG. 40B
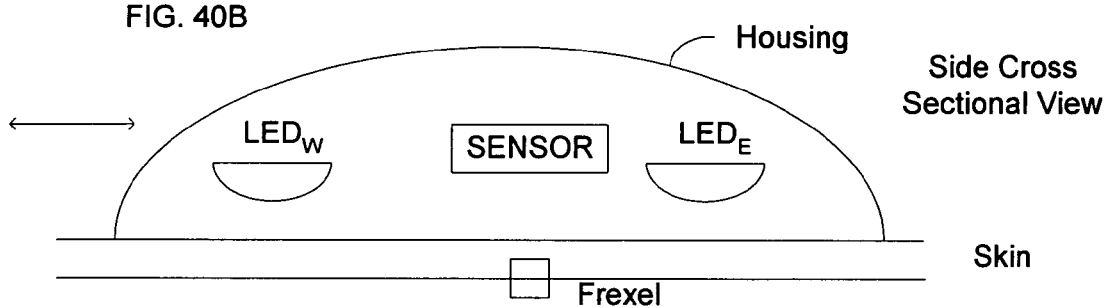

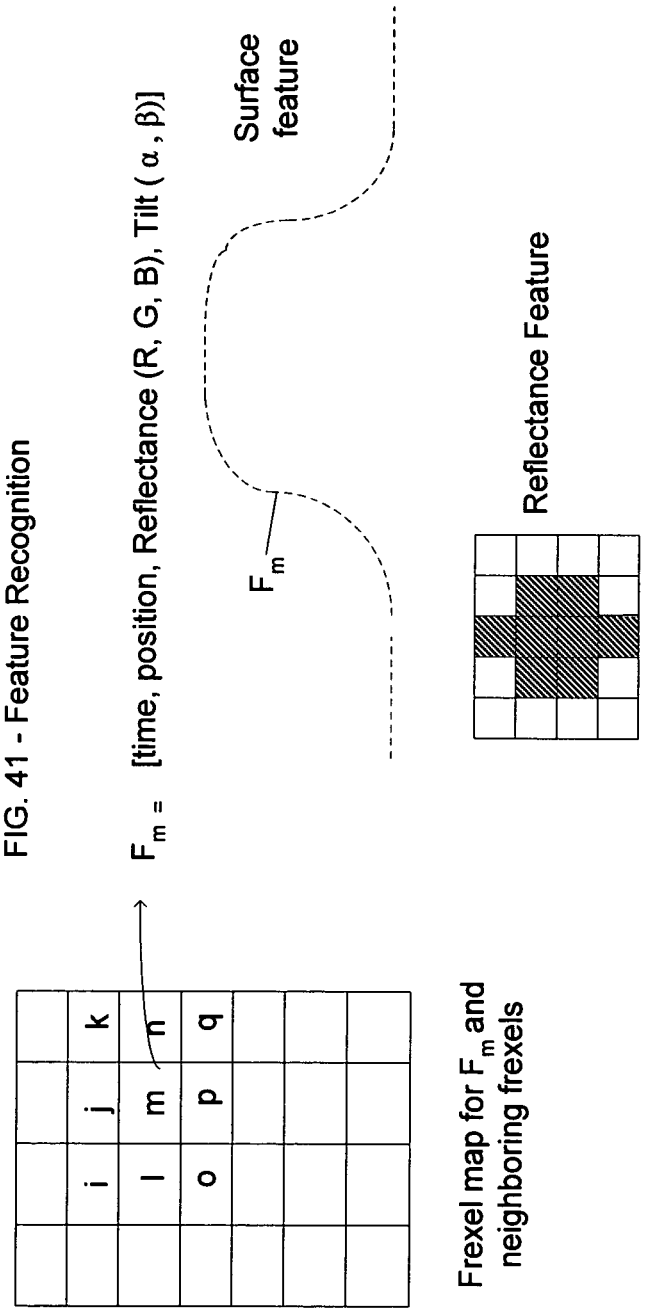
FIG. 41 - Feature Recognition
$F_m$ = [time, position, Reflectance (R, G, B), Tilt ($\alpha$, $\beta$)]
Step 910 - Scan to measure optical attribute
Step 920 - Determine visual characteristic {Reflectance, Tilt}
Step 921 - Review flexel data to identify
  - local features
  - subject range and metrics (ie. mean reflectance)
Step 924 - Apply enhancement strategies
Step 925 - Build enhancement map

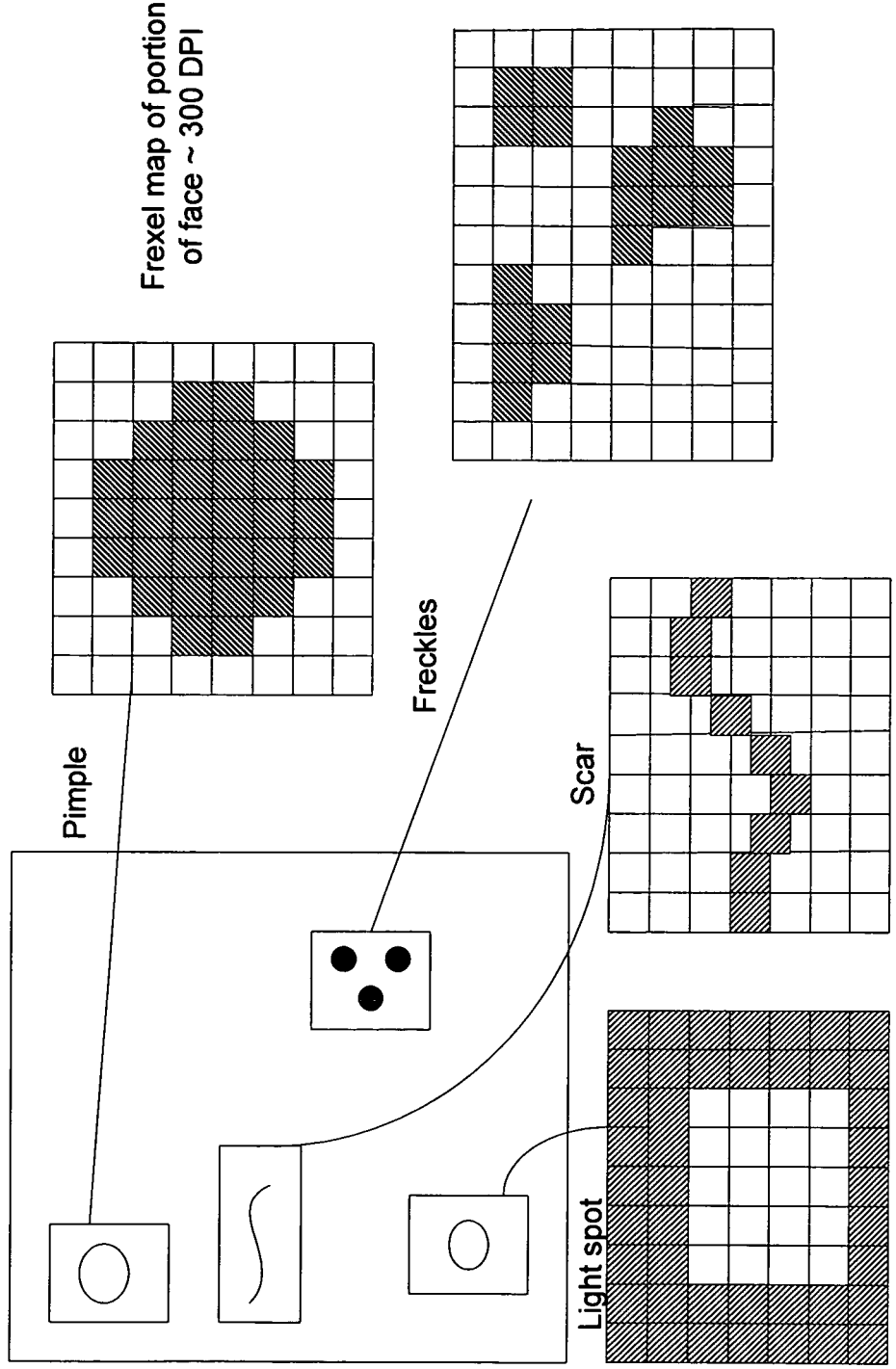
FIG. 42 - Example Feature Recognition

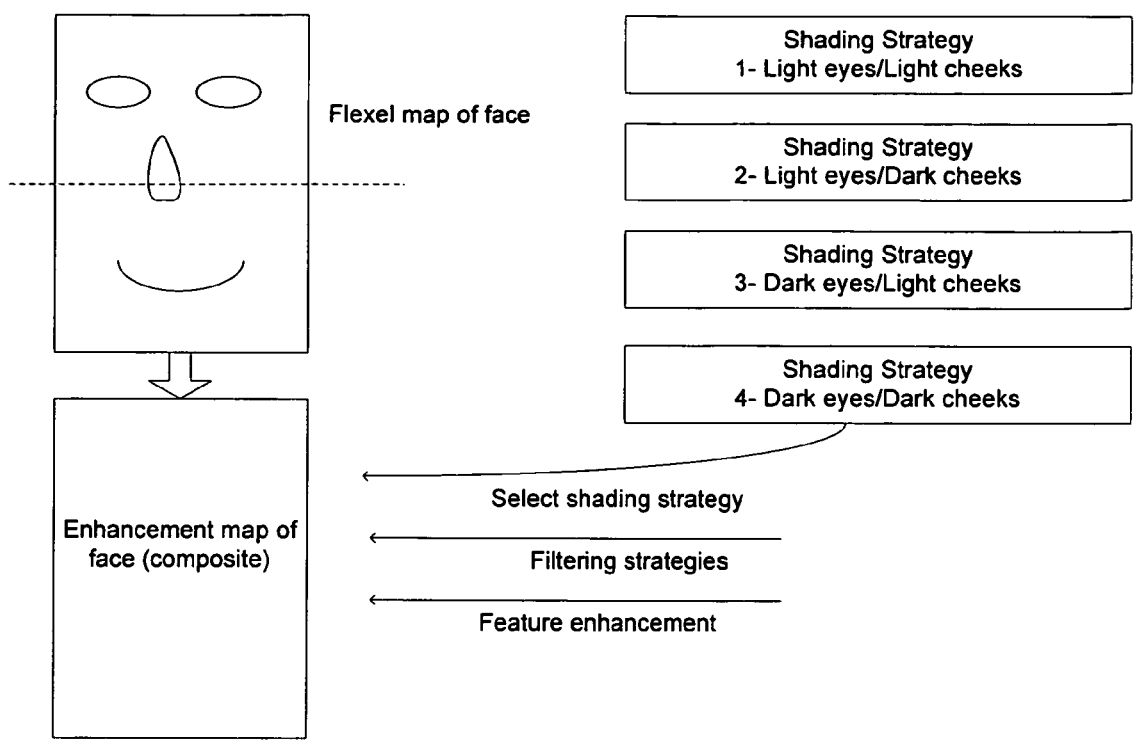
FIG. 43 - Example Artistic Strategy

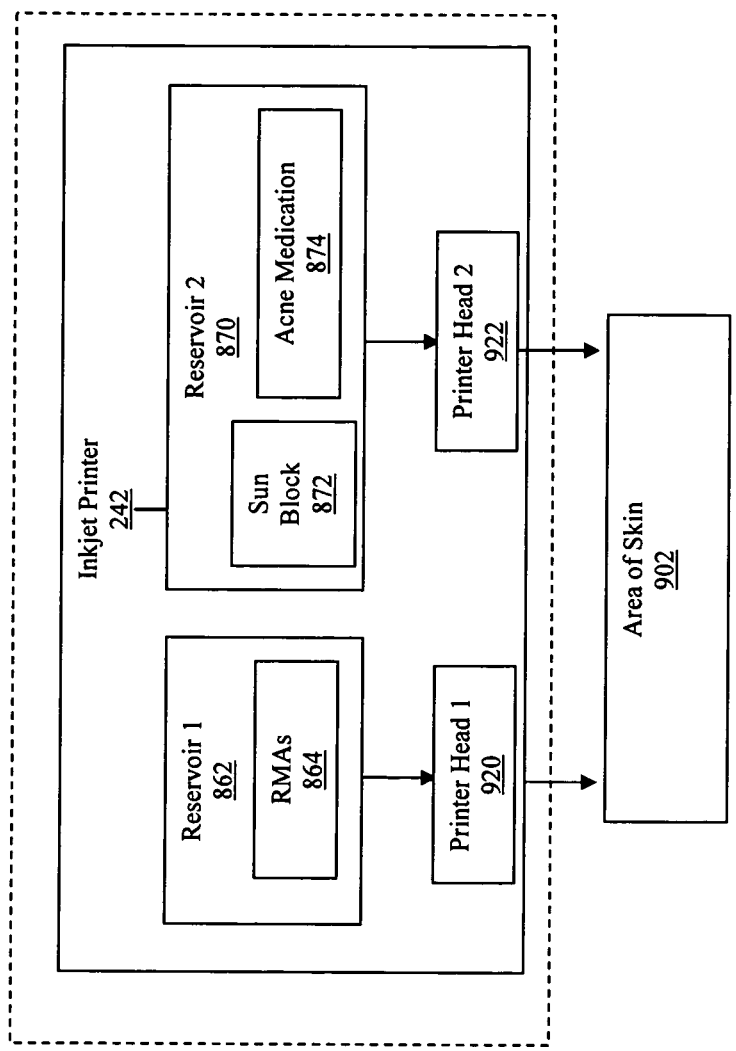

SYSTEM AND METHOD FOR MEDICAL MONITORING AND TREATMENT THROUGH COSMETIC MONITORING AND TREATMENT

CROSS-REFERENCE TO RELATED APPLICATIONS

This application claims the benefit of U.S. Provisional Application Ser. No. 60/708,118 filed Aug. 12, 2005 by applicants.

FIELD OF THE DISCLOSURE

The present invention relates to the monitoring of the human body to detect attributes that warrant preventative or curative medical attention or treatment and more particularly to an automated system and method to apply to medical monitoring and treatment of a region of skin.

BACKGROUND

Monitoring the external surface of the human body is a well established method for detecting conditions indicating illness or an increased risk of illness. For example, doctors examine patients to discover melanoma and then quickly prescribe courses of treatment for that disease. In the same way, they may discover that a patient has sun-damaged skin and prescribe that the patient avoid excessive exposure to the sun to prevent the future development of melanoma or other skin cancers. In addition, they may examine the surface topology of a woman's skin and discover a strong possibility that the woman has underlying breast cancer, so that they order further tests and appropriate treatment.

Medical examinations may be performed visually or through many kinds of medical equipment. In some cases, visual examinations may be more effective than those made by instruments, since the human eye sees both reflectance, for example color, and surface topology, for example bumps and depressions, but many mechanical instruments do not. This ability sometimes allows the eye to identify medical problems that instruments miss or cannot interpret. For example, many automated systems for medical monitoring lack the ability to analyze surface topology.

Through regular examinations, a base line of a patient's physical characteristics can be created, so that variations from that base line can be detected. One advantage of monitoring patients in this way is that early detection and treatment of illnesses and potentially dangerous conditions increases the success rates of treatments. For example, a detailed daily examination of patients' skin for signs of skin cancer could greatly increase their ability to avoid or survive skin cancer. In addition, the detection of splotches of white in people with dark skin, such as many African Americans, can indicate internal cancer. Regular examinations of skin can aid in discovering for many other illnesses and health problems, including acne, blisters, bruises, scarring, jaundice, varicose veins, and infections, and in treating them successfully.

However, the high cost of manual examinations by doctors and of examinations made with expensive medical equipment typically limits the frequency of patient monitoring. The daily monitoring of patients is typically too expensive to be conducted, except in cases where serious illnesses have already occurred and the patients have been hospitalized. General practitioners usually ask their patients to undergo general examinations only yearly, or even less frequently. Specialists also usually only see patients at widely spaced intervals, such as yearly or every six or three months. Although patients are asked to conduct self-exams more regularly, they often lack the expertise and discipline to detect medical conditions successfully. As a result, many diseases remain undetected until times when they are less susceptible to treatment.

Therefore, there is a need for an automated system and method that provides frequent medical monitoring of the external surface of the human body for characteristics of reflectance and surface topology, identifies and reports on medical problems, and, in an embodiment, treats those problems when appropriate.

In this specification, the terms "reflectance modifying agent" or "RMA" refer to any compound useful for altering the reflectance of another material, and are explained in further detail below. Some examples of RMA are inks, dyes, pigments, bleaching agents, chemically altering agents, and other substances that can alter the reflectance of human skin and other features. The terms "dye" and "transparent dyes" are used for brevity in this specification to represent any RMA.

BRIEF SUMMARY OF THE INVENTION

These and other needs are addressed by the present invention. The following explanation describes the present invention by way of example and not by way of limitation.

It is an aspect of the present invention to determine the visual attributes of an area of skin by electronically scanning the area and analyzing the scanned data in a computing environment.

In one embodiment, the scanning provides reflective data about the skin. The data is used to conduct feature identification and to monitor changes in reflectance over time.

In one embodiment, the scanning provides both reflective and surface profile data. The data is used to conduct feature identification and to monitor changes in reflectance or morphology over time.

It is another aspect of the present invention to create a map of the area of skin, and to use that map at a later time to determine the location, relative to the skin, of a monitoring device. The map may also be used to compare images from a first time and a second time in order to detect changes in reflectance or shape.

In this patent specification, the phrase "inkjet technology" refers generally to "drop control" technology, whereby each individual droplet of the substance being applied can be controlled by the applicator, as known to those skilled in the art. A particularly useful technique for the present invention is to employ "drop on demand" technology, a subset of drop control technology. In this specification, the phrase "inkjet printer" is used for brevity represent any form of inkjet technology.

It is another aspect of the present invention to precisely apply one or more medicinal agents to the skin in response to the local reflective properties of the skin.

The term "medicinal agent" is used broadly in this application to refer to any material or compound which is beneficial to a region of skin. The medicinal agent may be a pharmaceutical compound, a drug, a natural herb, a moisturizing agent, or any other material which provides a benefit to the skin.

These and other aspects, features, and advantages are achieved according to the system and method of the present invention. In accordance with the present invention, a computer-controlled system determines attributes of an area of human skin. The identified attributes may relate to reflectance and may refer to features such as irregular-looking light and dark spots, age-spots, scars, moles, and bruises, or other surface or subsurface features. Identified attributes may also relate to the surface topology of the skin, such as depth, for more precisely enhancing surface irregularities such as bumps and wrinkles. The medicinal agents can be applied in agreement with identified patterns, such as adding red to a red area, or in opposition, such adding green or blue to a red area, according to idealized models of attractiveness.

It is an aspect of the current invention to collect and analyze data at different wavelengths (color) in order to provide a basis for detailed analysis of skin features. Some skin features may be identified from the characteristics that the features exhibit in different wavelengths.

The application of medicinal agents at the pixel level allows much greater accuracy than with prior art methods, so that less of the applied material is used. In some cases, this precise delivery of medicinal agents to specific areas provides an enhanced effect of the agent without side effects associated with a systematic application of the agent. For instance, acne medication can be applied effectively to skin legions rather than taken as an oral medicine.

In one embodiment of the current invention, an application device comprising a scanner and an inkjet printer makes a single pass over an area of skin. It scans the skin, identifies problems, calculates the amount and distribution of a medicinal agent and quickly applies the agent onto the skin.

In another embodiment, the application device makes a first map of the features of the skin at a first time and identifies features of interest. It then makes a second map of the features of the skin at a second time and identifies features of interest. The two maps, and the features of interest are compared to monitor changes in the features.

In this embodiment, a detailed scan is made of a region of human skin such as a face, leg, or arm. The scan is acquired by deliberately flashing multiple light sources arranged in a known configuration, and scanning a small area of skin as the light sources are turned on and off. By comparing readings from different light sources, both the reflectance and the surface profile of the skin can be determined.

The data from the scan includes reflective characteristics of the skin. These characteristics can be used to produce a detailed map of the skin which includes both reflectance and skin surface morphology. The detailed map can be used to develop a corrective plan to selectively apply a medicinal agent.

It is an aspect of the present invention to provide an automated system and method that provides frequent medical monitoring of the external surface of the human body for characteristics of reflectance and surface topology.

It is another aspect of the present invention to provide an automated system and method that identifies medical problems in the external surface or subsurface of the human body through monitoring.

It is another aspect of the present invention to provide an automated system and method that reports of medical problems in the external surface or subsurface of the human body identified through monitoring.

It is still another aspect of the present invention to provide an automated system and method that applies medicines to identified problems in the external surface of the human body when appropriate.

These and other aspects of the present invention will become readily apparent upon further review of the following specification and associated drawings. In accordance with one embodiment of the present invention, a system and method that scans areas of a human body to identify unattractive characteristics and make cosmetic enhancements is modified for medical monitoring and optionally for treatment. A 3-D model of the exterior surface of the human body is created, and the scanned data is analyzed by characteristics of reflectance and surface topology to identify unhealthy characteristics. Because people will use a cosmetics system widely and frequently, base lines of patients' conditions can be created through frequent monitoring over a long time period, so that potentially dangerous changes from the base line can identified quickly and reported on. When appropriate, precise applications of medications to treat affected areas may be made automatically. Controlled and precisely directed dosages of medications may be applied to reduce the risk of undesirable side effects. Medicines may also be applied over a large area of skin and during a long period of time to achieve desired treatments.

BRIEF DESCRIPTION OF THE DRAWINGS

The following embodiment of the present invention is described by way of example only, with reference to the accompanying drawings, in which:

FIG. 7 is a flow chart that illustrates a process for setting up an application system;

FIG. 37 is a schematic for a simple skin smoothing example.

FIG. 38 is a schematic for a multiple pass smoothing example.

FIG. 39 is a schematic for a facial map example.

FIGS. 40A-B are sample layouts for LEDs and a sensors for acquiring reflectance and skin orientation data;

FIG. 41 is a schematic for feature recognition;

FIG. 42 is a schematic of an example for feature recognition;

FIG. 43 is a schematic of an artistic strategy for applying RMAs;

FIG. 52 is a block diagram showing the use of a second reservoir with medical compounds and a second inkjet printer head for medical applications of a cosmetic system.

DETAILED DESCRIPTION OF EMBODIMENT—PROVIDING A COSMETIC SYSTEM FOR APPLYING REFLECTANCE MODIFYING AGENTS, AND USING THE COSMETICS SYSTEM FOR MEDICAL MONITORING

The details of the following explanation are offered to illustrate the present invention clearly. However, it will be apparent to those skilled in the art that the concepts of present invention are not limited to these specific details. Commonly known elements are also shown in block diagrams for clarity, as examples and not as limitations of the present invention. Furthermore, the order of processes, their numbered sequences, and their labels are presented for clarity of illustration and not as limitations on the present invention.

This embodiment describes a cosmetic method to improve the visual attractiveness of a region human skin as described in copending patent applications by applicants. As described in more detail below, in one embodiment of the current invention the cosmetic system is adapted for use in medical monitoring of the skin. One advantage is that it provides a frequent monitoring of skin during the cosmetic sessions, without additional effort. In another embodiment, many of the scanning, mapping, and application techniques described for the cosmetic system are adapted for a medical monitoring device.

Figure 24:
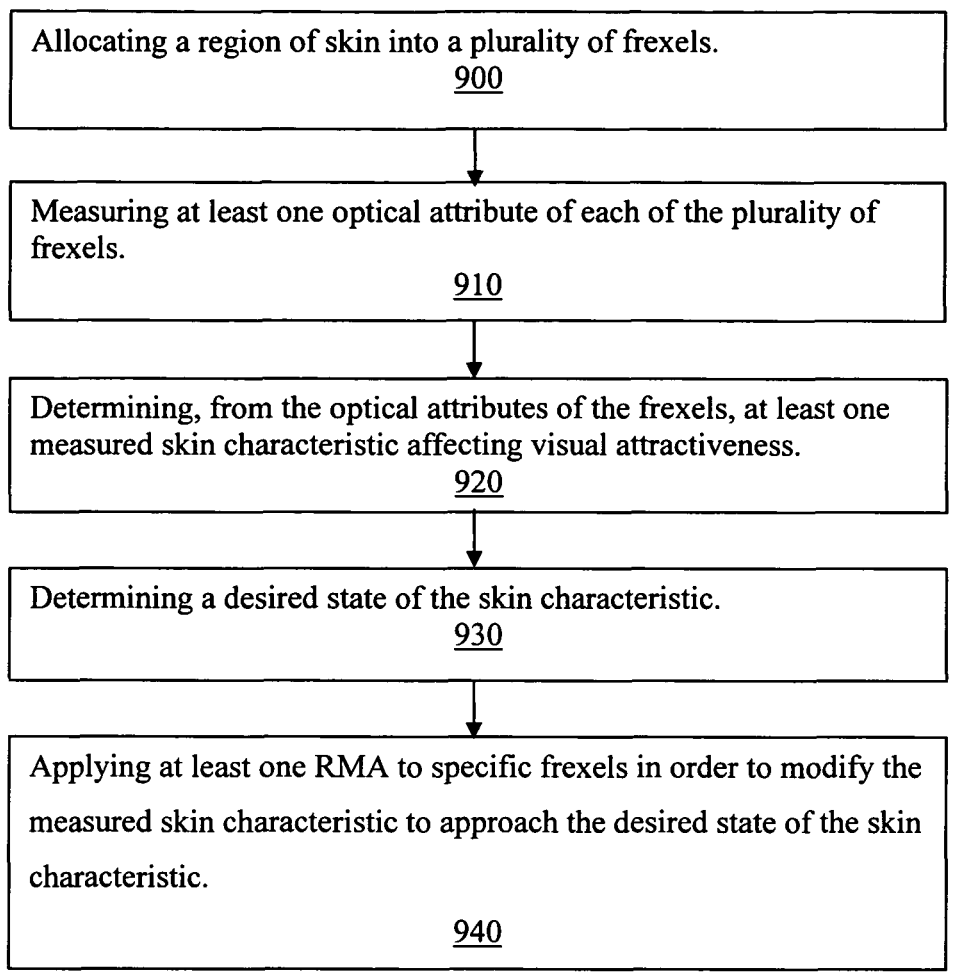
FIG. 24 is a flow chart showing the general steps employed by the present invention.

As shown in FIG. 24, the cosmetic method comprises the general steps of

Step 900—allocating a region of skin into a plurality of frexels;

Step 910—measuring at least one optical attribute of each of the plurality of frexels;

Step 920—determining, from the optical attributes of the frexels, at least one measured skin characteristic affecting visual attractiveness;

Step 930—determining a desired state of the skin characteristic; and

Step 940—applying at least one reflectance modifying agent to specific frexels in order to modify the measured skin characteristic to approach the desired state of the skin characteristic. This step may be modified to apply one or more medicinal agents in the current invention.

Allocating a Region of Skin into a Plurality of Frexels

In this patent specification, the term "frexel" is defined as a small pixel-like region of the skin. In this patent application, the term "skin" is used not only to refer to skin as on the surface of the human body, but also to refer more broadly to any human feature that may be enhanced cosmetically, for example fingernails and hair. A frexel might correspond to a small portion of a freckle or other skin feature, or it may correspond to an area of the skin that does not have special features. A frexel thus refers to skin rather than to an independent coordinate system.

The term frexel is used to suggest that what is being measured is on a 3-D surface rather than a flat surface. A region of skin is comprised of a plurality of frexels. For instance, if a resolution of 300 dots per inch (11.8 pots per mm or "dpmm") is used, a frexel may have a width and height of about 1/300th of an inch (0.085 mm) so that there are approximately 90,000 frexels per square inch (140 frexels per square mm). The surface of the human body may have millions of frexels.

By allocating skin into frexels, the present invention can accomplish scanning and the application of RMAs for enhancement at the higher end of the human visual ability to resolve detail.

Figure 23:
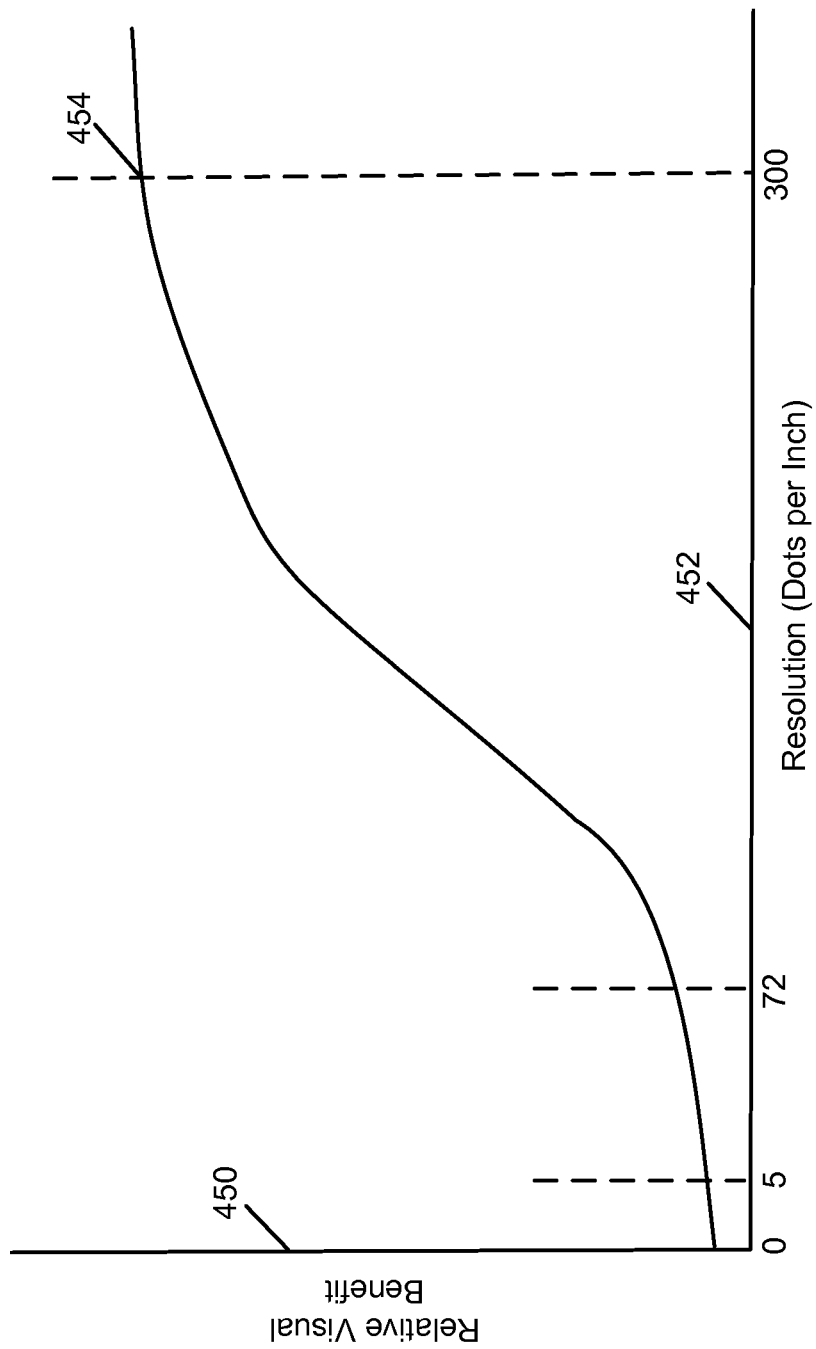
FIG. 23 is a generalized graph of visual benefits versus resolution.

FIG. 23 is a generalized graph of relative visual benefits 450 versus dots per inch (DPI) 452 resolution. A target resolution in the range of 50 to 300 dpi (2-11.8 dpmm) provides much better resolution that existing cosmetic techniques, as well as advantages in making the adjustments in response to actual and desired skin characteristics; and the further advantage of automatic application. Prior art techniques for applying makeup with brushes, tubes, and fingers have much coarser resolutions. For instance a fine brush has an approximate resolution of about 20 dpi (o.8 dpmm).

Measuring at Least One Optical Attribute of Each of the Plurality of Frexels

Scanning

Figure 1:
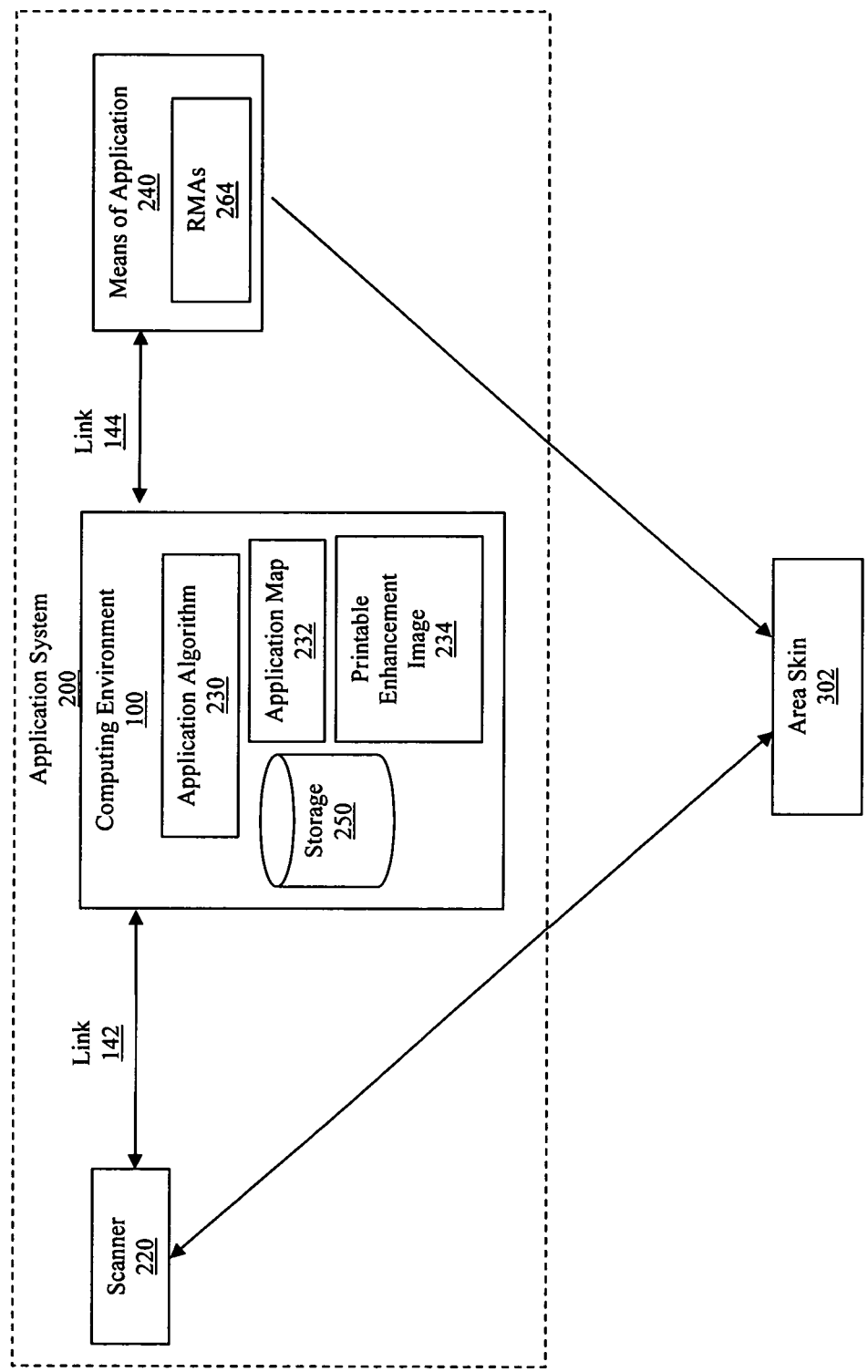
FIG. 1 is a block diagram showing an operating environment in which embodiments of the present invention may be employed for applying RMAs onto skin.

As shown in FIG. 1, in one embodiment, an application device comprising a scanner 220 is moved across the area of skin 302 so that the scanner 220 can electronically record data about one optical attribute, such as the reflectance, of each of the plurality of frexels. For example, the area of skin 302 might be a face.

The scanning may acquire images under various frequencies to obtain useful data. For example, it may obtain data on reflectance in a particular color, for example red, to help determine a particular characteristic of skin for enhancement. The scanning may also provide data for determining other characteristics of skin, such as surface topology, based on reflectance angle from multiple light sources.

In an embodiment a two-dimensional array is used for the scanning. In other embodiments, a line array may be used.

Alerting Sounds

In an embodiment one or more alerting means, such as a sound, light, or vibration may be used to indicate when sufficient scanning has been accomplished.

Sensors

In one embodiment, the scanner 220 comprises a sensor and four LED light sources arranged in a known configuration within a housing. The LED light sources are typically each turned on and off in a manner that allows the sensing of at least one optical characteristic for each light source. In one example, 120 captures may be made per second, 30 from each light, quickly providing a large about of data about the skin. That data can then be used to determine both reflectance characteristics at various wavelengths, and the skin's surface profile. In an embodiment the captured images may be averaged for effectiveness.

In an embodiment, the sensor comprises shading patterns on the LEDs useful for determining the relative position of the sensor.

In an embodiment a monochrome sensor with a Bayer array may be employed. Other arrangements of LEDs and sensors may be used.

Analyzing the Scanned Data

The scanned data comprises information about
The reflectance from the skin, and
The location of the skin relative to the sensor, and the skin features.

In an embodiment, the application algorithm 230 puts the stored data into spatial frequency bands and uses pattern recognition to analyze them to determine the landscape of the area of skin 302 and the dimensions that require application of the RMAs 264. The process used to determine these dimensions will be explained in detail below.

The application algorithm 230 uses its analysis to create in software an application map 232 of the area of skin 302, which is stored in storage 250, for potential future use.

Optical Attributes

The reflectance, which is a measure of the reflection of the skin, is independent of its illuminance. Illuminance is a measure of how much light gets to the skin. The light reading is independent of the surface topology reading.

In an embodiment, certain optical attributes, such as the amount of reflectance of each frexel, may be determined directly from the scanned data. In another embodiment, the scanned data is translated into at least one spatial frequency band for analysis. In still another embodiment, the scanned date may be translated into multiple spatial frequency bands, such as red, green, and blue (RGB) bands.

Figure 14:
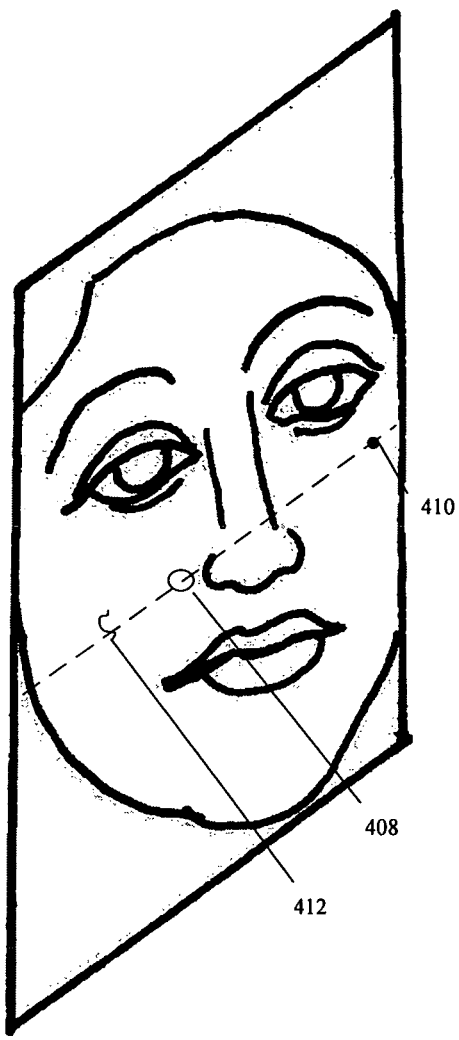
FIG. 14 is a perspective diagram that illustrates features on a 2-D map of a human face.

FIGS. 16A-E represent the patterns of a 2-D face 232, shown in FIG. 14, after the data has been put into single spatial frequency bands to determine the attributes of albedo 348 and illuminance 352.

Albedo

Albedo is the percentage of reflectivity of incident light from the surface of an object. In the case of electronic scanning, the albedo is the RBG values of the scanned area of skin. In this patent application, the term "actual albedo" means the observed albedo before correction and the term "aim albedo" refers to the desired reflectivity of an area of skin in order to improve the appearance of that area of skin. In one example, the aim albedo is determined from one or more correction strategies, including general smoothing, specific feature enhancement, and artistic strategies.

Figure 16:
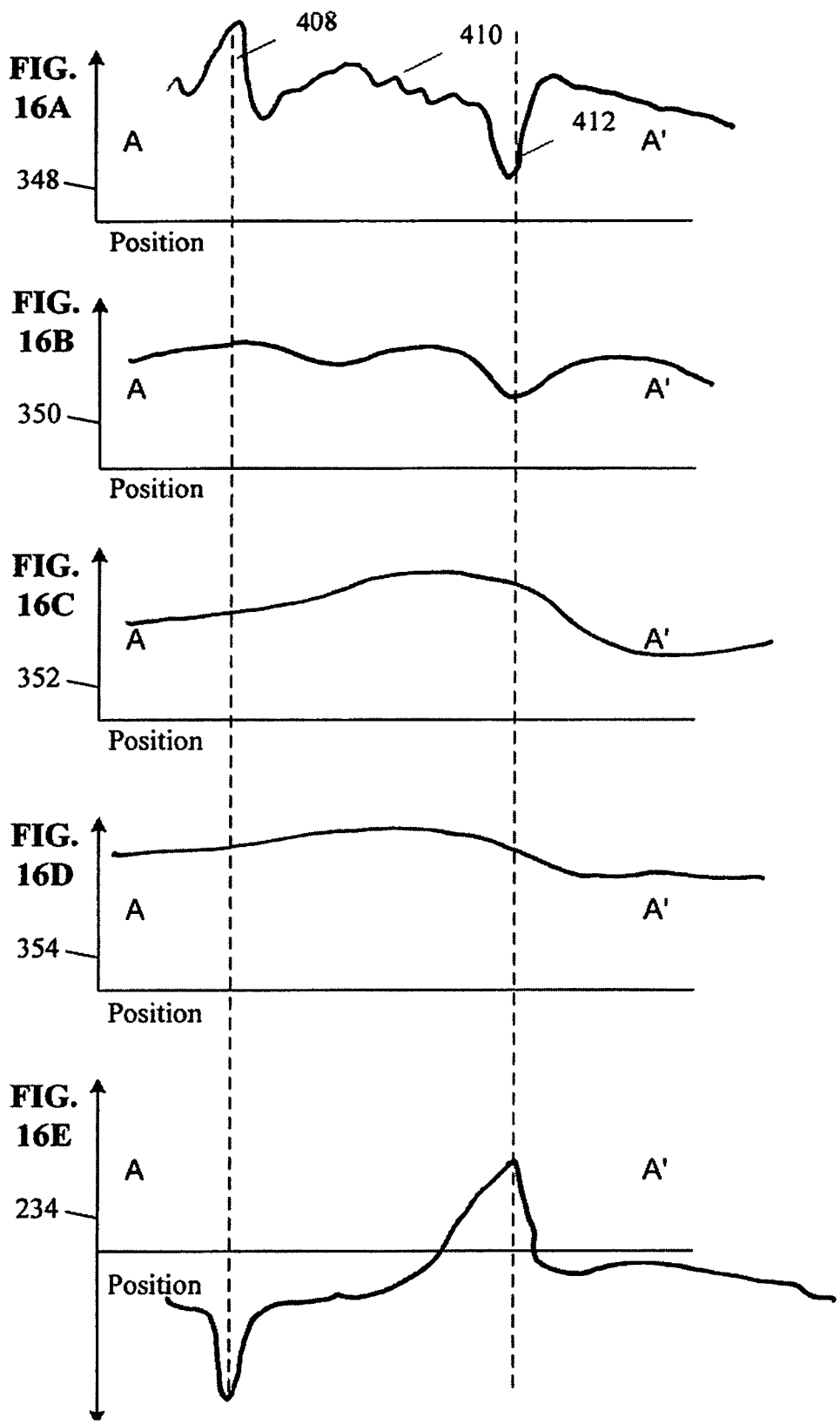
FIGS. 16A-E are charts of the reflectance, illuminance, and a printable enhancement image along line A-A' of the 2-D map of the human face of FIG. 14.

The top band in FIG. 16 represents the actual "albedo" along line A-A' in the 2-D surface map 232 of FIG. 14. A rise in the actual albedo graph identifies the light spot 408. A deep, sharp drop in the graph identifies a non-uniformity 412 such as a scar. And an irregular section identifies a freckle 410.

Illuminance

Illuminance is the incident light reaching a unit area of the surface of an object, and is a function of the angle of the incident light relative to the surface.

The spatial frequency bands also graph the actual illuminance or shading 352, shown in FIG. 16, of the 2-D surface map 232 shown in FIG. 14.

Reflectance and Illuminance Data and Calculations

In one example, frexel data obtained from scanning a region of skin may be represented as $(x_s, y_s, z_s, \alpha_s, \beta_s, \gamma_s)$, $(x_f, y_f, z_f, \alpha_f, \beta_f, \gamma_f)$, $\{(\text{refl})_A, (\text{refl})_N, (\text{refl})_S, (\text{refl})_E, (\text{refl})_W\}_i$ The term $\{(\text{refl})_A, (\text{refl})_N, (\text{refl})_S, (\text{refl})_E, (\text{refl})_W\}$ represents reflective data for the frexel i under ambient lighting conditions, and for each of four light sources, such as LEDs, which are arbitrarily designated as north-south-east-west for ease of discussion. Other numbers of light sources, such as three sources, can be used, but the mathematics is simplified with four light sources. The (refl) represents one or more data point for the reflectance measurement. The reflectance measurement for a wavelength is the product of a constant, the illuminance, and the albedo for the wavelength:

$$Reflectance = k * illuminance * albedo$$

For instance:

$$Reflectance(red) = k(red) * illuminance(red) * albedo(red)$$

The constant depends upon several factors including the speed of the lens, the sensitivity of the camera or sensor, the transmission characteristics of the color filter, the gain of the analog amplifier, the digital gain applied by the software, and other factors. The constant k will usually be measured and corrected for as a correction constant or calibration of the camera corrects for these effects. The value of the constant can typically be determined during calibration, when the illumination from the LEDs is assumed to be fixed, and the albedo is calculated based on that assumption.

Reflectance is not absolute, but is a measure of what comes out of the camera.

The sensor is typically a camera without an amplifier, a digital converter, or the lens housing. In one embodiment, the sensor is a solid state MOS sensor with a lens and associated electronic equipment.

The frexel data can be processed to determine a reflectance and an illuminance for each light source, and that information can be used to determine reflectance and surface profile.

In one example, the reflectance is the average or mean of all measurements. The illuminance can be determined from the known brightness of light sources such as LEDs. Illuminance is the known light times the cosine of the angle of incident light relative to the normal.

One problem with obtaining reflectance data is that glare may be present at some angles, and that an accurate reading cannot be obtained. In one example, glare or glossiness can be eliminated with the use of polarizing materials to provide a cross polarization of the LEDs. In other examples the sensor can deliberately be positioned at a relatively large angle such as 60 degrees in order to eliminate glare.

Determining Position

Frexel Location Relative to Sensor or Coordinate System

The term $(x_f, y_f, z_f, \alpha_f, \beta_f, \gamma_f)$ may represent the distance of the frexel i from the sensor, or may be an absolute position and orientation of the frexel with respect to a reference coordinate system. In one example, the determination of the distance from the frexel to the scanner may be made in two steps. A first step can be an approximate mechanically-based measurement such as a constant height of the sensor from the skin. The second step can be an optical first derivative measurement to provide a fine adjustment. In one example, the fine adjustment is calculated by measuring an angle from the surface. In another embodiment, a fine adjustment may be made by using two light sources to send out two reference points or grids for detection by a sensor.

Mechanical Gross Estimate

In one embodiment, the sensor may be attached to a helmet or a fixed booth in a manner that the sensor position may be determined relative to the helmet or booth.

Figure 26:
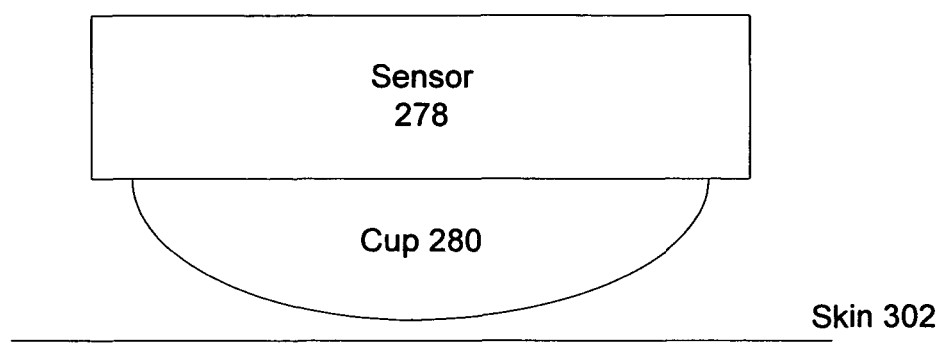
FIG. 26 is a block diagram showing a spacer cup on a sensor.

In another embodiment shown in FIG. 26, the sensor 278 may be equipped with a cup 280, so that the sensor 278 maintains an average height from the skin.

In another embodiment, the sensor may start from a known position, and keep track of its movements in order to estimate its location. The sensor may measure the angle relative to the probe itself to determine the shape of a surface feature relative to constantly changing plane of probe.

A gimbal may be used to provide a reference in space. The tracking may be used to follow the position of a hand, or hand-held scanner in space. The gimbal arrangement can provide regular feedback in a manner that is analogous to stereo-mapping or GPS mapping relative to satellites, such as for crop dusting.

Optical Fine Adjustment

For finer alignment, an optical means may be used. For example, the first derivative of the z component of the skin may be obtained from shading, through multiple light and shadings from probes. The first derivative can provide a measure of the angle of the surface.

In one example, three light sources send out different patterns. The color and the shading provide data for determining surface relief so that a shaded relief map may be obtained from the LEDs.

Frexel Orientation

By determining the tilt of the frexel relative to two orthogonal axes, the orientation of the frexel can be determined. The orientation of a frexel and its neighbors is an indication of the actual local surface texture of the skin. One aspect of the current invention is the ability to measure and compensate for both local reflective properties and local surface texture.

In this example, there are four light sources which are designated as North, South, East, and West. The sensor obtains data when each light source is on, and the other sources are off. The sensor may also obtain data for ambient lighting, with none of the four light sources on.

The tilt of the frexel can be determined by comparing the North and South measurements. The difference between these measurements is a related to the tilt of the frexel along the East-West axis. The difference between the East and West measurements is a related to the tilt of the frexel along the North-South axis.

It is generally necessary to make a gamma correction by converting the data to linear space. The gamma correction is approximated by taking the square root of the data output by typical gamma 2 cameras.

Light Sources

FIGS. 40A-B show configurations for light sources that may be used with one embodiment of the present invention. In this embodiment, a set of four light sources is used—$LED_N$, $LED_S$, $LED_E$, and $LED_W$. The light sources are placed in a diamond configuration where the sensor is positioned at the center of the LED layout. This configuration simplifies the mathematical analysis for calculating surface profile.

Mean Illumination

In one embodiment, it is useful to employ the concept of mean illumination. Mean illumination is the average angle and diffusion of light reaching a particular surface. This defines how surface irregularities are typically shaded. For example, mean illumination for the entire body is overhead, and a typical orientation for a head is vertical; therefore, a bump on a cheek is typically shaded at the bottom. For a child on the beach, typically the bump would be less tanned on the bottom because the average light throughout the day, integrating both sun angle and body angle to give average or mean illumination, is from over "head." Occasionally light is reversed from average. An example is lighting a face from underneath. However, this often gives a bizarre, sometimes sinister look, and is the exception that proves the rule. By correcting a defect for mean illumination, the best correction on average is performed.

Mean illumination is the interaction of mean light direction relative to gravity and the mean orientation of a particular frexel of skin relative to gravity. One method to obtain the angle of the skin is to use multiple diffuse or orthogonal light sources in a configuration which may include mirrors. The lights may be flashed repeated, as strobe lights, so that hundreds of images may be taken of a small area, and the data can be averaged. From the angle of the skin relative to "up," one can calculate how much light reaches the skin under mean illumination and the angle of the skin relative to "up."

A reasonable approximation to mean illumination can be made by turning on all lights sources at the same time, or by adding images made by individual light sources. In one example, mean illumination is diffuse because lights and probes are perpendicular to the skin.

A refinement of this technique will compensate for gloss effects on the skin. For example, several images with four lights sources may be used and an average taken of the images from the light sources. For example, the average might be a median. One advantage of the median is that if specular reflection is caught by a minority of light sources, it would be filtered by median. The median would also filter shadows observed from a minority of light source images. This is important because the human body represents complex surfaces, i.e. a nose may be shiny when illuminated.

One way to create diffuse light is to introduce light from many light sources at many angles. Another way to create diffuse light is to reflect it from the scanner housing. Another option is to polarize the light.

Example of Frexel Data Representation

An example of the data representation for a frexel is shown below:

$$(x_s, y_s, z_s, \alpha_s, \beta_s, \gamma_s),$$

$$(x_f, y_f, z_f, \alpha_f, \beta_f, \gamma_f),$$

$$\{(\text{refl})_A, (\text{refl})_N, (\text{refl})_S, (\text{refl})_E, (\text{refl})_W\}$$

In this example, $(x_s, y_s, z_s, \alpha_s, \beta_s, \gamma_s)$ and $(x_f, y_f, z_f, \alpha_f, \beta_f, \gamma_f)$ represent the position and angular orientation of the scanner sensor and the frexel relative to a coordinate system.

Compression

In some embodiments, the efficiency of the data processing can be improved by various compression methods, such as JPEG.

Frexel Location on the Skin

Through Feature Mapping

Computer mapping for feature recognition, known to those skilled in the art in areas such as computer gaming, can be used for tracking the location of the probe on the area of skin 302 and for determining enhancements appropriate for specific features.

For example, such computer mapping enables the identification of features such as a cheekbone, a nose, and an ear, so that the probe can orient its location with regard to a particular frexel, potentially in multiple passes over an area of skin.

Moreover, the identification of a feature such as a cheekbone enables determination of appropriate enhancements. For example, a red reflectance modifying agent may be applied to the center of a cheekbone to add color to a face. Dark reflectance modifying agents may be applied underneath the cheekbone to make the cheekbone appear to project more prominently.

Skeleton Model

In one embodiment, a map is built around a skeleton model so that the skeletal joints become reference points. In this example, the joints are located, a stick figure is constructed, and a 3-D mesh is built around the stick figure. The map is relative to a predetermined model of human skeletal structure in the memory of a computing environment.

Manikin-Like Model

In one embodiment, the map is relative to a predetermined model of a human body.

Dynamic Model

In one embodiment, the map is relative to the movement of skin over a predetermined model, such as a skeleton model or manikin-like model.

Through Chemical Markers

In other embodiments, chemical markers may be applied to the area of skin during the scan to help create the map and enable subsequent tracking of the map with the area of skin 302. For example, ultraviolet markers may be used, such as dots which are visible under ultraviolet light, but not visible under conventional lighting.

Single Pass or Multiple Pass

In various embodiments, the scanning and correction can be accomplished in a single or multiple passes. For instance, a first pass may be performed to become acquainted with the subject, and a second or subsequent pass may be performed to get additional data. Multiple passes at different orientations over the same area provide an opportunity for compensating for the effects of skin hair by observing the skin at different angles.

Single Pass

In one embodiment of the current invention, an application device comprising a scanner and an inkjet printer makes a single pass over an area of skin. It scans the skin, identifies unattractive characteristics, calculates enhancements to make the skin more attractive, and quickly applies RMAs onto the skin to achieve those enhancements.

Multiple Pass

In a further embodiment, the application device makes multiple passes over the skin, each time improving the scanning and the application of RMAs for the desired enhancement or enhancements.

Example of Tracking Process

In one example of a tracking process, a rough position is first determined, and then a more precise location is established. In a first approach, a rough estimate of location can be maintained from a known starting point through the use of gimbals in proximity to the probe to compute distance and direction traveled. In another approach, a rough location can be determined from mechanical probes or gauges. In another approach, a rough location can be estimated mathematically by using the first derivative of the shading data.

Once the rough location is known, a more precise location can be determined from the analysis of frexel orientation from shading data. This is analogous to a pilot determining position by first knowing an approximate location and then locating land features that provide a more precise location.

Tracking Over Time

One advantage to the generation of maps is that changes in reflectance or surface profile can be determined by comparing an image from a first time with an image from a second time. These changes may represent changes in the health of a person, or may represent areas that require a "touch-up" of RMAs.

Determining, from the Optical Attributes of the Frexels, at Least One Measured Skin Characteristic Affecting Visual Attractiveness Pattern recognition may be used to identify features of the area of skin 302 that has been scanned.

Feature Identification
Reflectance and Topology

Feature identification may be based on patterns determined in scanned data, and may have to do with both the reflectance patterns and the surface topology of the area of skin. Mathematical pattern analysis of this data allows identification of specific unattractive features that could benefit from enhancement techniques. As explained below, such features may typically be characterized by age-related and damage-related patterns that are irregular or asymmetrical compared to the more regular and symmetrical genetic-based patterns of younger skin.

The Eye's Perception of Depth

Figure 45:
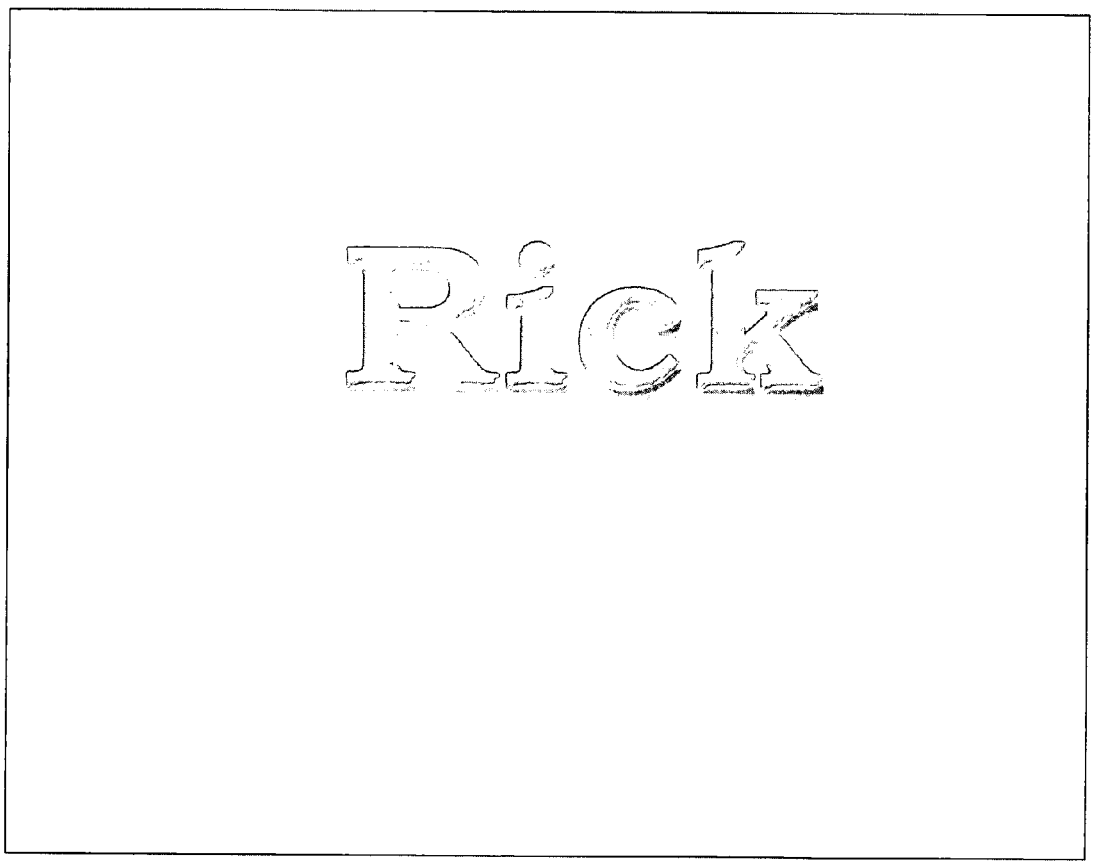
FIG. 45 is an example of a text image showing apparent depth.

At small distances, the human eye perceives depth by stereoscopy. At a typical human interaction range of a few feet, however, the eye perceives depth of human skin based on the reflectance of the skin. A difference in shading between adjacent areas of skin is perceived as a surface texture representing elevation or depth from the surface of the skin. As an example of that perception, FIG. 45 shows the text letters "RICK" which were created in Photoshop™. From an original image of flat letters, the software created the apparent shadows. The human eye interprets the differences in reflectance by assuming that a light source is located in the upper left, and that shadows are created because the text has a raised profile.

This perception of depth from differences in reflectance is also important in the perception of human beauty. The eye interprets differences in shading of skin to be surface texture. That perception of texture can be altered by changing the reflectance of the skin. In the letter example for instance, the perception of raised letters can be dramatically altered by reducing the shadowing around the letters.

The eye perceives the color of the skin and translates that color information into a perception of depth. One aspect of the current invention is to selectively change the reflectance of a portion of the skin in order to alter this perception of depth. This alteration may be made in relatively small areas such as a bump on the skin; or the alteration may be made over larger areas, such as with traditional cosmetics, such as deliberately darkening an area around the eyes or cheeks.

Examples of Unattractive Features

Some examples of unattractive features in skin that can be identified from scanned data are
- Acne,
- Age spots/sun damage,
- Bruises,
- Bumps,
- Cellulite,
- Light spots,
- Pitting,
- Scars,
- Damaged freckles, and
- Wrinkles.

Other unattractive features that also may be identified have to do with artificial patterns that have been added to the skin, such as body painting and tattoos that have faded over time or that have been distorted by changing patterns of the skin itself such as sagging or wrinkling. These features can be identified and then refreshed through the application of RMAs to refresh or enhance their appearance.

Figure 22A:
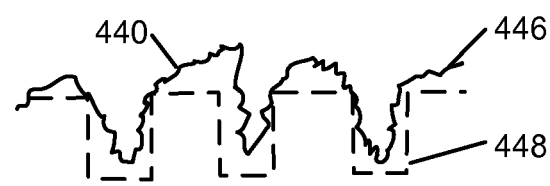
FIG. 22A-C are diagrams that illustrate the effects of RMAs applied to improve the appearance of an age-related freckle.
Figure 22B:
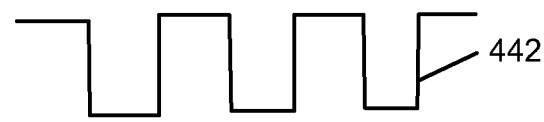

Techniques for Identifying Unattractive Features
Pattern for Age-Related Freckles in a Single Spectral Band For example, natural freckles are about 2 mm across and are sharp edged and have the pattern 442 shown in FIG. 22B. Age-related freckles, caused for example by sun damage, have the pattern 446, shown in FIG. 22A.

Figure 22C:

As explained above, an age-related, random freckle 440, for example from sun damage, on an older person can be identified by its characteristic pattern in a single spectral band, as illustrated in FIG. 22. When scanned data of the random freckle 440 is put into a spectral band, it shows a rough, irregular pattern.

Patterns in Multiple Spectral Bands

Figure 25:
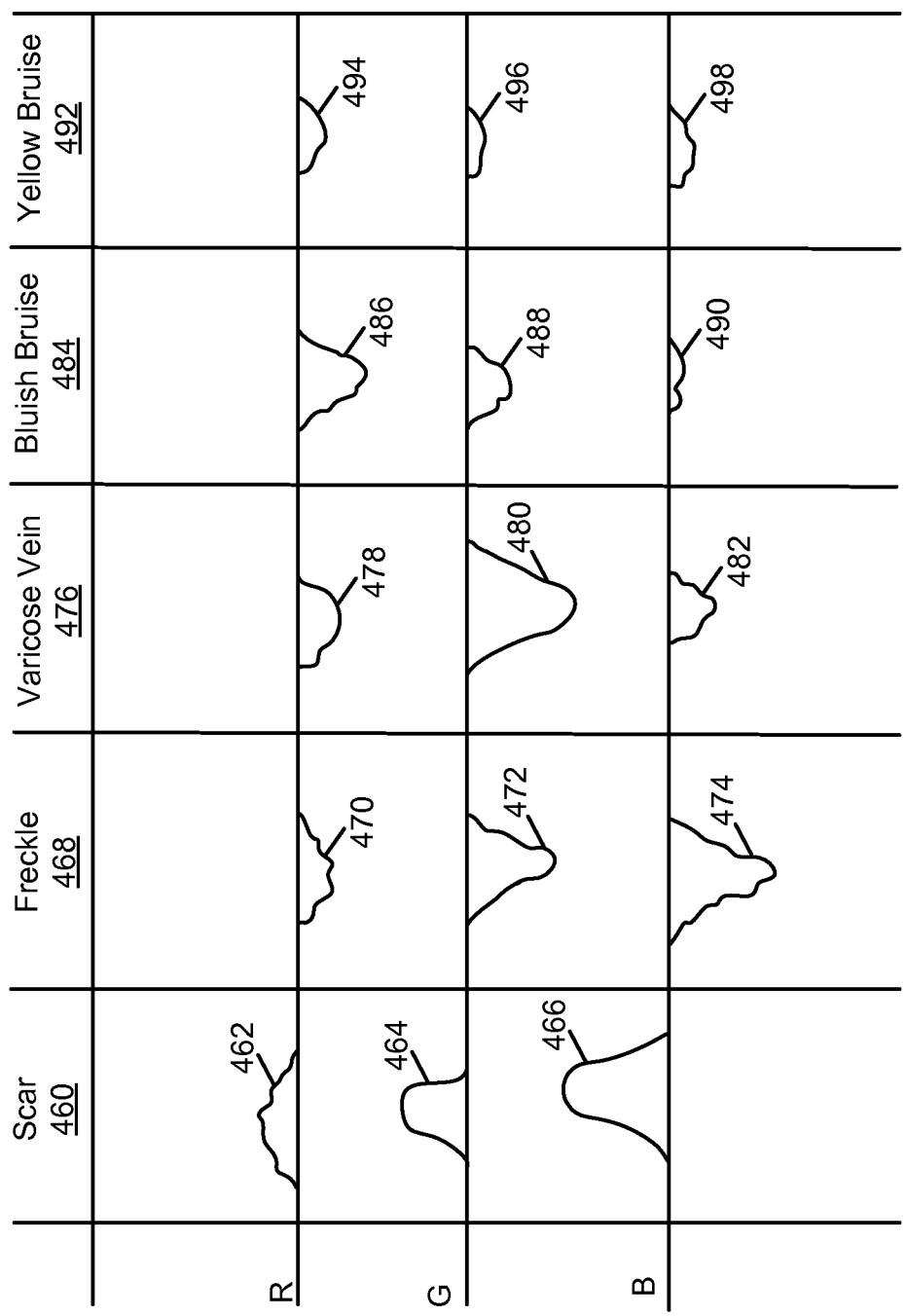
FIG. 25 is a generalized graph of patterns of unattractive features in RGB bands.

By breaking the scanned image into multiple spectral bands, such as RGB bands, the patterns of unattractive features may be identified with even greater clarity. For example, FIG. 25 is a generalized graph of patterns of unattractive features in RGB bands for an area of young skin, showing the empirically observed general patterns of
- A scar 460,
- A freckle 468 from sun damage,
- A varicose vein 476,
- A new, bluish bruise 484, and
- An older, yellow bruise 492.

The set of RGB patterns for each of these unattractive features is quite distinct and thus detectable through feature recognition. For example, the scar 460 shows patterns in the higher frequency range in all three bands 462, 464, and 466, unlike the other features. The freckle 468 dips more deeply into low frequencies in the blue band 474, than the blue-band patterns for the varicose vein 482, the bluish bruise 490, and the yellow bruise 498. The bluish bruise 484 has larger dips in the red pattern 486 and green pattern 488 than the yellow bruise red pattern 494 and green pattern 496. The yellow bruise blue pattern 498 dips more deeply than the bluish bruise blue pattern 490.

Advanced Feature Identification Through Mapping

Mapping based on feature identification can add greatly increased capabilities for enhancement to mapping based on reflectance and surface topology.
- Maintain register over entire skin surface.
- Translate 3-D to lightness/darkness using mean illumination, and include with lightness/darkness attribute, both for printing against or for aesthetic augmentation.

Means of Compensating for Special Conditions
Compensating for Body Hair

In one embodiment, the presence of skin hair may be compensated for by taking images in multiple passes while attempting to orient the hair in various directions. The orientation may be accomplished by a comb device associated with the scanner. In other embodiments, a static electric charge may be used to cause the hair to rise relative to the skin.

Figure 11:
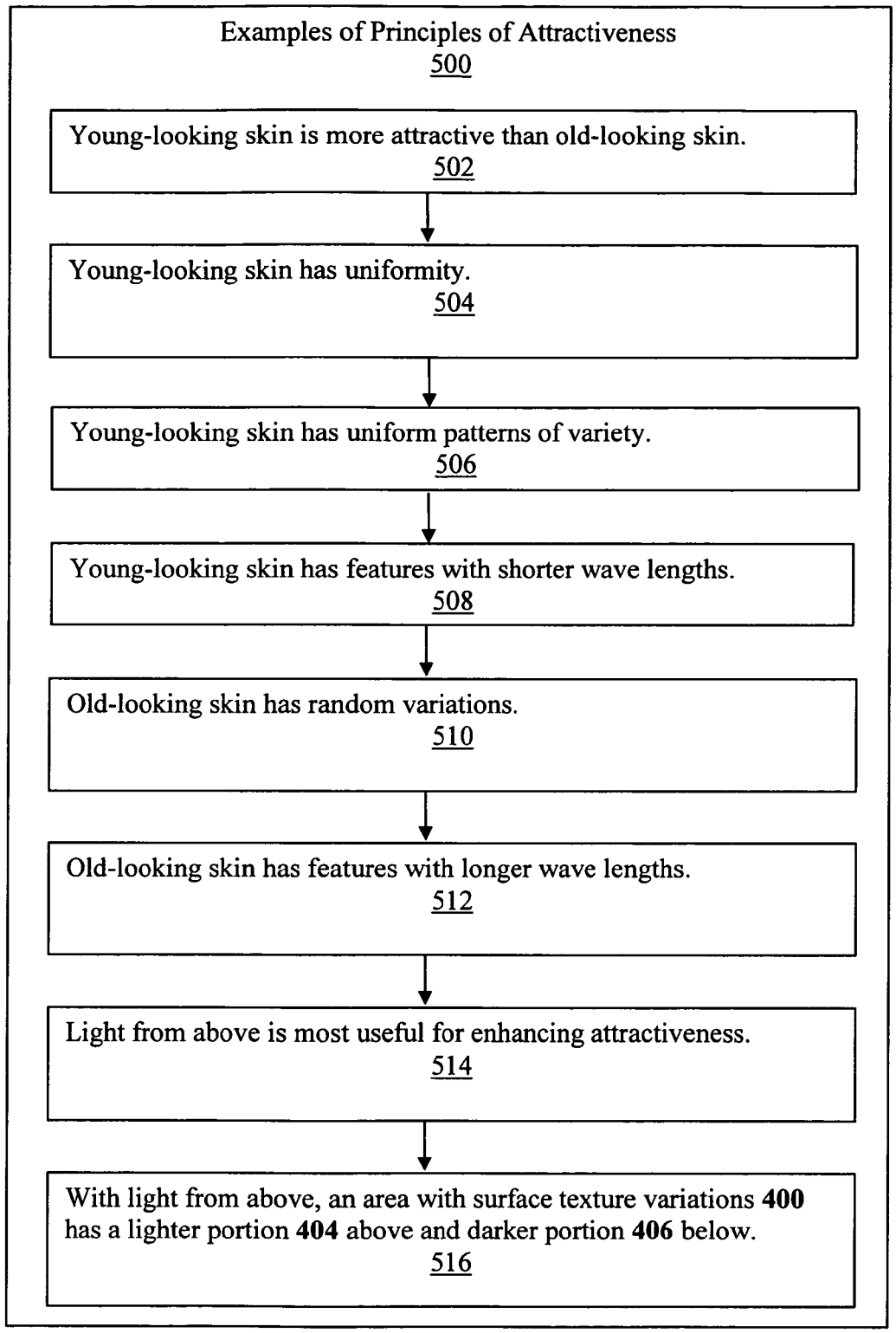
FIG. 11 is a flow chart that illustrates a process defining principles of attractiveness.

Determining a Desired State of the Skin Characteristic
Principles of Attractiveness The present invention employs general principles of attractiveness 500, examples of which are shown in FIG. 11. These principles are based on observation of attributes that many people find attractive and thus represent tendencies in human behavior.

Means of Determining a Desired State of the Skin Characteristic

Approaches for corrections include pure mathematical techniques and artificial intelligence techniques. By contrast, artistic approaches are more intuitive and less quantitative.
- Mathematical
- Artificial Intelligence
- Artistic Mathematical Means Mathematical techniques include filtering to remove a portion of middle frequencies, and to remove a portion of asymmetric low frequencies. Another example of a pure mathematical technique is printing in opposition to an image in order to make the skin appear more uniform. This treatment can vary by spatial frequency, and it is typically preferable to have uniformity in the mid-frequency. Low frequency corrections may be more AI or artistic based for correction over larger areas of the skin.

Figure 28:
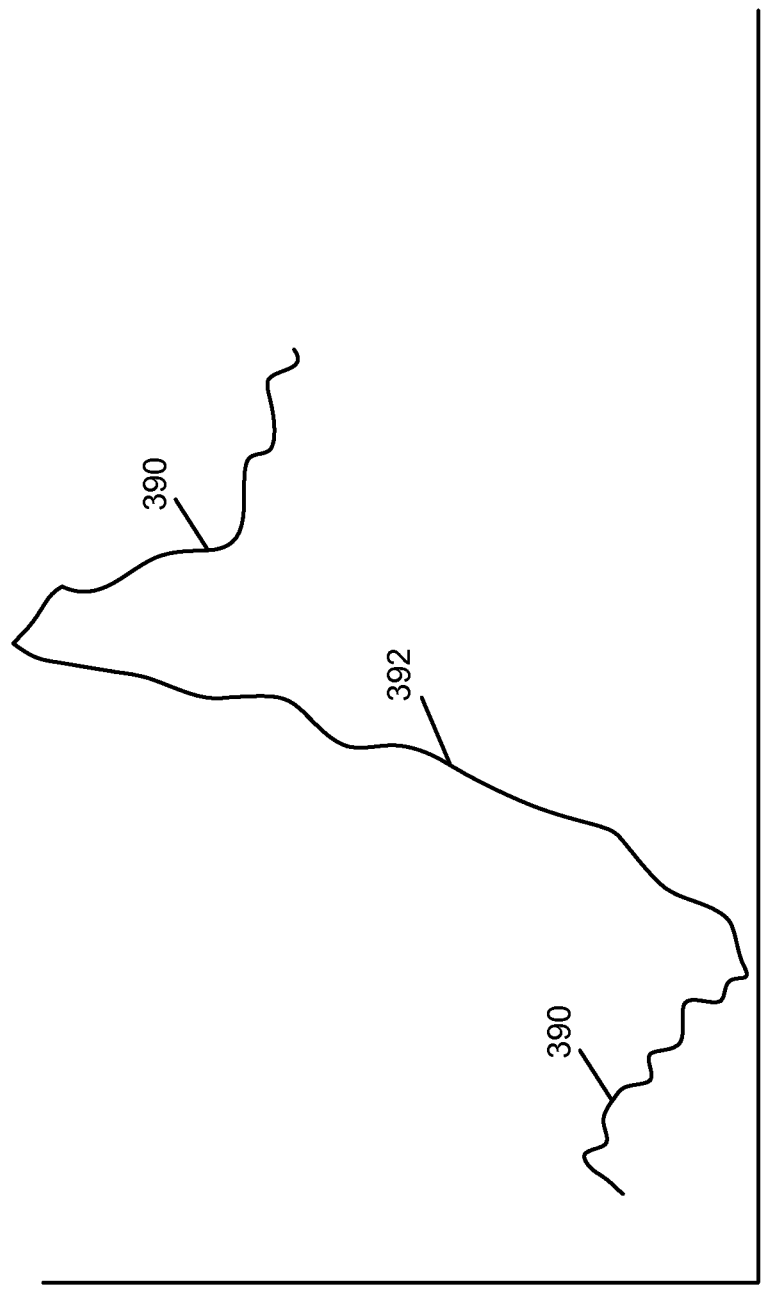
FIG. 28 is a generalized graph of weaker and stronger middle frequencies.

In an embodiment, a low-pass filter may be performed with a desired range of wavelengths. In one example, one half inch to one inch wavelengths are filtered to remove a portion of the middle frequencies. As shown in FIG. 28, weaker middle frequencies 390 show less pronounced swings between light and dark points than stronger middle frequencies 392. In an embodiment, the weak middle frequency components are removed to smooth an image.

Performing a Derivation of the Low-Pass Filter

In an embodiment, a low-pass filter may be performed, such as where a color value for a frexel is replaced by the average color value of its neighbors.

Artificial Intelligence Means

Artificial intelligence techniques include expert systems for detecting particular skin features, and selection of correction strategies. In one embodiment, the skin features are correlated to a registry or map, to identify feature locations. The registry allows for improving faded or distorted body painting and tattooing.

Features Library

Another aspect of AI techniques is the use of a features library for feature identification, and for comparison of actual features with idealized features.

Artistic Means

Computer Controls

In an embodiment, a human observer may optionally use means, such as a computer screen, keyboard, and mouse, to make further modifications in the perceived depth of the scanned area in order to accomplish aesthetic enhancements. A makeup artist or the customer may interact with the computer screen through controls to experiment with enhancements before the application.

A "cosmetic markup language" to provide general instructions such as to darken the top surface of bumps to the left of the nose; or to lighten varicose veins may be employed. The cosmetic markup language simplifies the correction process.

Working with Multispectral Bands

In an embodiment, effective techniques may be employed to enhance the patterns identified in multispectral bands, such as RGB bands. For example, as explained above FIG. 25 shows RGB patterns for a scar 460, an age-related freckle 468, a varicose vein 476, a bluish bruise 484, and a yellow bruise 492, all in young skin. The following techniques are effective when the skin as a whole is being darkened in middle frequencies to smooth it, as explained above.

Scar

To enhance the scar 460, RMAs of magenta and yellow but not much cyan may be applied to it. This adds red color to the pale-looking scar 460.

Varicose Vein

To enhance the varicose vein 476, less of the darkening RMAs may be added to the areas surrounding the varicose vein 476.

Age-Related Freckle

To enhance an age-related freckle 468, less of the darkening RMAs may be added to the area of the freckle 468.

Bluish Bruise

To enhance a bluish bruise, less cyan RMA can be added during the general darkening.

Yellow Bruise

To enhance a yellow bruise, less yellow RMA can be added during the general darkening.

Applying at Least One Reflectance Modifying Agent

Types of Reflectance Modifying Agents (RMAs)

The current invention may utilize a variety of Reflectance Modifying Agents (RMAs), including
Analine,
Food coloring,
UV,
Transparent Dyes,
Transparent Inks,
Pigments,
Oxidizers,
Tanning agents,
Bleaches, and
Chemically altering agent.

For example, a dye does not reflect light, but changes the skin reflectance, acting primarily by absorbing light.

In an embodiment, the RMAs can have a time delay, so that their application does not have an immediate effect but takes effect later through a triggering agent. For example, the RMAs can comprise one or more photosensitive materials that can be selectively exposed by a modulated beam of ultraviolet or other light or other forms of light and later developed by a chemical agent applied uniformly over the surface. For example a photographic emulsion of a light based material may be used, of which silver based halides are a good example.

Multiple Passes

In an embodiment, the RMAs may be applied to the skin by scanning and printing almost at the same time and making multiple passes over the skin. Several advantages result from using multiple pass application. Micro registration problems may be reduced because multiple passes permit dithering or blurring the image, as is well known to those skilled in the art. For example, multiple pass applications are useful for smoothing out the effects of hairs on the skin.

Also, multiple pass applications of RMAs allow time for the skin to assimilate the RMAs, which is especially important because some types of skin will absorb more than others.

The process for multiple pass applications is to make a partial application of the RMAs, then to scan again the area of skin that has received the partial application. A further application of RMAs can be made, and still further multiple pass scanning and applications can be made to approach an aesthetic goal.

Drop Control Application Techniques

Substances may be applied with "flow control" devices. These flow control devices typically may be characterized as "drop control techniques" where individual droplets of the substance are controlled; or "non-drop control techniques".

Spray devices and electrostatic spray devices are non-drop control techniques where droplets are produced and controlled only in aggregate. Often in a spray device, a lack of individual droplet control, or "randomness" is desired in order to produce a smooth application over a relatively large area. By contrast, in the current invention, it is desirable to provide very specific control of the amount and placement of medicinal agents.

Examples of drop control include "fine flow control" where the flow of the substance is precisely controlled to deliver droplets as desired; and "inkjet technologies". An older inkjet technology includes supplying a continuous flow of charged droplets past electrostatic deflector plates which are alternately charged so that the plates either permit a droplet to pass or deflect to a gutter. This technique was the original design basis for inkjet printers.

Other inkjet technologies include "drop on demand" such as thermal devices provided by Hewlett Packard, and piezo-electric devices such as provided by Epson and other printer manufacturers. In one embodiment of the current invention, the drop on demand technology is combined with charging the droplets.

Another embodiment of the current invention is the use of the older inkjet technology in a manner that delivers charged droplets in a scanned direction beam. Modern inkjet printers have been optimized for printing on flat surfaces over limited distances. The current invention prints on skin which is a dimensioned surface, and often requires a greater throw distance for the droplets. This greater throw distance can be facilitated with the better droplet aiming that is possible with a charged droplet.

In another embodiment of the current invention, a non-inkjet drop control technique is used, such as fine flow control techniques.

As mentioned above, in this patent specification, the phrase "inkjet printer" is used for brevity represent any form of inkjet technology.

A particularly useful technique for the present invention is to employ "drop on demand" technology, a subset of drop control technology, which charges the droplets electrostatically. One of the advantages of applying charged droplets are that the applicator may be placed farther from the skin than is otherwise possible, whiled maintaining accuracy. Another advantage is that because hair is not grounded, the hair may be charged to the same level as the charged droplets so that the hair does not interfere with applications to the skin. For example, drop on technology may be used to apply a single droplet of white pigment to spot in the face with pixel-level precision.

In an embodiment, an inkjet printer may be used to apply the RMAs or medicinal agents onto the surface of skin, printing at a resolution of 300 dpi (11.8 dpmm).

In an embodiment, the inkjet printer may have multiple printer heads to speed the application. It may also traverse the body by robotics.

It is desirable to control the application of RMAs or medicinal agents to a desired spray range. In one example, an inkjet printer has a desired spray distance of about ⅛ inch (3.2 mm). Various techniques may be used to guide the printer element over the surface of the skin in order to maintain that desired spray distance, such as a cup, as shown in FIG. 26.

In an embodiment, the head of the inkjet printer has a comb to keep hairs on the skin even and in fixed pattern, to smooth the hairs.

Detailed Description of
Embodiment—Mapping-Based Monitoring

Example—Generating a Map of the Skin

This example demonstrates one method for generating a map of the skin, analyzing the map to generate a corrective plan, and executing the corrective plan. In this example, a corrective plan typically refers to one or more application of at least one medicinal agent. In other examples, the plan may include a closer monitoring of a region of skin, without the application of a medicinal agent.

Step 1—Scan Skin and Generate a Map of the Skin

In this example, the map of the skin is generated from data collected by scanning the skin at a first time.

In this example, the general process of creating a map of the skin involves obtaining data by scanning the frexels, and then processing that data to create the map. In this example, the processing includes determining the location of the scanning device and the frexel with respect to a reference coordinate system, determining the reflective properties of the frexel in multiple wavelengths, and determining the tilt or orientation of the frexel with respect to the coordinate system. Information about the frexel and its neighbors is then processed to make fine adjustments to the location of the frexel with respect to a portion of the body such as a face, so that a map can be generated. This fine adjustment includes referencing the frexel to the face, such as by referencing the frexel relative to recognized facial features.

a. Data Representation

An example of the data representation for a frexel is shown below:

$$(x_s, y_s, z_s, \alpha_s, \beta_s, \gamma_s),$$

$$(x_f, y_f, z_f, \alpha_f, \beta_f, \gamma_f),$$

$$\{(refl)_A, (refl)_N, (refl)_S, (refl)_E, (refl)_W\}$$

In this example, $(x_s, y_s, z_s, \alpha_s, \beta_s, \gamma_s)$ and $(x_f, y_f, z_f, \alpha_f, \beta_f, \gamma_f)$ represent the position and angular orientation of the scanner sensor and the frexel relative to a coordinate system.

b. Frexel Location Relative to Sensor or Coordinate System

The data elements $(x_s, y_s, z_f, \alpha_s, \beta_s, \gamma_s)$ may represent the distance of the frexel from the sensor, or may be an absolute position and orientation of the frexel with respect to a reference coordinate system. In one example, the determination of the distance from the frexel to the scanner may be made in two steps. A first step can be an approximate mechanically-based measurement such as a constant height of the sensor from the skin. The second step can be an optical first derivative measurement to provide a fine adjustment. In one example, the fine adjustment is calculated by measuring an angle from the surface. In another embodiment, a fine adjustment may be made by using two light sources to send out two reference points or grids for detection by a sensor.

c. Reflectance and Illumination Data and Calculations

The data elements $\{(refl)_A, (refl)_N, (refl)_S, (refl)_E, (refl)_W\}$ represent reflective data for the frexel under ambient lighting conditions, and for each of four light sources, such as LEDs, which are arbitrarily designated as north-south-east-west for ease of discussion. Other numbers of light sources, such as three sources, can be used, but the mathematics is simplified with four light sources. The (refl) represents one or more data point for the reflectance measurement.

The frexel data can be processed to determine a reflectance and an illuminance for each light source, and that information can be used to determine reflectance and surface profile.

In one example, the reflectance is the average or mean of all measurements. The illuminance can be determined from the known brightness of light sources such as LEDs.

d. Frexel Orientation

By determining the tilt of the frexel relative to two orthogonal axes, the orientation of the frexel can be determined. The orientation of a frexel and its neighbors is an indication of the actual local surface texture of the skin. One aspect of the current invention is the ability to measure and compensate for both local reflective properties and local surface texture.

In this example, there are four light sources which are designated as North, South, East, and West. The sensor obtains data when each light source is on, and the other sources are off. The sensor may also obtain data for ambient lighting, with none of the four light sources on. The tilt of the frexel can be determined by comparing the North and South measurements. The difference between these measurements is a related to the tilt of the frexel along the North-South axis. The difference between the East and West measurements is a related to the tilt of the frexel along the East-West axis.

e. Data Representation for Derived Values

An idealized data representation for data from a frexel is shown below. Various compression methods can be used to reduce the data storage requirements. In this example, each data element is shown as a complete set in order to demonstrate methods of registering the data and creating a map.

frexel data (x,y,z)
 NS tilt,
 EW tilt,
 (R, G, B visual color albedo),
 time of acquisition ;

The (x,y,z) represents the location of a frexel with respect to a coordinate system. The NS tilt represents the tilt of the frexel relative to the EW axis. The EW tilt represents the tilt of the frexel relative to the NS axis.

The (R, G, B visual color albedo) represents the measured reflectance of the frexel in the red, green, and blue spectrum. One aspect of the current invention is that data may be obtained for multiple wavelengths, and that different wavelength data is useful in identifying skin features.

The human eye sees both reflectance and topology. In one embodiment of the present invention, data is obtained for both reflectance and topology.

Step 2—Register the Groups of Frexels.

The second step is to make some sense out of the data from a plurality of frexels.

This portion of the example is analogous to the problem of mapping the earth's surface from satellite or aerial photographs. In the case of aerial photos, a large number of photographs are slightly scaled, rotated, and/or translated in order to permit the images to be properly overlapped to reflect the actual earth surface. The map can then be generated from the properly overlapped images.

In the present example, one source of complexity is that data is captured at slightly different acquisition times, and it is necessary to compensate for movements of the skin and slight errors in calculated position.

This motion aspect is analogous to modeling in a gaming application. In gaming, a model of the body may include a model of the skeleton so that the body may be related to the skeleton. Movement may first be applied to the skeleton, and then the position of the body can be calculated from knowing the position of the skeleton and knowing the relationship between the skeleton and the body. In the current invention, the problem is the reverse, in that the shape of the body has been determined, and it is desirable to correct for motion during the measurement, a. Mapping a Frexel to a Map In this example, it is desirable to associate a frexel, or a group of frexels, with a position on a map. For instance, the frexel may be a portion of a face, and the map is an idealized map of a face.

In the case of a face, a model could be a rigid and upright face in an expressionless pose.

In one embodiment the determination of the desired amount of each of a plurality of dyes to be applied is made by
 generating a map of the skin at a first time; and
 analyzing the map to generate a corrective plan.

The corrective plan is then executed at a second time by making at least one pass with a device which includes a scanner and a dye applicator. The scanner provides data that is used to determine the location of the applicator and to determine how much additional medicinal agent is required for that location at each pass.

Detailed Description of Embodiment—Examples of Method

To illustrate embodiments of the present invention, examples are given below for enhancement or monitoring processes for the following areas of human skin:
 A face,
 A leg, and
 A breast.

Enhancing a Face

Undesirable and Desirable Characteristics in a Face

Figure 13:
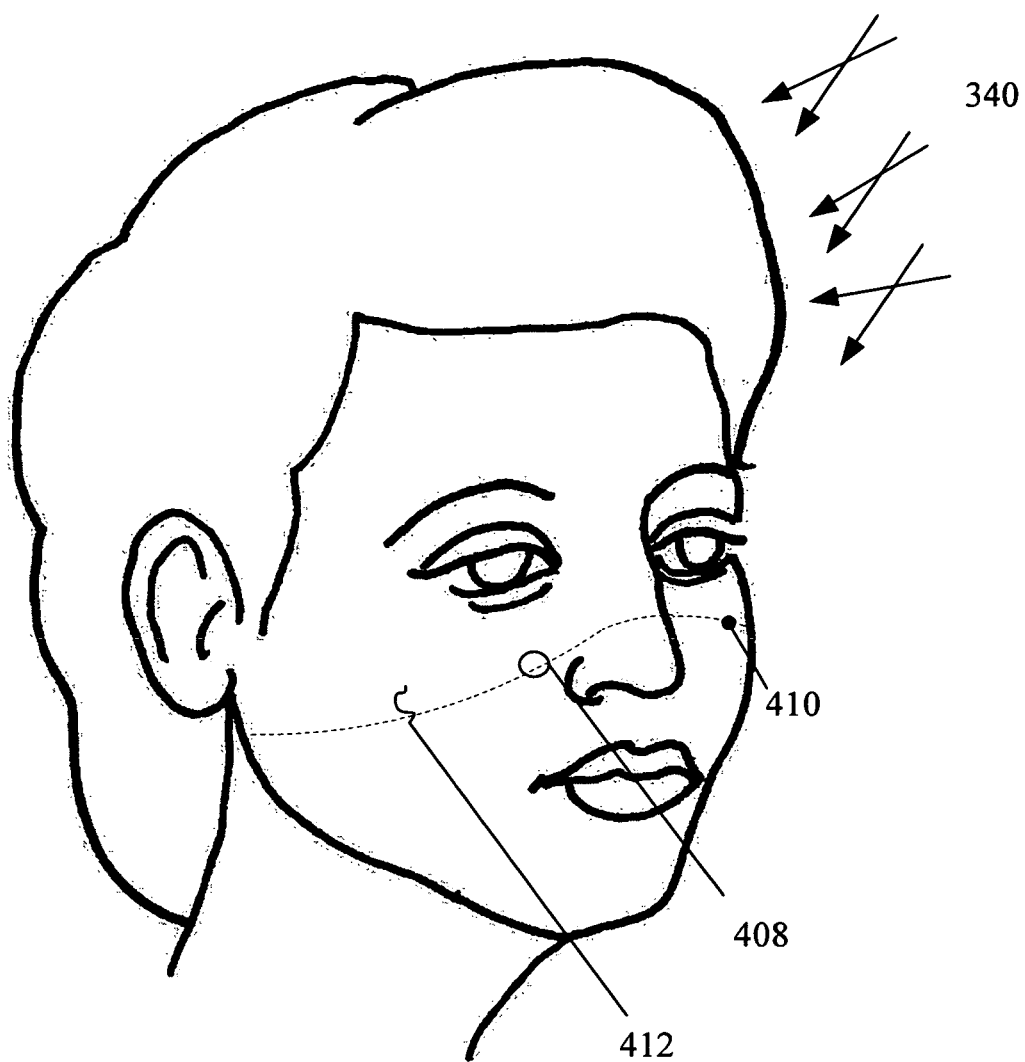
FIG. 13 is a diagram that illustrates characteristics or features on a 3-D human face.

FIG. 13 represents a human face 235 with certain characteristics:
 A light spot 408,
 A freckle 410, and
 A non-uniformity 412 such as a scar.

FIG. 14 shows a representation of a 2-D surface map 232 of the face shown in FIG. 13, resulting from the scanning process used by the present invention and described above. This 2-D surface map 232 in FIG. 14 retains the characteristics listed above, which may be identified by pattern recognition:
 A light spot 408,
 A freckle 410, and
 A non-uniformity 412 such as a scar.

Note that the 2-D surface map 232 typically includes a representation of depth in order to capture the shape of the face.

To enhance such a face 235, shown in FIG. 13, according to the principles of attractiveness given above, it may be desirable to reduce or delete from view the undesirable characteristics, such as the light spot 408 and the non-uniformity 412. At the same time, it may also be desirable to retain or even augment the appearance of a characteristic such as a freckle 410, which can be a characteristic of youthful-looking skin. Unlike prior cosmetic techniques, which tend to cover over both undesirable and desirable features with makeup, the present invention can distinguish between the two and treat them appropriately.

Putting the Scanned Image into Spatial Frequency Bands

As shown in Step 606 of FIG. 31 and described below, the application algorithm 230 puts the scanned image into spatial frequency bands, in an embodiment, to permit identification of characteristics.

FIGS. 16A-E represent the patterns of the 2-D face 232, shown in FIG. 14, after the data has been put into spatial frequency bands.

Albedo

The top band in FIG. 16 represents the actual "albedo" of the 2-D surface map 232. A rise in the actual albedo graph identifies the light spot 408. A deep, sharp drop in the graph identifies a non-uniformity 412 such as a scar. And an irregular section identifies a freckle 410.

Illuminance (Shading)

The spatial frequency bands also graph the actual illuminance (shading) of the 2-D surface map 232.

Feature Recognition

Figure 15:
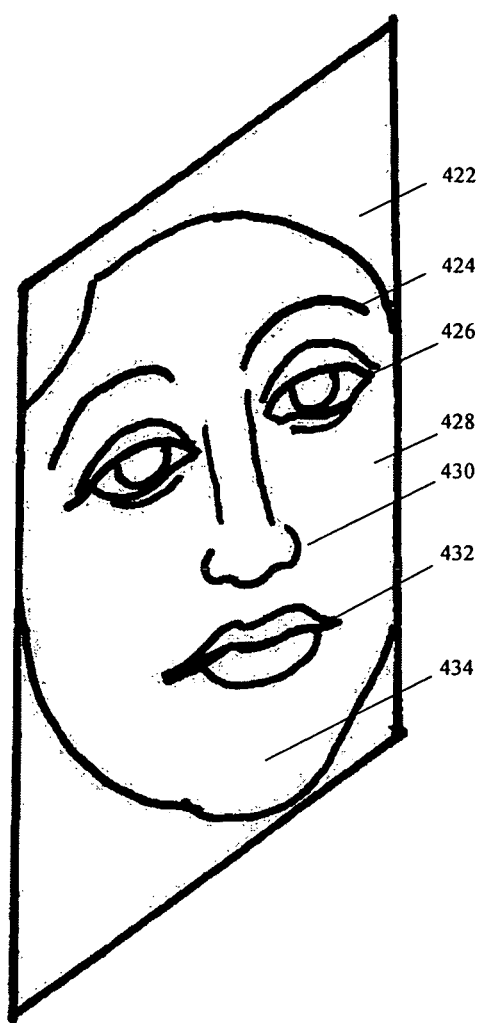
FIG. 15 is a perspective diagram that illustrates characteristics or features on a 2-D map of a human face.

FIG. 15 shows that pattern recognition can also identify features in the scanned 2-D surface map 232, such as
 Hair 422,
 An eyebrow 424,
 An eye 426,
 A cheekbone 428,
 The nose 430,
 The mouth 432, and
 The chin 434.

By identifying such features, the application algorithm 230 can determine whether to make enhancement or medicinal application to those features. For example, it is normally undesirable to print on an eye 426. Therefore, the application algorithm 230 can remove the area that represents the eye 426 from consideration.

Tracking

Figure 3:
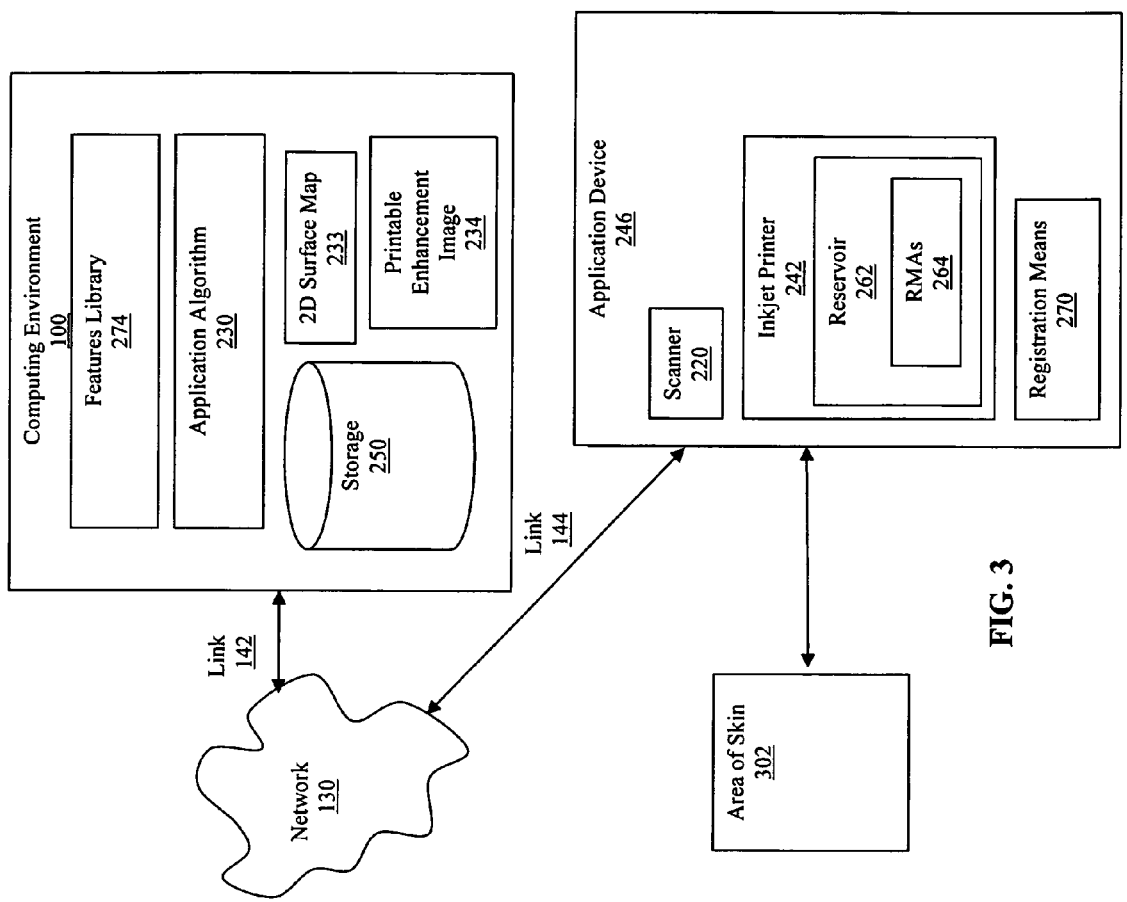
FIG. 3 is a block diagram showing an operating environment in which embodiments of the present invention may be employed for applying RMAs onto skin through communications over a network and a portable application device.

The application algorithm 230 may also use pattern recognition for tracking the location of the application device 246, for example the one shown in FIG. 3, on the area of skin 302.

As mentioned above, chemical markers may be alternately applied to the area of skin during the scan to help create the map and enable subsequent tracking of the map with the area of skin 302. For example, ultraviolet markers may be used.

Comparing Features with Idealized Features

Figure 2:
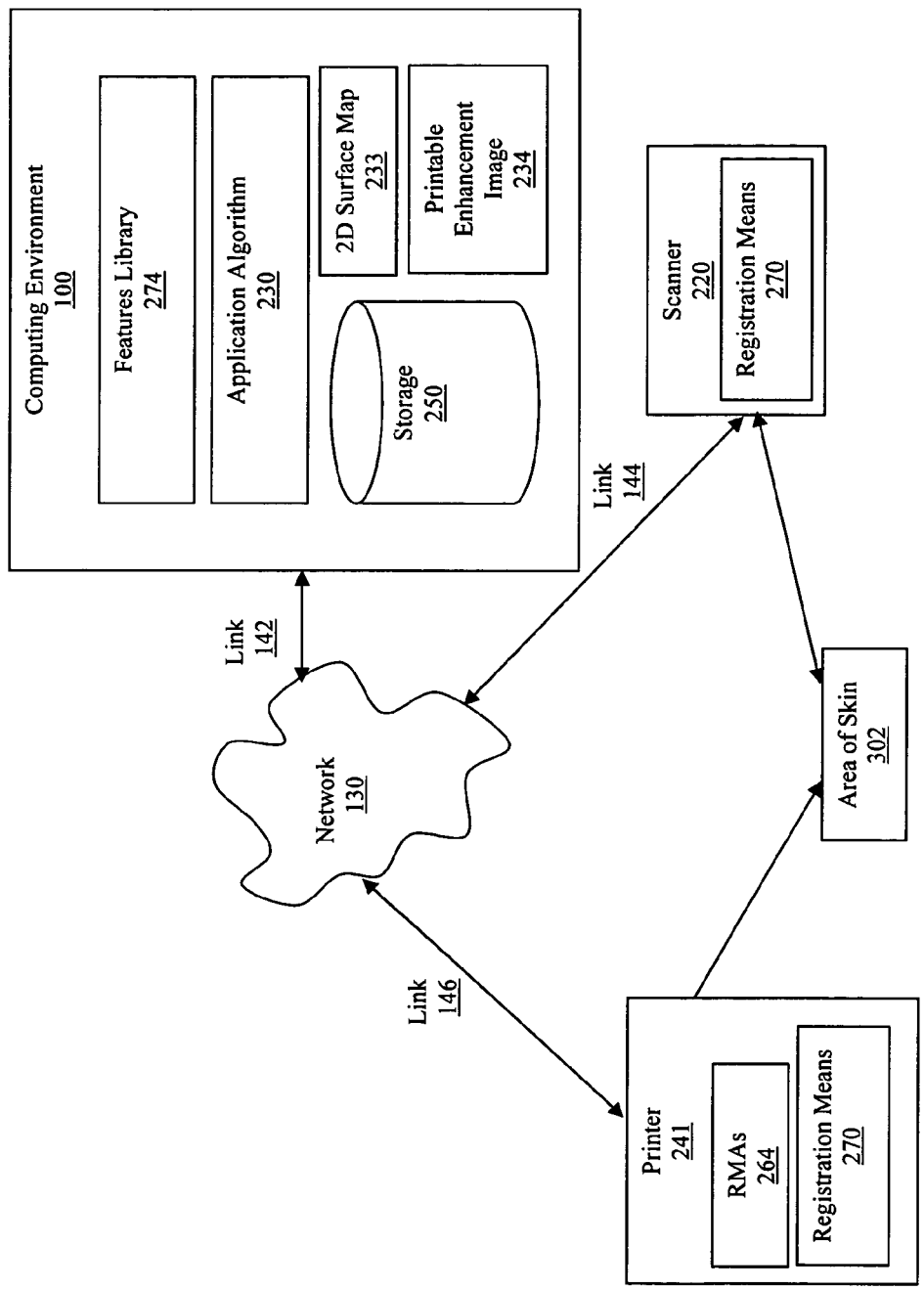
FIG. 2 is a block diagram showing an operating environment in which embodiments of the present invention may be employed for applying RMAs onto skin through communications over a network.

The application algorithm 230 may compare the mapped physical features with the idealized features in a features library 274, shown in FIG. 2, and use the comparison to modify features. In the current invention, this comparison may be a scanned skin feature compared to images from a medical database to assist in diagnosis.

Thus the application algorithm 230 may apply to scanned features global guidelines established in the features library 274, shown in FIG. 2.

Determining the Actual Depth

Scanning the area of skin 302 provides the actual depth.

Determining the Aim Depth

In an embodiment, the aim depth can be the low spatial frequencies only of the actual depth. However, aesthetics may dictate additional sculpting, through further mathematical or manual input. The aim depth encompasses the effect of illuminance on perceived depth or texture, and is related to the amount and angle of incident light.

Carrying Out a Low-Pass Filter

In an embodiment, a low-pass filter may be performed with one half inch to one inch (12.7 to 25.4 mm) wavelengths to determine the aim depth to accomplish smoothing.

Determining the Actual Illuminance

Both actual and aim depths are translated into surface angle, as the first derivative, or slope, of depth. The surface angle is then translated into illuminance of the surface, as is well understood in 3-D modeling in applications such as gaming or animation graphics. Typically the assumed illumination angle and diffusion is mean light reaching the human skin.

Determining the Aim Illuminance

An aim reflectance may be derived algorithmically again simply as the low-pass version of the actual reflectance. However, additional aesthetic attributes may be added through mathematic or manual input.

Determining the Actual Albedo

The actual albedo is determined by the sensor of the application device, as described above.

Determining the Aim Albedo

The aim albedo is determined by the principles of correction explained above.

In this example, a generalized smoothing is performed, and specific feature correction is performed. For example, the light spot would be darkened, the freckle would be retained and possibly sharpened, and the scar would be at least partially camouflaged by a general darkening of the skin and a specific darkening of the light area on top of the scar.

The aim albedo is the desired perceived reflectance after calculating the smoothing and feature correction.

In other examples, the aim albedo may also include artistic strategies such as darkening one portion of a face relative to another.

Applying Aesthetic Objectives

In an embodiment, a human observer or medical technician may optionally use means, such as a computer screen, keyboard, and mouse, to make further modifications in the actual depth of the scanned area in order to accomplish aesthetic enhancements.

The Enhanced Appearance of the Face

Figure 17:
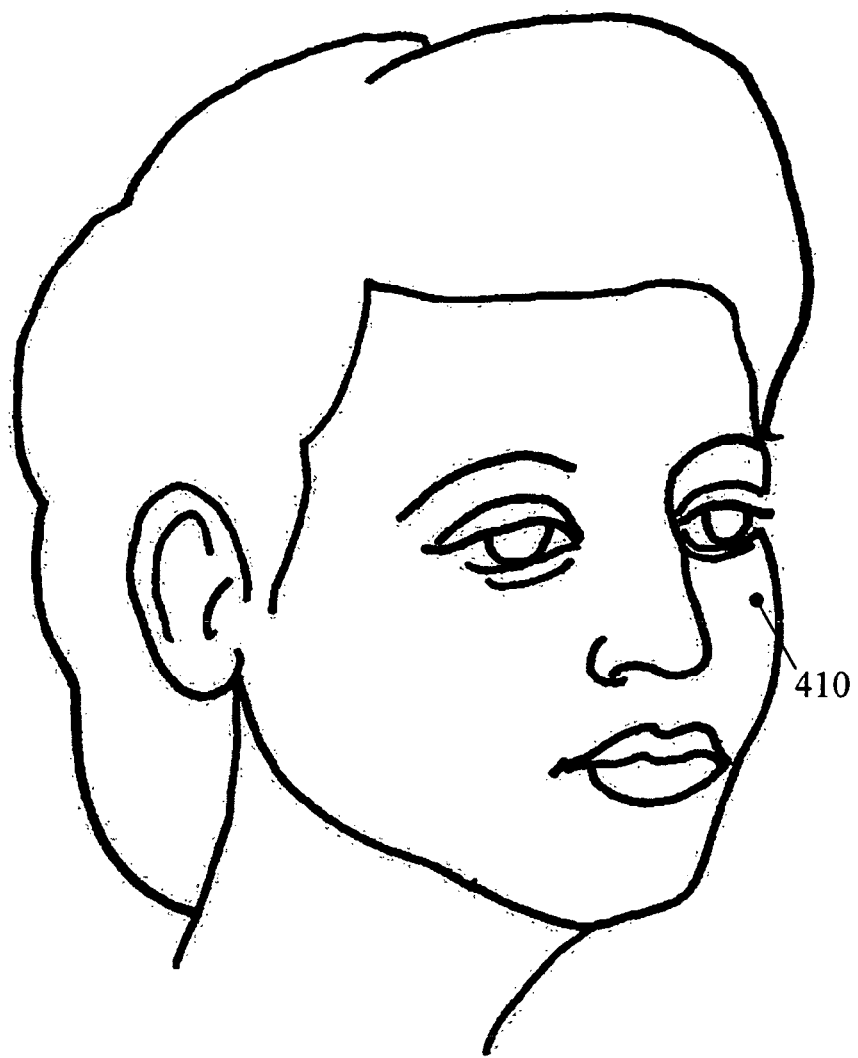
FIG. 17 is a diagram of a 3-D human face that has been enhanced through printing of RMAs according to a printable enhancement image.

FIG. 17 shows an example of the enhancement through the application of RMAs of the appearance of the face 235 portrayed in FIG. 13. The light spot 408 and non-uniformity 412 shown in FIG. 13 have been removed in FIG. 17. However, the freckle 410 has been retained in FIG. 17 as an attractive pattern of variety.

Single-Pass or Multiple-Pass Systems

Single-Pass

With sufficient computing power, the application device 246 will only need to make only one pass across the area of skin 302 to both scan the data and apply the RMAs 264.

Multiple-Pass

In an embodiment, the user moves the application device 246 over the area of skin 302 many times. The application system then scans continually, creates a new 2-D surface map 233 after each pass, uses the 2-D surface maps 233 continually to identify the landscape of the area of skin 302 and calculate new printable enhancement images 234 with each pass, and applies only a portion of the RMAs 264 or medicinal agent, for example 10%-20% of the RMAs 264, on each pass. The use of multiple passes thus lets the application system 200 make a partial application of the RMAs 264, view the results of that application, and then make another partial application for further improvements. The continuation of these passes can ensure increased accuracy in the desired result. Application of the RMAs 264 in multiple passes also reduces the possibility of streaking and allows the RMAs 264 to dry between applications for greater effectiveness.

Figure 21:
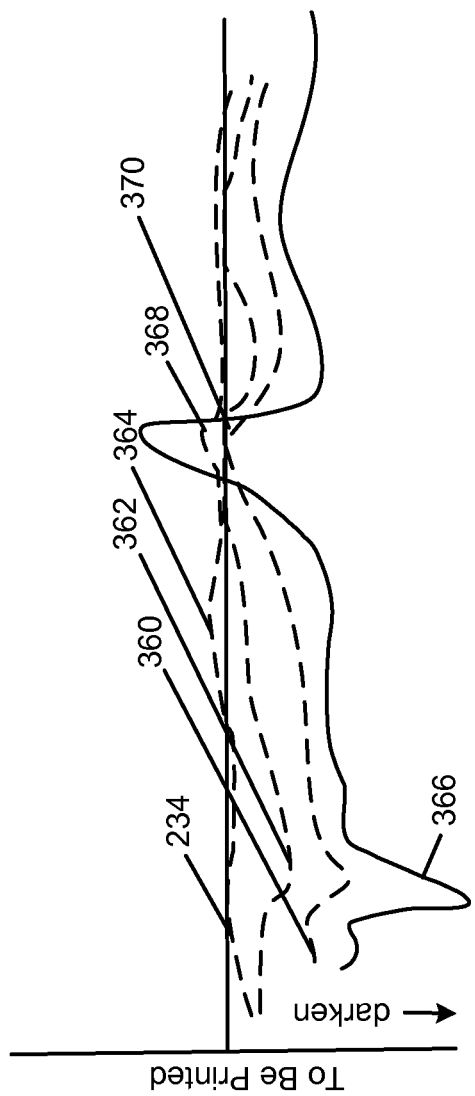
FIG. 21 is a diagram that illustrates performing multiple passes of scanning and applications.

FIG. 21 illustrates how multiple passes may be used to apply a printable enhancement image 234 (exact aim) to an unprinted surface 366.

Overlap Areas

In some examples of the current invention, it is desirable to make multiple passes of the applicator over an area. In the general case, as the applicator crosses over an area in a subsequent pass, some frexels will be seen for the first time, other frexels will have had a previous first pass, and still other frexels will have had two previous passes, etc. It is desirable to keep track of how many times each frexel has been passed over, so that this information can be included in the control algorithm for applying a desired amount of RMA.

It may be desired to correct, by example, 50% of the aim depositions of RMAs or medicinal agent on a first pass. In the observation phase of the second pass, it may be noted that the application has produced more or less than 50% of the desired correction. Suppose this was seen to be 60%; so, only 40% remains uncorrected, and in addition it is now known that this part of the skin is responding with 6/5 stronger response to the RMA. So, by calculation only 5/6×4/5=2/3 of the RMA would be needed on the second pass to attain the desired effect. Suppose instead the algorithm chooses to deposit less than this on the second pass, then on a third pass makes a final observation and final calculation of efficiency and final deposition, to precisely titrate to the desired effect by feedback.

It is possible that the multiple passed could be in sequential scan order; so a top side of the probe always sees fresh skin, a middle processes an intermediate pass, and a bottom processes a strip of skin for the final pass. A more practical system allows random movement similar to the motion of an electric shaver, in which case software tracks the number of times a frexel of skin has been operated on. A sonic or tactile feedback could indicate the completion for each frexel, like an electric shave changes sound depending on completion of effect under each pass.

Since it is generally impractical to exactly meet an edge from a previous application pass, it is also generally desirable that the extreme portions of the applicator make a weaker application of RMA than in the middle of the pass. For instance, if the applicator were moved left to right on this page, then a lesser amount of RMA than calculated would be applied by the top and bottom portions of the print head so that there was an opportunity on a subsequent pass to print additional RMA in those areas to provide a better overlap of passes. It is also desirable to make each pass in a different orientation relative to the skin to randomize measurement or deposition fluctuations due to hairs, skin texture, or pulling distortions of skin, and not to repeat the same paths. For instance, if a first pass were made left to right, a second pass might be tilted slightly clockwise, and a third pass tilted slightly counterclockwise.

Summary of Enhancement Process

Figure 46:
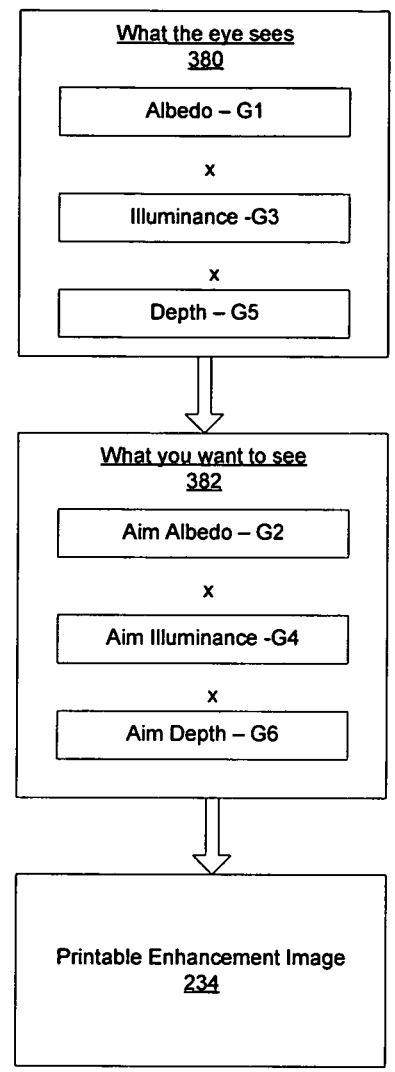
FIG. 46 is flowchart illustrating a correction process.

FIG. 46 shows the general process of one embodiment of the present invention to visually enhance objects such as an area of skin comprising a human face, in an embodiment. "What the eye sees 380" represent the scanned data about the area of skin 302. In terms of optics, this data comprises the albedo G1—which is the degree of reflectance from the surface of the area of skin 302;

the illuminance G3—which is the degree of illumination G3 of the area of skin 302; and the depth G5—which is the distance from the scanner or other reference point to the portion of skin being measured the "tilt" or orientation of the portion of skin being measured. This orientation, when combined with information from adjoining skin areas, describes a surface profile of the skin.

"What you want to see 382" represents an enhancement that would make more attractive "what the eye sees 380." This enhancement, which may be calculated mathematically and optionally through manual visual corrections, comprises an aim albedo G2—which is a more attractive degree of reflectance from the surface of the area of skin 302;

an aim illuminance G4—which is a more attractive degree of illuminance G3 of the area of skin 302; and an aim depth G6—which is the desired perceived distance from the scanner or other reference point to the portion of skin being measured Note: In one embodiment, the correction to be applied is a mixture of transparent dyes, such that the mix and the amount of the dye is determined in response to the perceived reflectance of the local area of the skin—which is related both to the actual reflectance and to the skin surface profile. Thus the correction applies a desired RMA to compensate for actual reflectance, and applies a shading to hide or enhance surface features.

In an embodiment, the mathematical calculations to create the aim albedo G2, aim illuminance G4, and aim depth G6 may be performed with particular effectiveness through mid frequency filtering.

By calculating "what you want to see 382" according to the principles of attractiveness given above, a printable enhancement image 234 may be created for printing on the area of skin 302 to make that area of skin 302 more attractive.

Steps in the Enhancement Process

Figure 33:
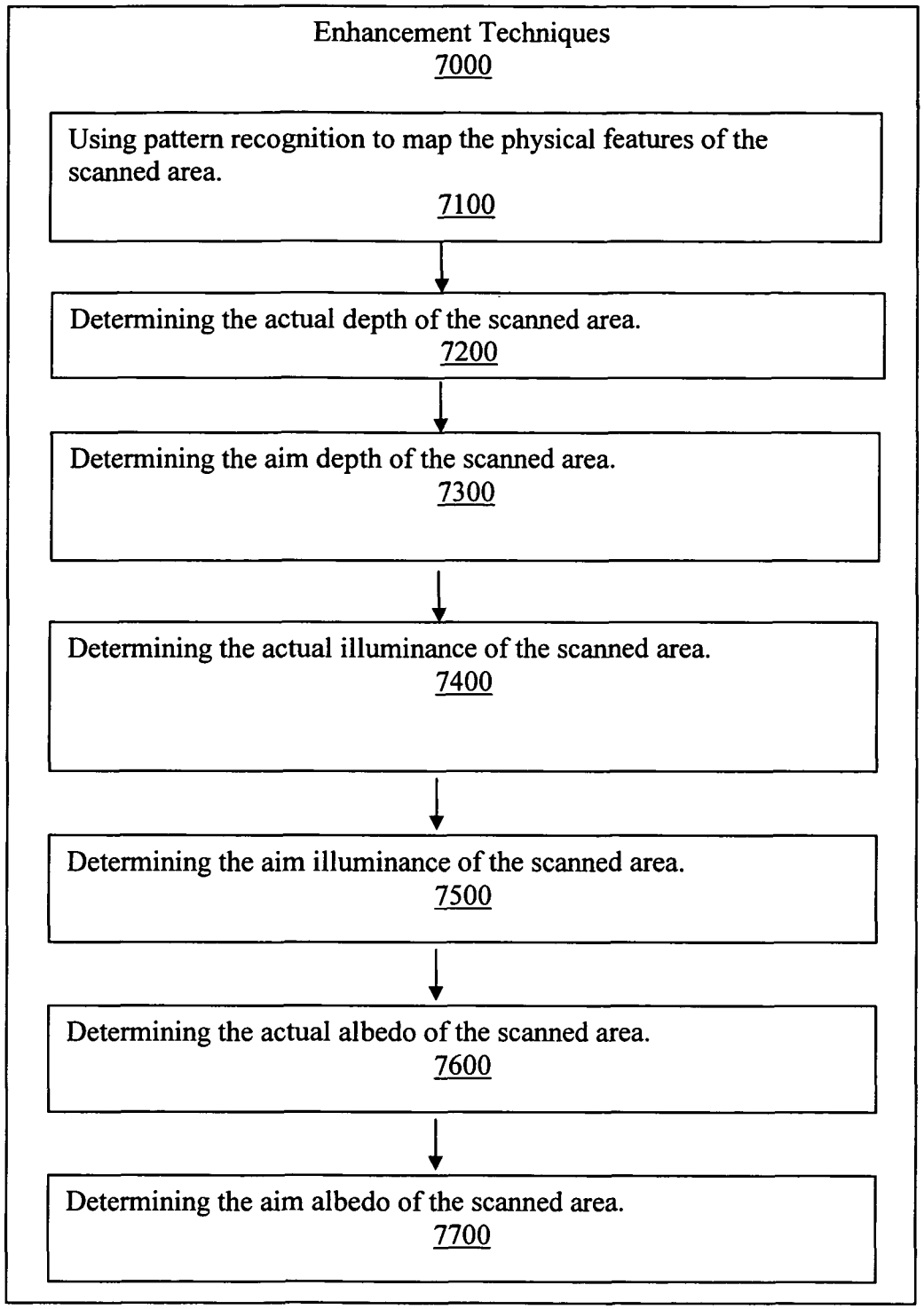
FIG. 33 is a flow chart showing a process for employing enhancement techniques.

FIG. 33 shows steps in a process for accomplishing the present invention's enhancement techniques in an embodiment:

Step 7100 of FIG. 33—Using pattern recognition to map the physical features of the scanned area;

Step 7200 of FIG. 33—Determining the actual depth of the scanned area.

Step 7300 of FIG. 33—Determining the aim depth of the scanned area.

Step 7400 of FIG. 33—Determining the actual illuminance of the scanned area.

Step 7500 of FIG. 33—Determining the aim illuminance of the scanned area.

Step 7600 of FIG. 33—Determining the actual albedo of the scanned area.

Step 7700 of FIG. 33—Determining the aim albedo of the scanned area.

Figure 34:
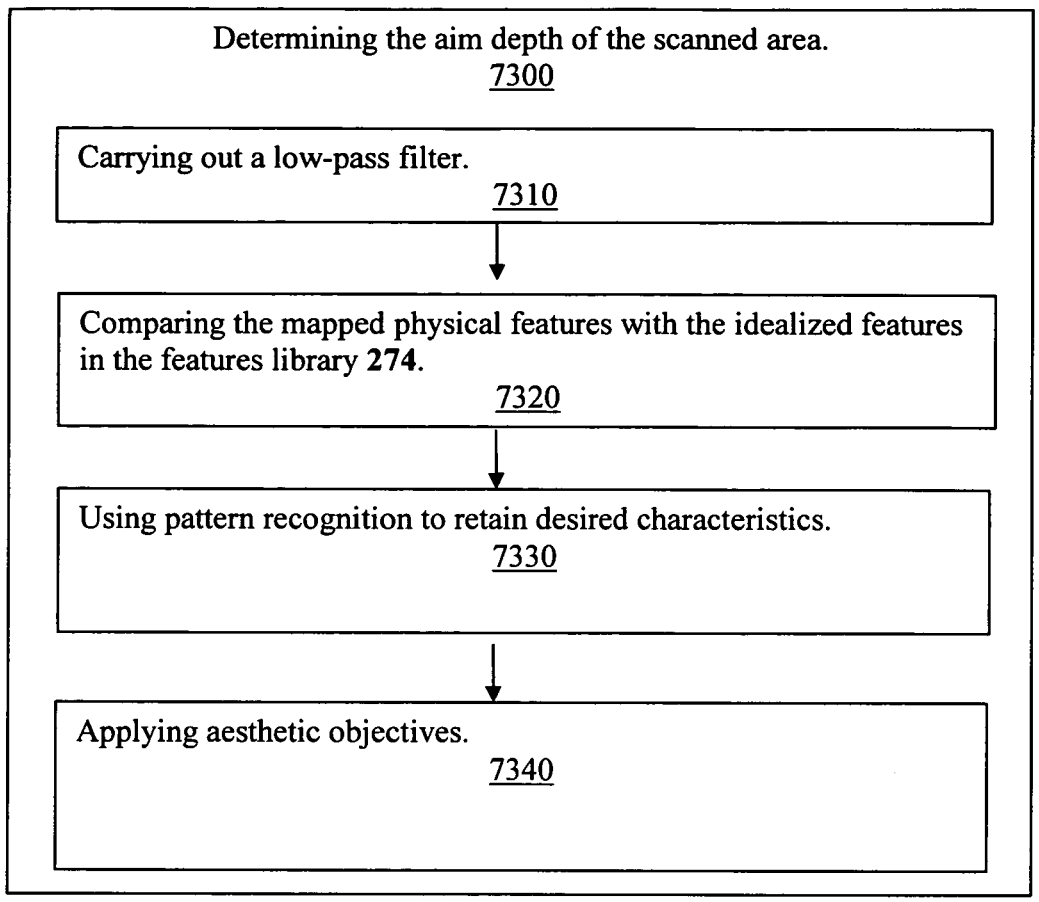
FIG. 34 is a flow chart showing a process for determining the aim depth of the scanned area.

FIG. 34 shows steps in a process for accomplishing step 7300 of FIG. 33.

Step 7310 of FIG. 34—Carry out a low-pass filter.

Step 7320 of FIG. 34—Compare the mapped physical features with the idealized features in the features library 274.

Step 7330 of FIG. 34—Use pattern recognition to retain desired characterisitics.

Step 7340 of FIG. 34—Apply aesthetic objectives.

Figure 35:
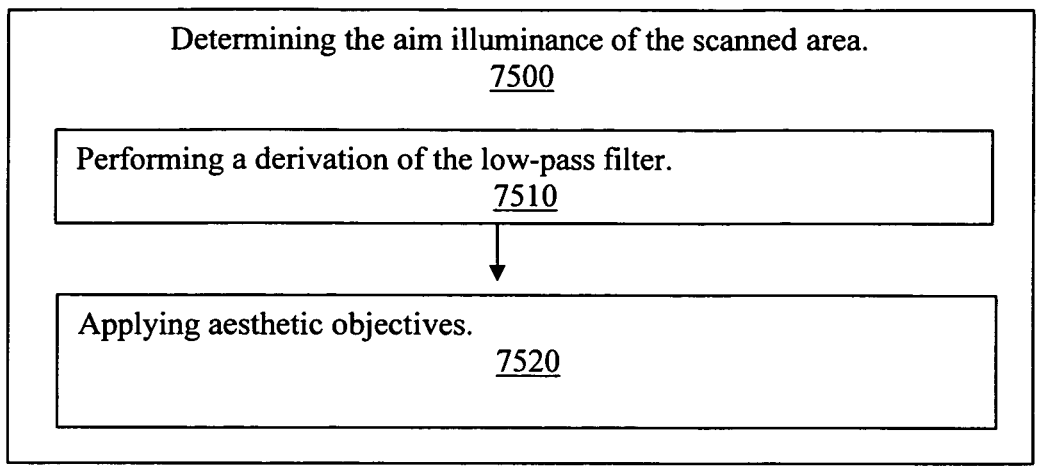
FIG. 35 is a flow chart showing a process for determining the aim illumination of the scanned area.

FIG. 35 shows steps in a process for accomplishing step 7500 of FIG. 33.

Step 7510 of FIG. 35—Perform a derivation of the low-pass filter.

Step 7520 of FIG. 35—Apply aesthetic objectives.

Enhancing a Leg

Undesirable and Desirable Characteristics in a 2-D Leg

Figure 18:
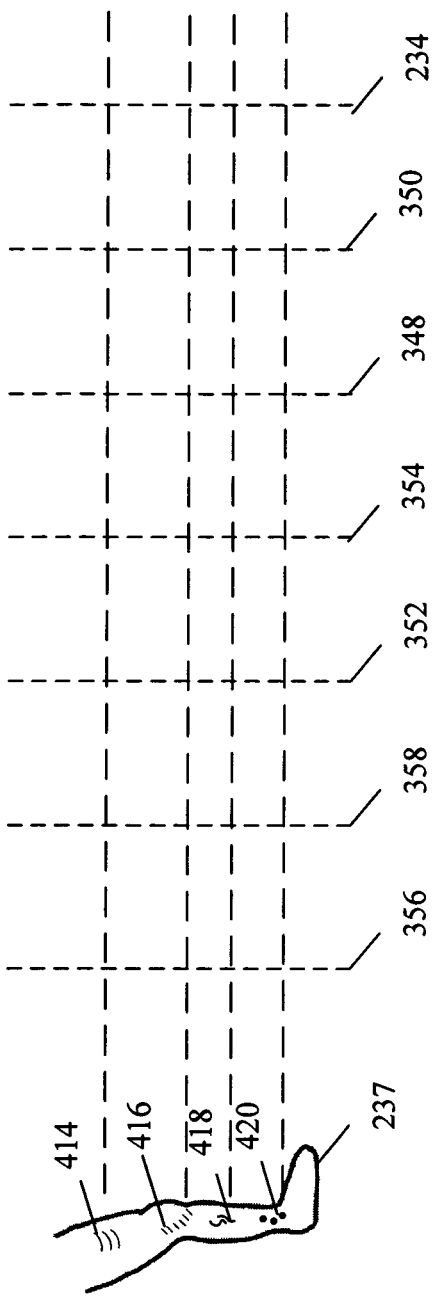
FIG. 18 is a diagram that illustrates characteristics of a 3-D human leg, with the corresponding reflectance per spectral base on a 2-D map, and a printable enhancement image.

FIG. 18 shows an illustration of a human leg 237 with the following undesirable and desirable characteristics:

Cellulite 414,

Natural color differences 416,

Varicose veins 418, and

Age spots 420.

The spectral bands for these characteristics are also shown, including one for a printable enhancement image 234 that may be used to print enhancements onto the leg 237. To simplify the illustration, a 2-D skin map is portrayed as a 1-D graph following the dotted line across the surface of the skin.

The actual depth along this line is graphed. In addition, one obtains an aim depth. The aim depth can be the low spatial frequencies only of the actual depth. However, aesthetics often dictate additional sculpting, as is known in cosmetology.

Both actual and aim depths are translated into surface angle, as the first derivative, or slope, of depth. The surface angle is then translated into illuminance of the surface, as is well understood in 3-D modeling in applications such as gaming or animation graphics. Typically the assumed illumination angle and diffusion is mean light reaching the human skin.

Printing on the skin has negligible effect on surface depth. However, the visual illusion of depth is obtained by printing the shadowing. Cellulite is not actually perceived stereoptically at more distance than approximately six inches. The human eye perceives cellulite primarily by shadowing.

Note how tanning produces pigmentation in opposition to mean illumination reaching the skin, and thus is in opposition to mean shading, thus making a sun-tanned human body appear smoother and more attractive. Note that rub-on tanning solutions do not have this characteristic of being sensitive to skin angle relative to light, and thus fail to provide the same attractiveness.

The leg example also illustrates pigmentations and varicose veins. An aim reflectance may be derived algorithmically again simply as the low-pass version of the actual reflectance; however, aesthetic attributes may be added, such as freckles, which may align with existing pigmentations, while excluding age spots. It may also include other selected features, such as knee cap darkening.

It should be understood that the aim and actual reflectance curves can represent each color separately. For example, varicose veins may be blue or red, while pigmentation may be orange. Thus each color is independently corrected using colored inks, such as the process colors cyan, magenta, and yellow.

The perceived light visualized from the leg by a human observer is the illuminance*reflectance (albedo). It is actually actual illuminance*actual reflectance, but is desired to be aim illuminance*aim reflectance. Thus to go from actual to aim, a multiplying (or dye) image should be deposited on the skin, that is translated aim angle*aim reflectance translated actual angle actual reflectance where "translated aim angle" is the aim angle translated to a standard illumination assuming mean illumination; and "translated actual angle" is the actual angle translated to a standard illumination assuming mean illumination. This provides the aim correctance, shown as the printable enhancement image 234. A separate aim correctance can be derived for each color, typically red, green, and blue to print, in order, cyan, magenta, and yellow.

A problem arises that with dyes it is only generally practical to darken the skin. (In other embodiments, it is possible to use limited amounts of whitening dyes or bleaching agents to selectively lighten areas.) Thus, as an expedient the aim paint is shifted (dotted line) so that more of the skin is correctable. This is equivalent to choosing a lower aim reflectance, for a more tanned appearance.

Some details, such as blue varicose veins on a leg, may still be outside the correction range even with the reasonable offset. These details can be corrected by depositing small areas of light pigment, than printing over with dyes to provide the right color. Alternately the extreme points can be left uncorrected. The relative error of uncorrected points is still much less noticeable if the adjoining skin is darkened somewhat.

Figure 19:
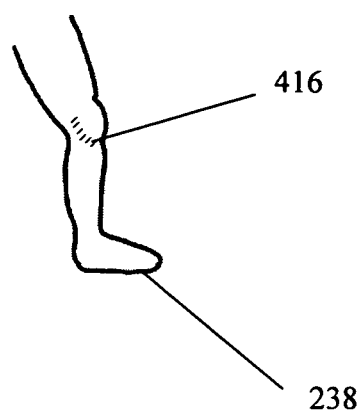
FIG. 19 is a diagram of a 3-D human leg that has been enhanced through printing of RMAs according to a printable enhancement image.

FIG. 19 shows an illustration of a human leg 238 after being enhanced through the present invention. The following undesirable characteristics, which were shown in FIG. 18, have been reduced from view:

Cellulite 414,

Varicose veins 418, and

Age spots 420.

However, the desirable natural color differences 416, which serve to make the 3-D quality of the knee cap visible, have been retained.

Enhancing a Breast

Figure 20:
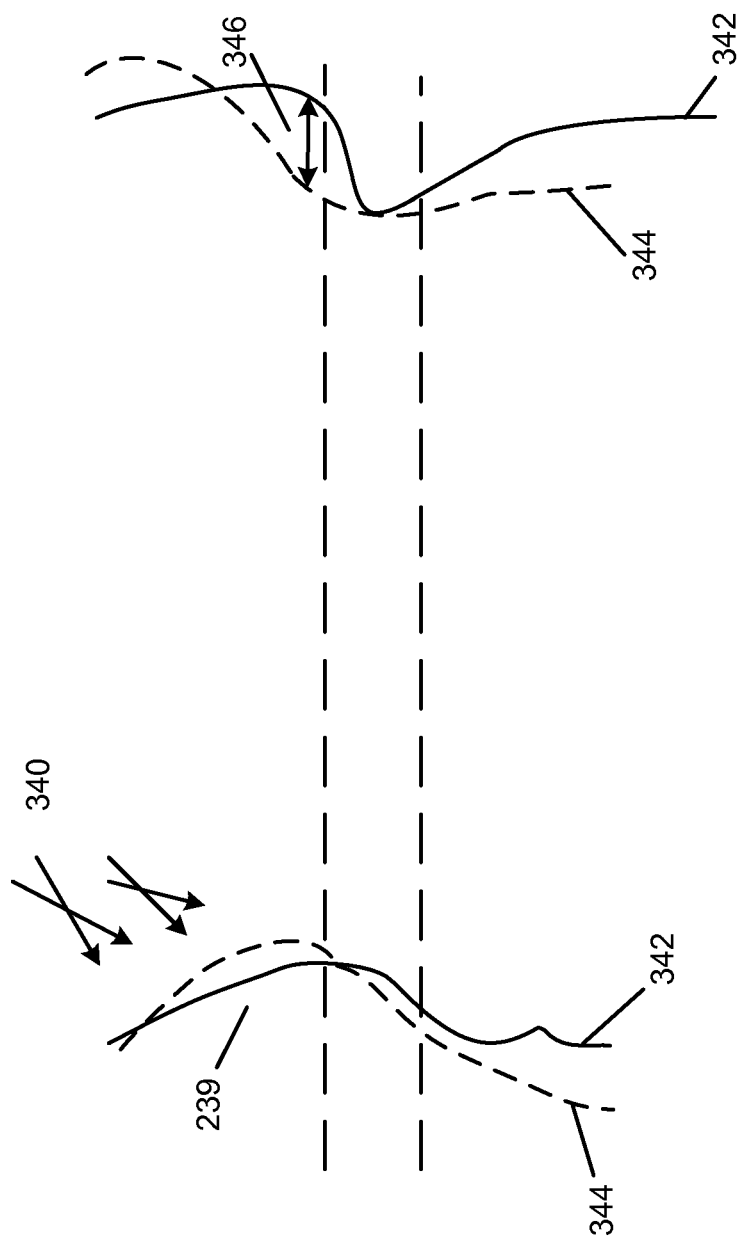
FIG. 20 is a diagram that illustrates characteristics of a 3-D human breast, with the corresponding reflectance per spectral base on a 2-D map.

FIG. 20 shows an example for changing the perception of a breast 239 from an actual 3D surface 342 under mean illumination 340 to an aesthetic aim 344 by determining the difference 346. Applying RMAs to approximate this difference will alter the perceived appearance of the breast.

Single Pass Smoothing Example

FIG. 37 represents a simple smoothing example for skin. An area of skin, such as one on the arm, is broken into a plurality of frexels at step 900. At step 910, at least one optical attribute of the frexels is determined. The optical attribute is represented as $R_i$. There is a look up table which provides a quantity of a reflectance modifying agent to apply for each range of visual characteristic. At step 930, the quantity of RMA to be applied is determined from this look up table. The desired quantity of RMA is applied at step 940, thereby changing the appearance of the area of skin. This single pass example does not require a mapping of the skin.

Multiple Pass Smoothing Example

FIG. 38 represents a multiple pass smoothing of skin. In this figure, the desired reflectance $R_d$ is approached with a series of applications of a reflective modifying agent. The actual initial reflectance is determined at step 900 as $R_a$, and that value provides a first quantity of RMA to be applied in a first pass which is $Q_1$. The application of that first amount of RMA, $Q_i$, changes the reflectance from $R_a$ to $R_i$. At the second pass $R_i$ is used in the look up table to determine the second amount of RMA ($Q_2$) to be applied. When that second amount is applied, the reflectance is changed to $R_2$. On the third pass, $R_2$ is used to determine a third amount of RMA. ($Q_3$) The resulting reflectance $R_3$ approaches the desired reflectance. The number of passes is not limited to three but may be more or less than that number.

Facial Map Example

FIG. 39 represents a facial map example. In this example, the skin on a face is allocated into a plurality of frexels as before. The optical attribute is measured in step 910 as before, except that the frexel location is determined and specified and recorded so that there is location data for individual frexels. The data for individual frexels includes sensor location, the location of the frexel and one or more optical attributes. The optical attributes maybe used to determine the reflectance, position, and orientation of the frexel at step 920. Each frexel then has an initial characteristic such as an actual reflectance. The frexel also has a desired final characteristic, such as the desired reflectance, and an amount of RMA to be applied in one or more passes. The amount of RMA is determined at step 940. The desired reflectance is determined from an enhancement strategy such as smoothing of the skin, filtering to remove middle frequency characteristics, feature recognition and feature enhancement, and general artistic schemes. The desired quantity of RMA is determined from the difference between the desired reflectance and the actual reflectance.

LED Arrangement

FIG. 40A is a schematic for sensor and LED arrangement. In this example a sensor is located along the axes of four LEDs which are designated as north, south, east, and west.

FIG. 40B is a cross section showing that the LEDs are typically directed to a point on the skin below the sensor. Typically the LEDs and sensors are provided in a housing, and the housing may have reflective properties to provide more diffuse or indirect light to the frexel in some applications. In other applications it is desirable to orientate the light directly at the frexel in order to determine the tilt of the frexel.

Depth maybe determined by shadow parallax grid projected by LEDs from different angles. In another embodiment, two cameras maybe used in a stereoscopy approach.

Feature Recognition

FIG. 41 shows a simple feature recognition approach. A frexel map for a particular frexel "m" and its neighboring frexels is represented. Data for each frexel typically includes the time, position, reflectance and orientation of the frexel. Information can be represented graphically as demonstrated in the reflectance feature portion of the diagram. At step 910, the skin is scanned to measure an optical attribute. At step 920, a visual characteristic such as reflectance is determined from the scan. At step 921, a facial map is generated to provide the actual visual characteristics as perceived by a viewer. At step 922, the frexel data is reviewed to identify local features and the parameters for the particular subject. An example of parameters is the range of readings in that subject, which can be used in normalization or other data manipulation. At step 924, enhancement strategies are applied. At step 925, an enhancement map is provided. The enhancement map includes the amount of RMA to apply to a particular frexel in order to change its visual characteristics.

FIG. 42 illustrates a frexel map for a portion of a face. This figure shows characteristics such as a pimple, frexel, light spot and a scar. Each of those characteristics is shown in an enlarged position with multiple frexels in the diagram. These areas can be represented and detected mathematically from the known properties of the various skin features, so that feature recognition can be preformed automatically with mathematical analyses.

Artistic Strategy

FIG. 43 represents an example of simple artistic strategy. When a frexel map of a face is generated, various shading strategies or overall global strategies for appearance can be provided.

Detailed Description of Embodiment—Systems

Operating Environment for Cosmetics

FIG. 1 shows an embodiment of the present invention used to apply RMAs 264 to an area of skin 302. A party sets up an application system 200 comprising the following elements, which are explained in more detail below:
- a computing environment 100—for example a personal computer, server, or portable computing device;
- a scanner 220—which electronically scans data about attributes of an area of skin 302; and
- a means of application 240—for example a printer—which can be used to apply RMAs 264, such as ink.

The computing environment 200 further comprises
- an application algorithm 230;
- storage 250—which may be may be non-volatile data storage;
- an application map 232—which is created by application algorithm 230 to provide instructions for applications onto an area of skin 302;
- a printable enhancement image 234—which is the set of instructions for applications onto an area of skin 302.

Loosely Coupled Systems

In embodiments, the elements of application system 200 may comprise discrete units and be connected through links 142 and 144, which may comprise internal connections. For example, FIG. 2 shows an embodiment of loosely connected elements for applications onto an area of skin 302. A scanner 220, printer 241, and computing environment 100 communicate over a network 130 and links 142, 144, and 146. The network 130 may comprise the Internet, a private LAN (Local Area Network), a wireless network, a TCP/IP (Transmission Control Protocol/Internet Protocol) network, or other communications system, and may comprise multiple elements such as gateways, routers, and switches. The links 142, 144, and 146 are compatible with the technology used for network 130.

A features library 274 may be used to store the characteristics of human features, for example the eye, nose, and mouth, for use by pattern recognition. The features library 274 may also be used to store idealized pattern for human features that may be used to make actual features appear more attractive. For example, an idealized pattern for human lips may be used to make actual lips appear fuller as well as redder. For the application map 232 shown in FIG. 1, a 2-D surface map 233, shown in FIG. 2, is used The 2-D surface map typically includes a representation of depth in order to capture the shape of the face.

In addition, registration means 270, mechanical or electronic, are used for tracking the location of the scanner 220 and printer 241 relative to the area of skin 302

Combined Scanner and Printer Connected with Computer

FIG. 3 shows an embodiment where an application device 246 comprises a scanner 220 and an inkjet printer 242 to apply RMAs 264 from a reservoir 262 to the area of skin 302. The application device 246 also communicates over a network 130.

Reflectance Modifying Agents

Figure 4:
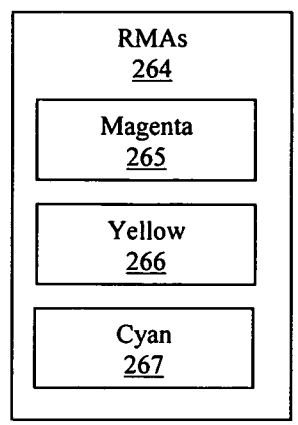
FIG. 4 is a block diagram showing the use of magenta, yellow, and cyan RMAs.

FIG. 4 shows that in an embodiment, the RMAs 264 may comprise magenta 265, yellow 266 and cyan 267 RMAs. In other embodiments, the RMAs 264 may additionally include black or brown and white.

Application Device

The application device 246 comprises the portable scanner 220 and a portable inkjet printer 242, shown in FIG. 3. In this example, the device has a height-determination means such as a tip or cup to hold the device at uniform a height of ⅛ to 1 inch (3.2 to 6.4 mm) from skin. The elevation of the probe only has to be accurate within a few millimeters. The device uses mirrors or two cameras. It typically makes ten passes to cover the 150 square inches (1000 square cm) of a face, and the time required to complete the process is comparable to that required for electric shaving. The device is under 2 inches (50 mm) in length.

Portable Scanner

In an embodiment, the portable scanner 220 comprises an area array that lightly touches the surface of the area of skin 302 to be scanned. In another embodiment the portable scanner is moved without touching skin in the vicinity of the skin being scanned. During scanning, a white LED light source in the sensor flashes to apply normal light, defined as light from above, to the area of skin 302. Measurements are taken when the LED is on and off, and the difference between the two measurements is subtracted to determine the contribution of the light source.

Inkjet Printer

In an embodiment, the inkjet printer 242 comprises an inkjet printer with 0.001 inch resolution and a reservoir 262 capable of holding RMAs 264. In an embodiment the RMAs 264 comprise transparent dyes, while in other embodiments they comprise inks or other useful chemicals. In one embodiment, FDA-approved RMAs are employed. As shown in FIG. 4, the RMAs 264 may comprise agents for the following colors: magenta 265, yellow 266, and cyan 267. They may comprise additional colors, such as black, brown, and white, as well. These colors can enable the inkjet printer 242 to create any color on the area of human skin.

Registration Means

As mentioned above, registration means 270, mechanical or electronic, are used for tracking the location of the scanner 220 and printer 241 relative to the area of skin 302. In an embodiment, the registration means 270 may comprise accelerometers, which measure acceleration and tilt, and gimbals, which measure the rotation of an object in three dimensions and control that rotation, may also be included in the application device 246. These devices help control movement and positioning and maintain the correct reflective angle for the application device 246.

In another embodiment, registration means may comprise a global positioning-like service (GPS) used locally through high frequency radiation.

In still another embodiment, registration means may comprise a set of small flat-ended pins that are pressed lightly against the surface of the skin to make an impression. For example the pins may be pressed against a face to make a mask of the face. The movement of the pins in a frame may be tracked mechanically to provide the 3-D coordinates.

Portable Application Device

Figure 5:
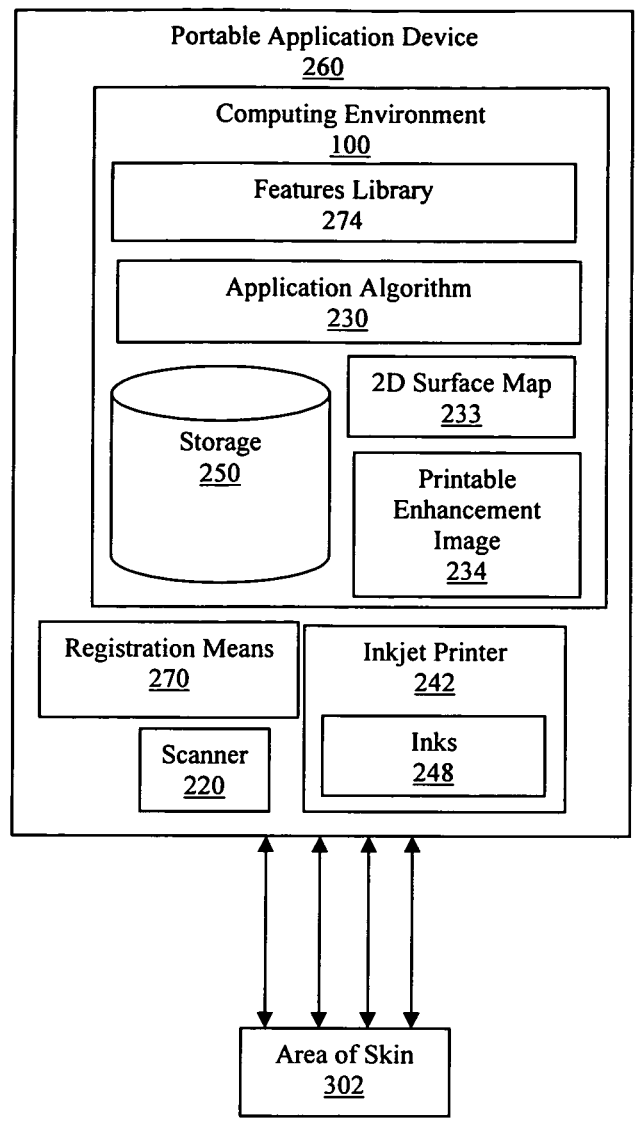
FIG. 5 is a block diagram showing an operating environment in which embodiments of the present invention may be employed through a self-contained portable application device for applying inks onto skin.

As shown in FIG. 5, another embodiment of the present invention is a portable application device 260 comprising multiple elements for applying material onto skin, which does not require an external network. An embodiment of the portable application device 260 uses an inkjet printer 242 to apply ink 248 to the area of skin 302.

Portable Application Device with Curved Surface

Figure 30:
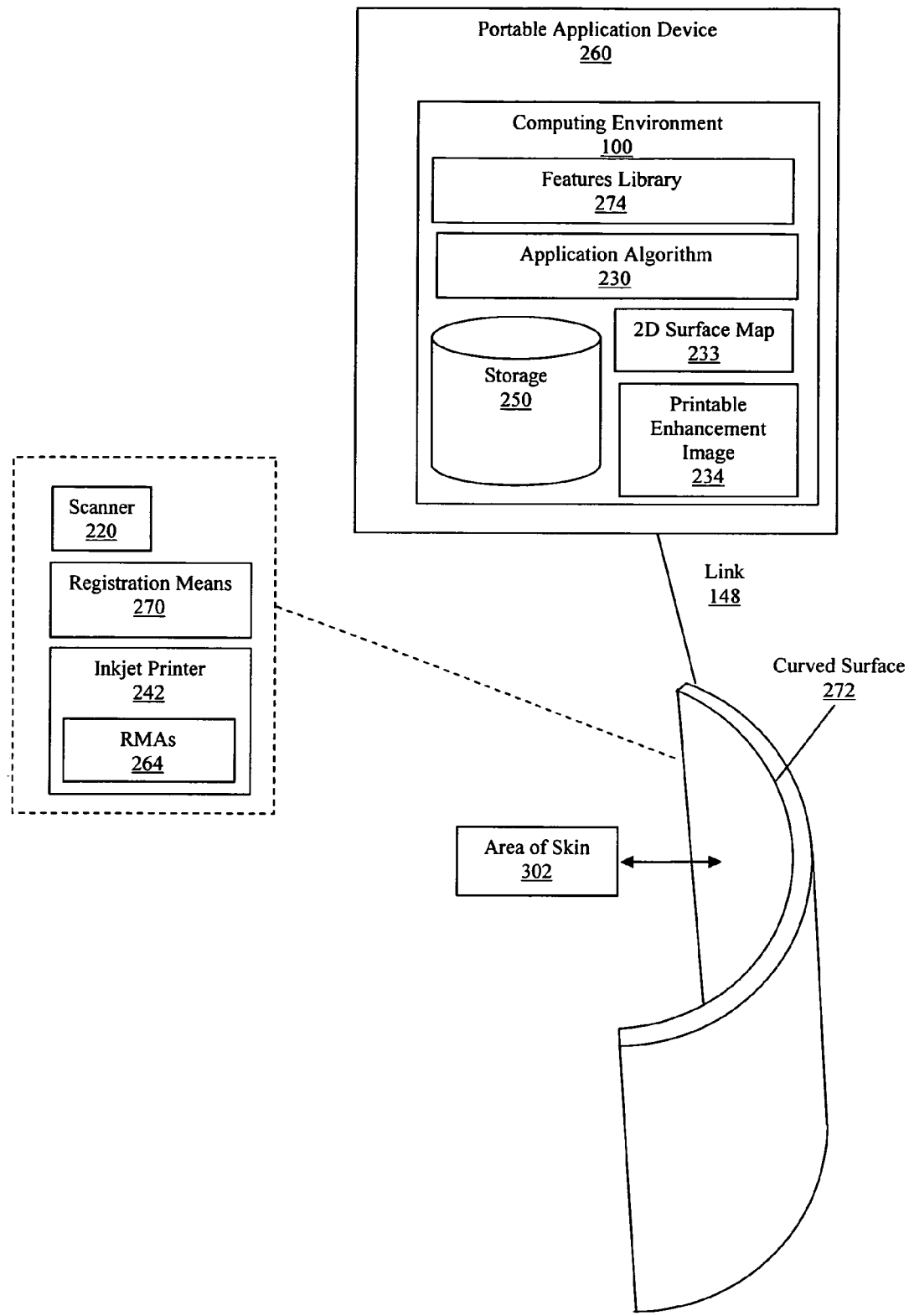
FIG. 30 is a block diagram showing an operating environment in which embodiments of the present invention may be employed for applying RMAs onto skin through communications over a network and a portable application device with a curved surface.

One aspect of the current invention is to acquire and manipulate image data of human skin. In one embodiment, a first step is used to generate a map of a portion of the body, and that map is used to generate a specific plan of selectively applying dyes at a later time. One embodiment of the current invention is to use a portable scanning device to acquire data for generating the map; and to use the portable scanning device in combination with a portable printing device to selectively apply dyes to a region of skin. FIG. 30 shows an embodiment of the present invention that may be employed for applying material onto skin, through communications over a network and a portable application device with a curved surface.

Mask or Helmet

The curved surface may comprise, for example, a mask or helmet into which a human face may be inserted and an application device (scanner/printer) that circles the face. Use of such a curve surface requires feature recognition through artificial intelligence and mapping, so that the application device can calculate its location on the face and its distance from the skin.

One advantage of the curved surface device is that is requires no user action or training. Another is that the application device remains above the skin and so does not touch the wet RMAs.

Booth

Another embodiment of the current invention is to use a booth or work station to scan a region of skin, such as a face or an entire body.

Figure 27:
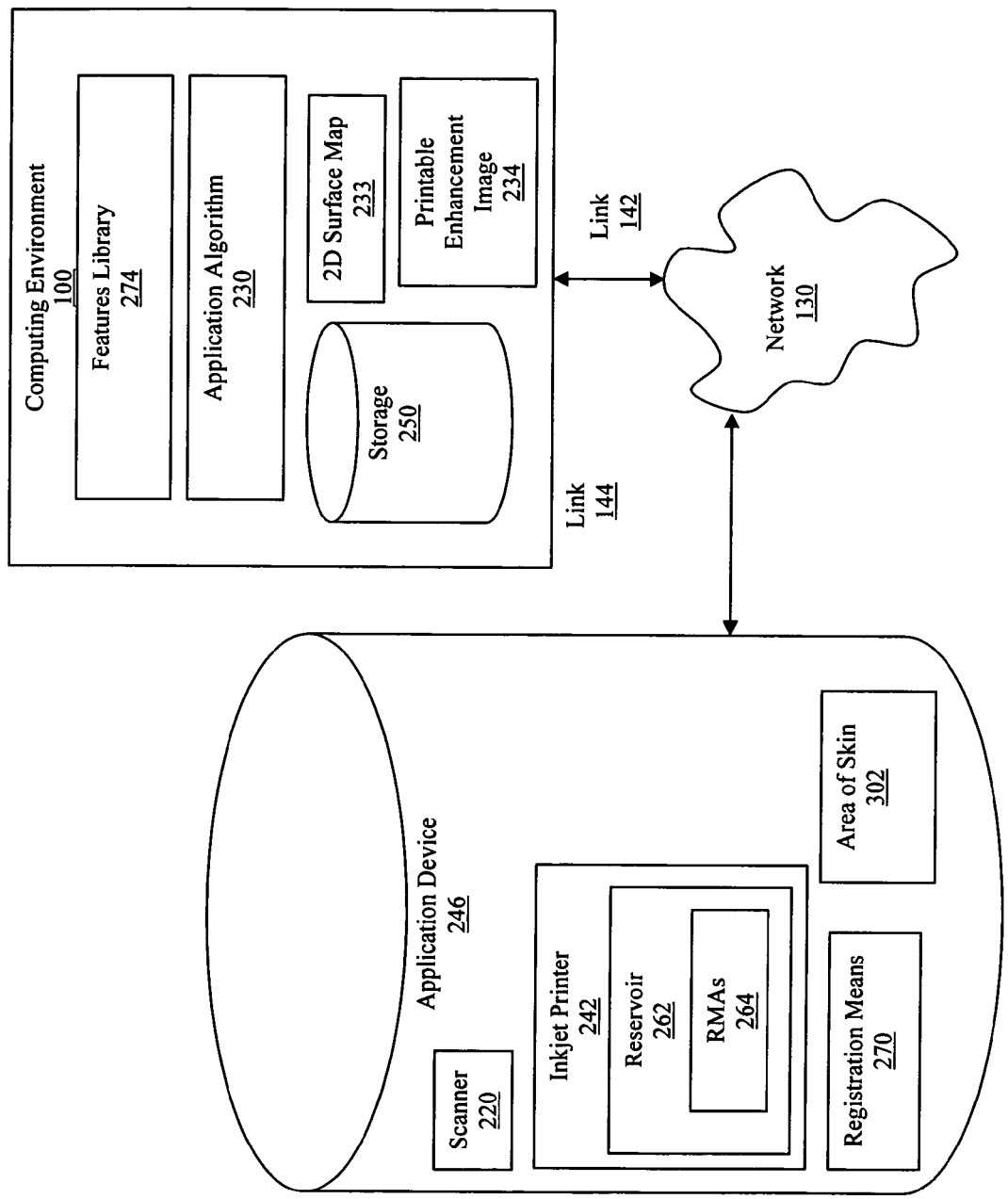
FIG. 27 is a block diagram showing an operating environment in which embodiments of the present invention may be employed for applying RMAs onto skin through communications over a network and an application device comprising a booth.
Figure 36:
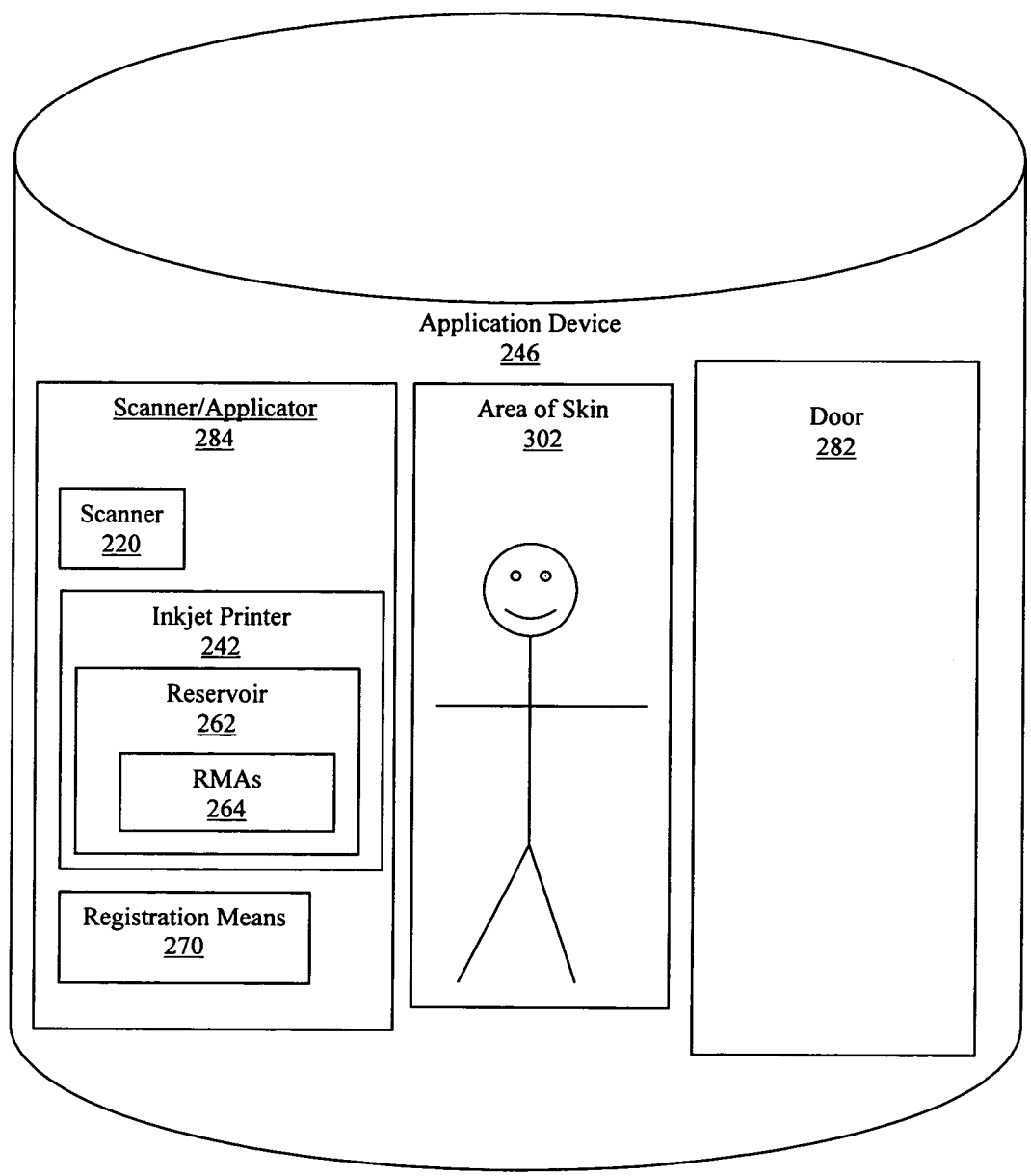
FIG. 36 is a block diagram showing an application device comprising a booth.

FIG. 27 shows an embodiment of an application device 246 comprising a booth. In this case, as shown in FIG. 36, the area of skin 302 comprises an entire person who steps into the application device 246 through a door 282. The person might undress, step into the booth, as is typically done with tanning booths, and lie or stand for the application of RMAs. A scanner/applicator 284, comprising a scanner 220, inkjet printer 242 with a reservoir 262 and RMAs 264, and registration means 270, would move across the person's body to collect data, analyze the data, and make enhancements by applying RMAs.

In another embodiment, the booth may comprise a two-part cylinder that closes over all a person or over part of a person such as a face.

Blotter

Figure 29:
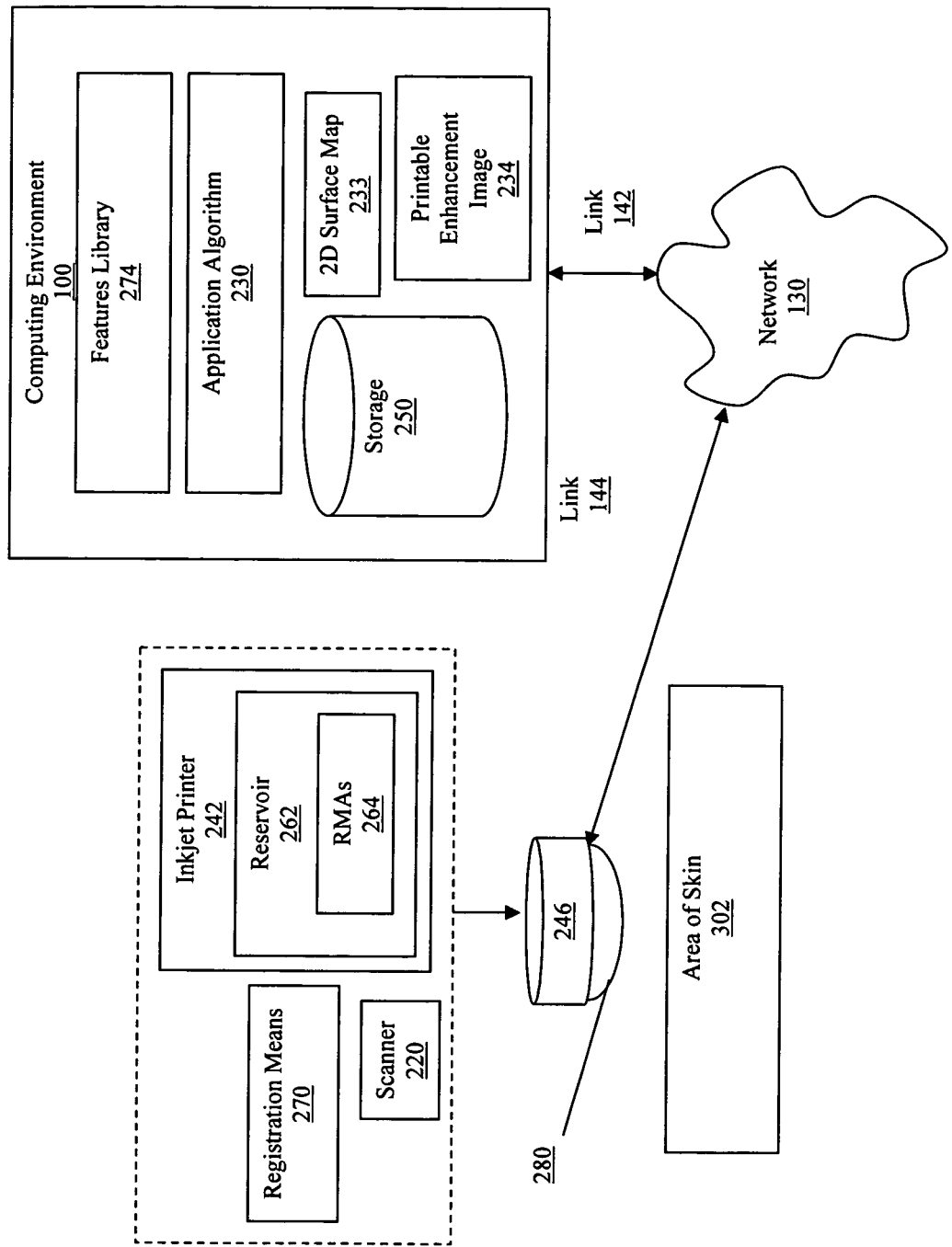
FIG. 29 is a block diagram showing an operating environment in which embodiments of the present invention may be employed for applying RMAs onto skin through communications over a network and a blotter application device.

FIG. 29 shows an embodiment with an application device 246 comprising a blotter. The blotter comprises a cup 280 to maintain an approximate appropriated distance from the area of skin 302, as explained above. Instead of moving the blotter application device 246 in a single pass or multiple passes over the enter area of skin 302, the user places the blotter application device 246 over a small area of skin and holds it there briefly, to accomplish scanning, analysis, an application of RMAs in that small area, and then moves the blotter application device 246 to the next small area.

Figure 44:
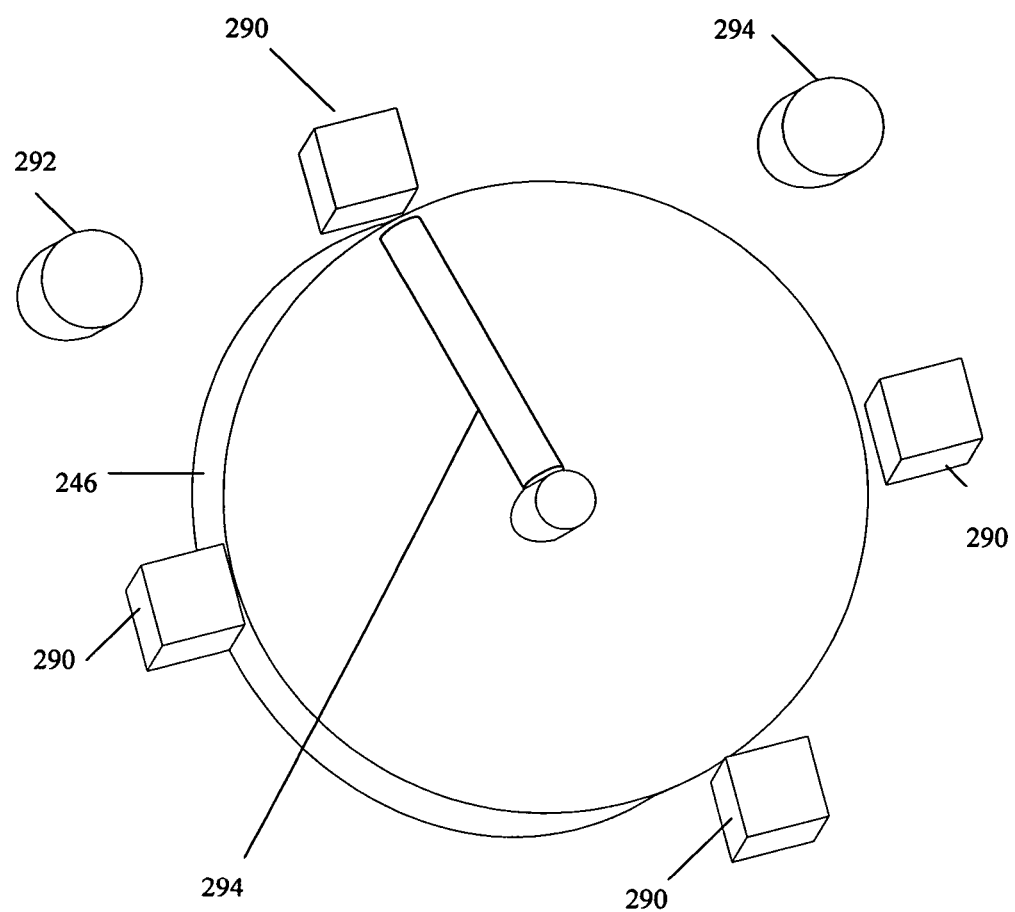
FIG. 44 is an example of a rotating printer for a blotter application device.

For the blotter application device 246, mechanical means would move the printer 242 over the area of skin 302 for the application of the RMAs 264. For example, FIG. 44 shows an inverted view of an application device 246 comprising a blotter. In an embodiment, the blotter application device 246 comprises four LEDs 290, two cameras 292, and a rotating inkjet printer 294 that moves about a central axis on the application device 246 like the hand of a clock. The rotating inkjet printer 294 prints RMAs throughout the area of the blotter application device 246 except for the area of the central axis, which can be printed on by moving the blotter to an overlapping area for a second printing.

Light Sources

FIGS. 40A-B are sample layouts for LEDs and a sensors for acquiring reflectance and skin orientation data.

In one embodiment, a set of four light sources is used, such that the light sources are placed at the corners of a diamond, where the sensor is positioned at the center of the diamond layout. This configuration simplifies the mathematical analysis for calculating surface profile.

In an embodiment, it is useful to employ mean illumination. For this, multiple diffuse or orthogonal light sources may be used, in a configuration which may include mirrors. The lights may be flashed repeated, as strobe lights, so that hundreds of images may be taken of a small area can averaged for effectiveness.

Process for Employing an Application System for Cosmetics

Figure 6:
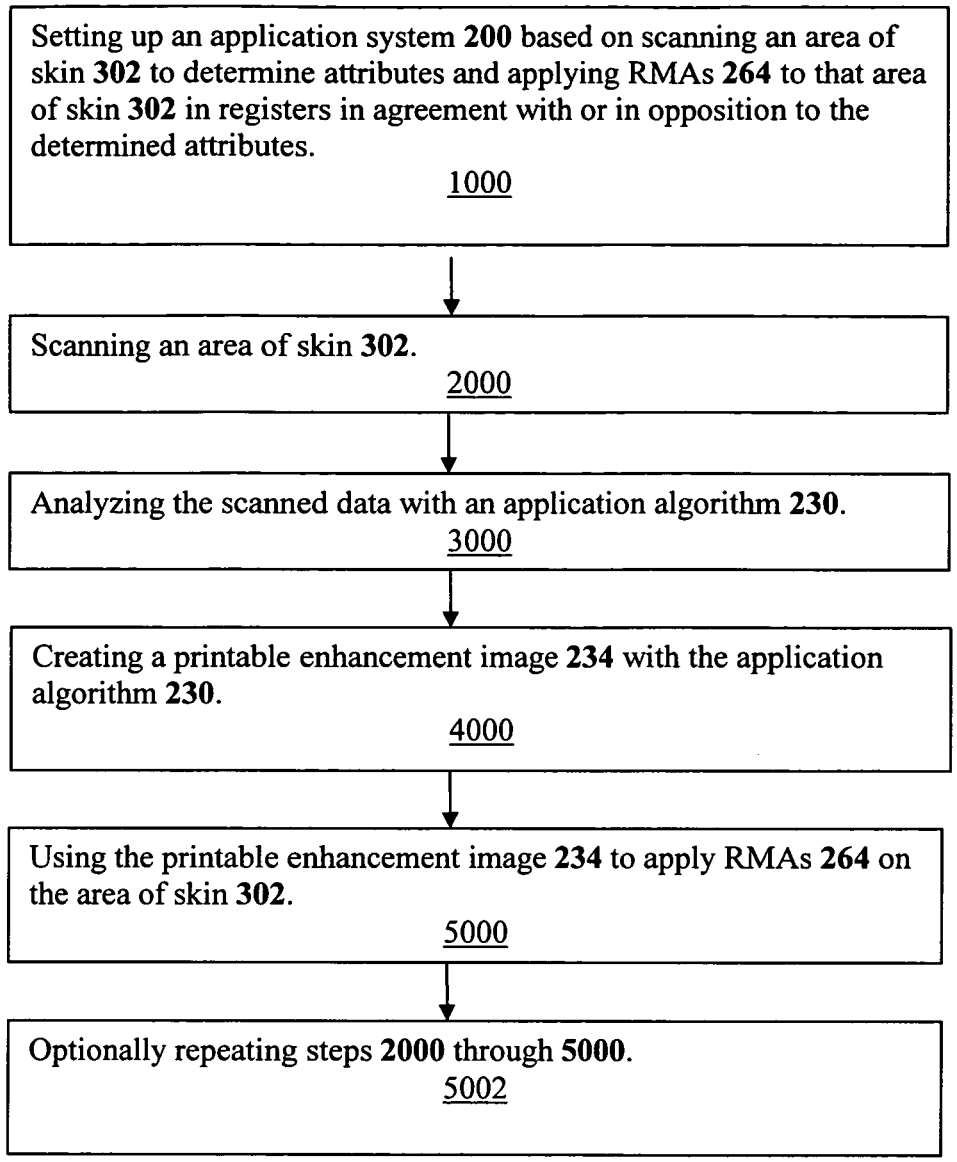
FIG. 6 is a flow chart that illustrates a process for employing an application system.

FIG. 6 shows a process for employing an application system 200, in an embodiment. This process comprises the following high-level steps, which will be explained in detail below:

Step 1000 in FIG. 6—Setting up an application system 200 based on scanning an area of skin 302 to determine attributes and applying RMAs 264 to that area of skin 302 in registers in agreement with or in opposition to the determined attributes;

Step 2000 in FIG. 6—Scanning an area of skin 302;

Step 3000 in FIG. 6—Analyzing the scanned data with an application algorithm 230;

Step 4000 in FIG. 6—Creating a printable enhancement image 234 with the application algorithm 230;

Step 5000 in FIG. 6—Using the printable enhancement image 234 to apply RMAs 264 on the area of skin 302; and Step 5002 in FIG. 6—Optionally repeating steps 2000 through 5000.

Setting Up an Application System

FIG. 7 shows a process for Step 1000—setting up an application system 200, shown in FIG. 6, in an embodiment. The process comprises the following steps, which will be explained below:

Step 1010 in FIG. 7—Providing an application algorithm 230;

Step 1020 in FIG. 7—Providing the application algorithm 230 on a computing environment 100;

Step 1030 in FIG. 7—Providing storage 250 on the computing environment;

Step 1040 in FIG. 7—Integrating a means of scanning 220 an area of skin 302; and Step 1050 in FIG. 7—Integrating a means of application 240 of RMAs 264.

Providing an Application Algorithm

One or more programmers create an application algorithm 230 that, in an embodiment, controls the elements and processes of the present invention outlined in FIG. 6 and explained above. After the application algorithm 230 has been created, it can be used on at least one computing environment 100, as shown in FIG. 1, and may be integrated with other elements of application system 200. For example, in an embodiment application algorithm 230 may be loaded on a computing environment 100 comprising a server. The computing environment 100 may be equipped with non-volatile storage 250 capable of storing data such as scanned data from scanner 220.

In various embodiments, the application algorithm can include default strategies which may be based on feature recognition, a feature-based lookup scheme, or general artistic objectives.

Figure 8:
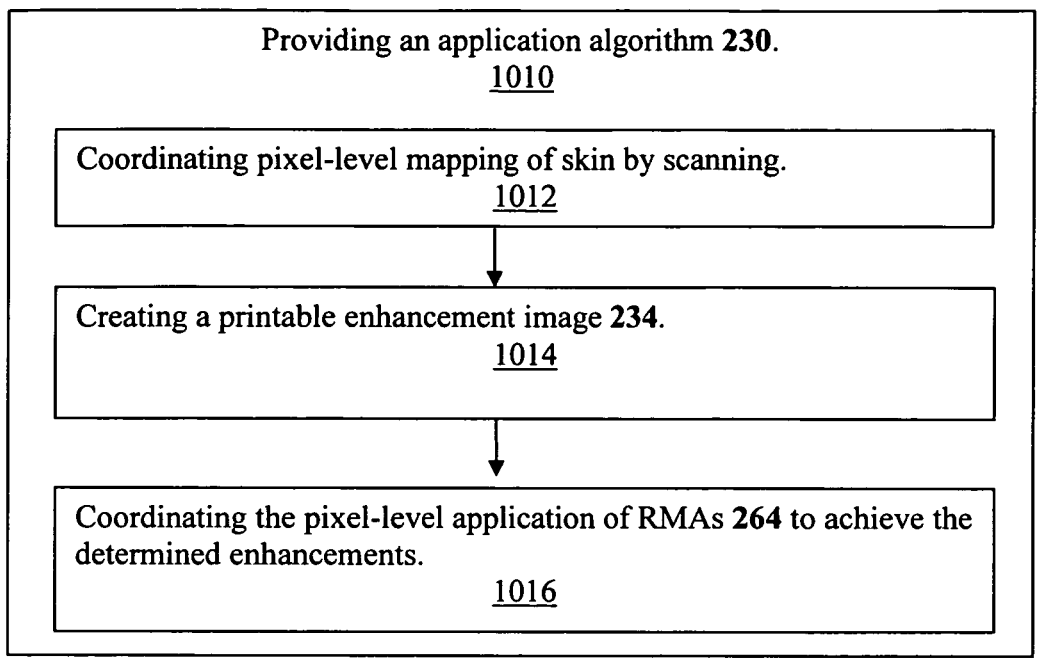
FIG. 8 is a flow chart that illustrates a process for the programming in an application algorithm in an embodiment for printing on skin.

As shown in FIG. 8, in an embodiment the general functions to be accomplished by the application algorithm 230 are
- Coordinating Pixel-Level Mapping of Skin by Scanning;
- providing feature recognition, or accepting manual selection of image enhancement strategies
- Creating a printable enhancement image 234; and
- Coordinating the pixel-level application of substances to achieve the determined enhancements.

Coordinating Pixel-Level Mapping of Skin by Scanning

A primary function of the application algorithm 230 is to analyze scanned data about an area of a first instance of material 300 and create a 3-D application map 232 of the attributes of that area 300 for which application of a second instance of material 300 would be useful. A key part of this function is that the application algorithm 230 determines at each scanned point whether the application of the second instance of material should be in a register in agreement with the attributes of that area of the first instance of material or in a register in opposition to those attributes. This decision is based on instructions in the algorithm for what would be useful and advantageous for the area of the first instance of material 300.

Figure 31:
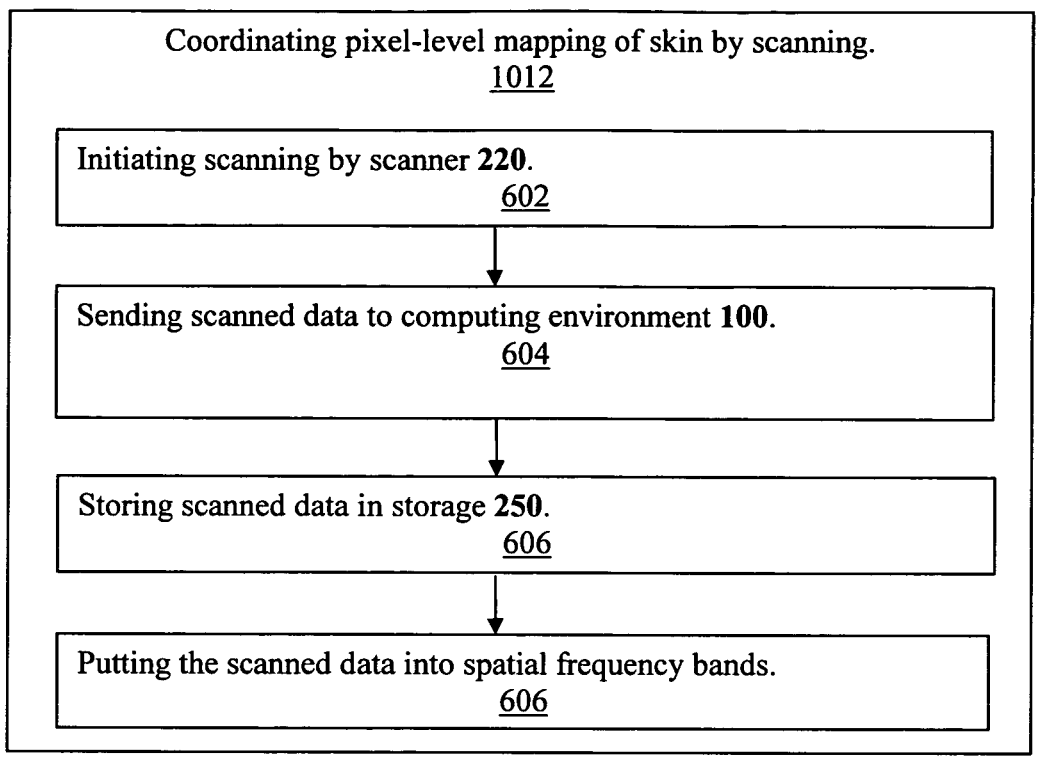
FIG. 31 is a flow chart for coordinating pixel-level mapping of skin.

FIG. 31 shows the steps involved in coordinating scanning:
- Step 602 in FIG. 31—Initiating scanning by scanner 220.
  - When the application device 246 is turned on and moved over an area of skin 302, the scanner 220 begins scanning.
- Step 604 in FIG. 31—Sending scanned data to computing environment 100.
  - The application device 246 transmits its scanned data over link 144, network 130, and link 142 to computing environment 100.
- Step 606 in FIG. 31—Storing scanned data in storage 250.
- Step 608 in FIG. 31—Putting the scanned data into spatial frequency bands.

Creating a Printable Enhancement Image

The goal of a cosmetics embodiment of the present invention is to understand and make use of the characteristics of the human visual system to make the observer perceive a person as younger than that person is. This may be considered a form of camouflage performed at the pixel level. It is important to note that the techniques of the present invention for accomplishing this goal do not wipe out all the detail in the area of skin affected, but retain significant, desirable details that make the area of skin look real. To accomplish this goal, the present invention uses sophisticated techniques, explained below, to create a printable enhancement image 234 for making appropriate applications of the RMAs 264.

Figure 9:
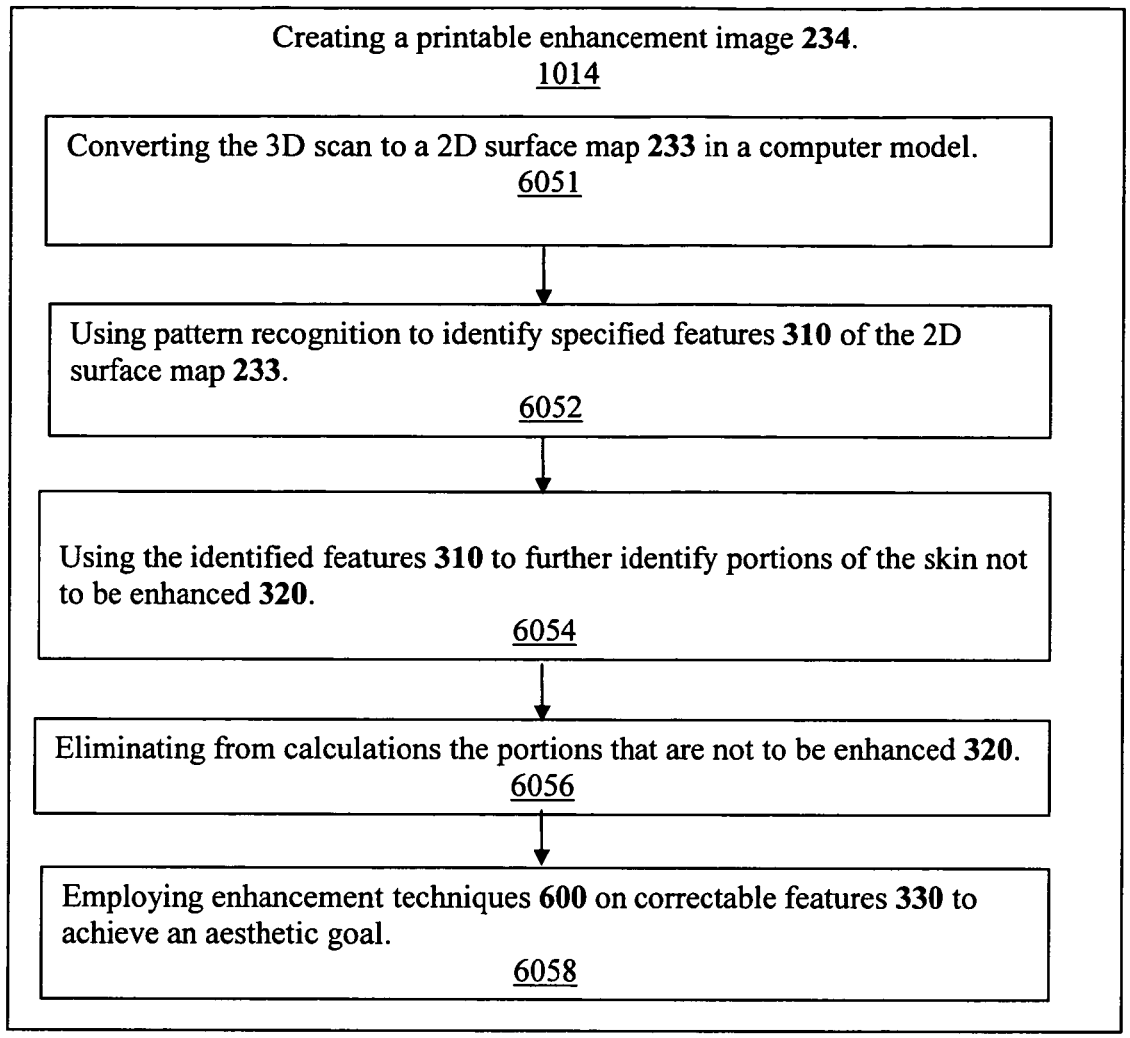
FIG. 9 is a flow chart that illustrates a process for creating a printable enhancement image.

FIG. 9 shows a process for creating a printable enhancement image 234, in an embodiment.

Step 6051 in FIG. 9—Converting the 3-D scan to a 2-D surface map 233 in a computer model.

Figure 10:
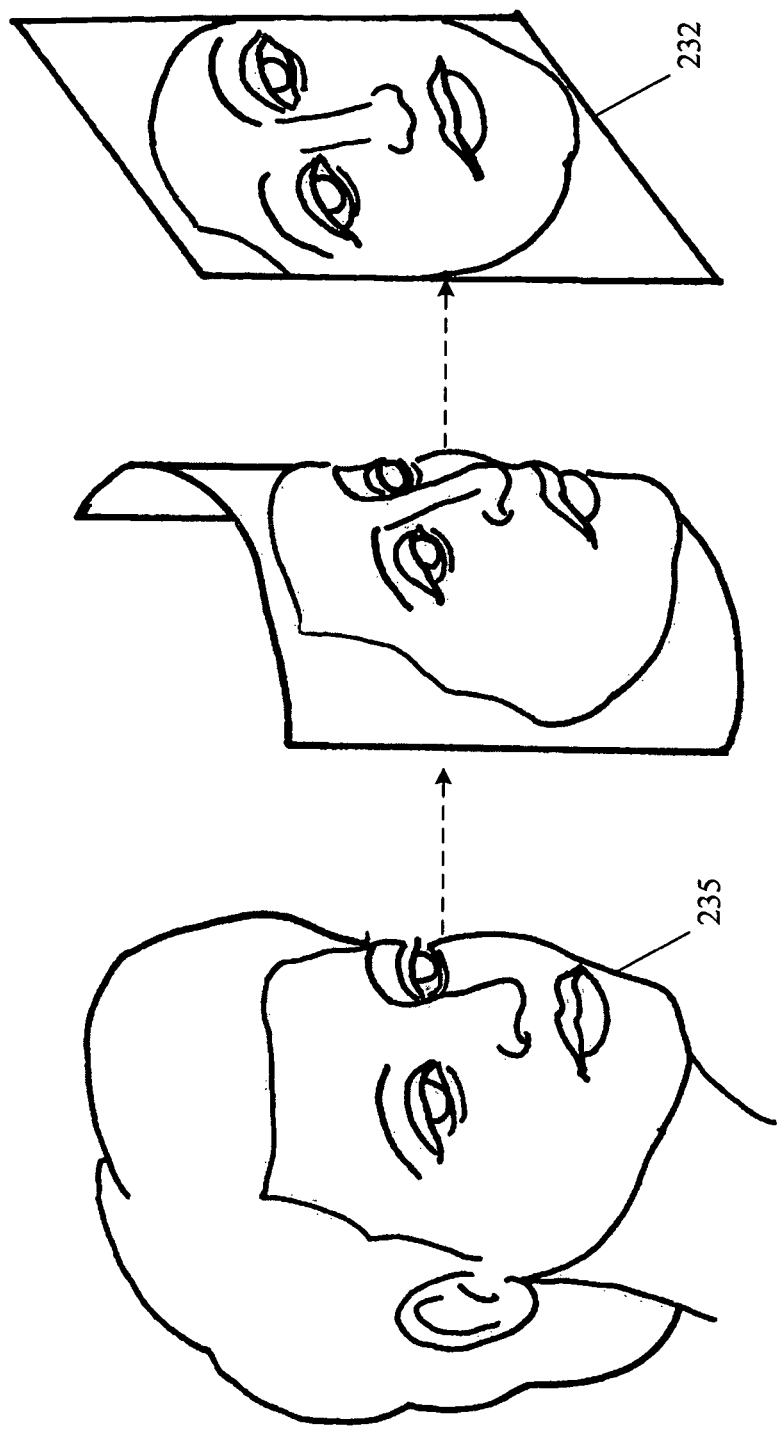
FIG. 10 is a diagram that illustrates how a 3-D object maps to a 2-D surface in a computer model.

FIG. 10 shows an example of how a 3-D human face 235 may be mapped to a 2-D surface map of that face 233, through well known techniques employs in computer modeling and gaming. For this 2-D mapping, in the small (limit) all surfaces are flat, creating a razor model for the "base."

Step 6052 in FIG. 9—Using pattern recognition to identify specified features 310 of the 2-D surface map 233.

For example, pattern recognition may be used to identify the eyes.

Step 6054 in FIG. 9—Using the identified features 310 to further identify portions of the skin not to be enhanced 320.

For example, it may be desirable to specify that the eyes not be enhanced with potentially irritating RMAs.

Step 6056 in FIG. 9—Eliminate from calculations the portions that are not to be enhanced. For example, the eyes may be eliminated from calculations.

Step 6058 in FIG. 9—Employing enhancement techniques 600 on correctable features 330 to achieve an aesthetic goal.

The enhancement techniques employed by the present invention are explained in detail below.

Figure 32:
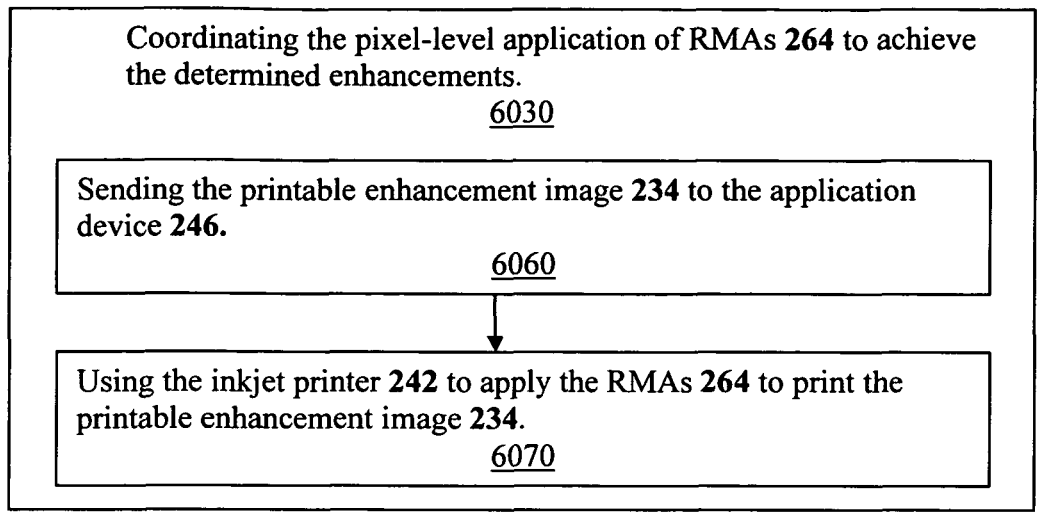
FIG. 32 flow chart for coordinating a pixel-level application of RMAs.

Coordinating the Pixel-Level Application of Reflectance Modifying Agents to Achieve the Determined Enhancements As shown in FIG. 32, coordinating the pixel-level application of RMAs 264 to achieve the determined enhancements may be achieved through the following steps:
- Step 6060 in FIG. 32—Sending the printable enhancement image 234 to the application device 246.
- Step 6070 in FIG. 32—Using the inkjet printer 242 to apply the RMAs 264 to print the printable enhancement image 234.

Operation of an Embodiment

The operation of the present invention can be illustrated with reference to the application device 246 and computing environment 100 shown in FIG. 3.

Scanning

The user moves the application device 246 across the area of skin 302 so that the scanner 220 can record data. For example, the area of skin 302 might be the user's face. The scanner 220 sends the scanned data over the network 130 to the computing environment 100 where the data is stored in storage 250.

In an embodiment, the user may be asked to employ a tapping or blotting motion of the probe, rather and making smooth passes as in moving an electric shaver over the face. This motion reduces smudging in the application of RMAs.

In an embodiment the user may be asked assume a neutral, motionless position, to present a neutral model. For example, for use with the face, a user may be asked to hold still, close the eyes, and have an expressionless face. For use with the entire body, the user may be asked to stand still in a specified position in a booth.

Analyzing the Scanned Data

The application algorithm 230 puts the stored data into spatial frequency bands and uses pattern recognition to analyze them to determine the landscape of the area of skin 302 and the dimensions that require application of the RMAs 264.

The application algorithm 230 uses its analysis to create in software a 2-D surface map 233 of the area of skin 302, which is stored in storage 250, for potential future use.

Creating a Printable Enhancement Image

The application algorithm 230 also creates a printable enhancement image 234 based on a 2-D surface map 233.

Note that alternately the printable enhancement image 234 can be made manually by an operator who displays the map on a computer screen and uses controls to make desired adjustments.

Printing the Enhancement

The application algorithm 230 sends the printable enhancement image 234 over the network 130 to the application device 246 that triggers the inkjet printer 242 to apply the RMAs 264 from the reservoir 262 to area of skin 302. The inkjet printer 242 applies different quantities and mixes of the RMAs 264 to create desired results in different portions of the area of skin 302, at the pixel level, making the application very precise.

In various embodiments, the scanning and printing components can be provided in hand-held, fixtured, or booth systems.

Example of Hand-Held Operation

In a hand-held system, the device may be the size of an electric shaver or powder puff so that it may be blotted or moved across the skin. The device may be used in a single pass mode to provide a general smoothing of skin appearance, or in a multiple pass mode where several passes over each area of the skin are used in order to provide a relatively small correction on each pass. The system may include a feedback means such as a tone to indicate that the operation is complete.

Example of Hand-held Scanner that Touches Skin

FIG. 26 shows a handheld scanner. In this example, the scanner housing touches the skin so that the application device, such as a printer head, is maintained at an approximate known distance and orientation with respect to the skin.

Example of Helmet Guide for Facial Modeling and Printing

A helmet mode is an example of a fixtured system where the scanning and application device has designated limited travel paths. The fixtured system may include coordinate reference points, guide strips, and a movable probe.

Application Example—Facial Makeup

For example, a user could move the application device 246 over his or her face and have RMAs 264 applied as a form of makeup to enhance the attractiveness of the face. These RMAs may comprise transparent dyes, or inks, or pigments that would even up the skin tone while retaining desirable details like beauty moles, add reddish color to cheeks, and hide flaws and scars in the skin, greatly enhancing the attractiveness of the skin to the human eye. Typically, in an embodiment the user would close his or her eyes and mouth to prevent exposure of them to the RMAs 264. In another embodiment the system would use feature identification to recognize sensitive areas such as eyes and restrict itself from applying RMAs 264 to those sensitive areas.

Touchups

Once a 2-D surface map 233 and a printable enhancement image 234 for that face has been stored, they can be used repeatedly to quickly apply the RMAs 264 to the face with the application device 246, for example for quick daily cosmetic touchups.

Note that the printable enhancement image 234 may be both in a register in agreement with the attributes of areas of the face or in a register in opposition to those attributes. For example, a light area of skin may be left relatively light or may be darkened, depending on the desired effect calculated by the application algorithm 230.

Camouflaging a Bump through Simulated Tanning

Figure 12:
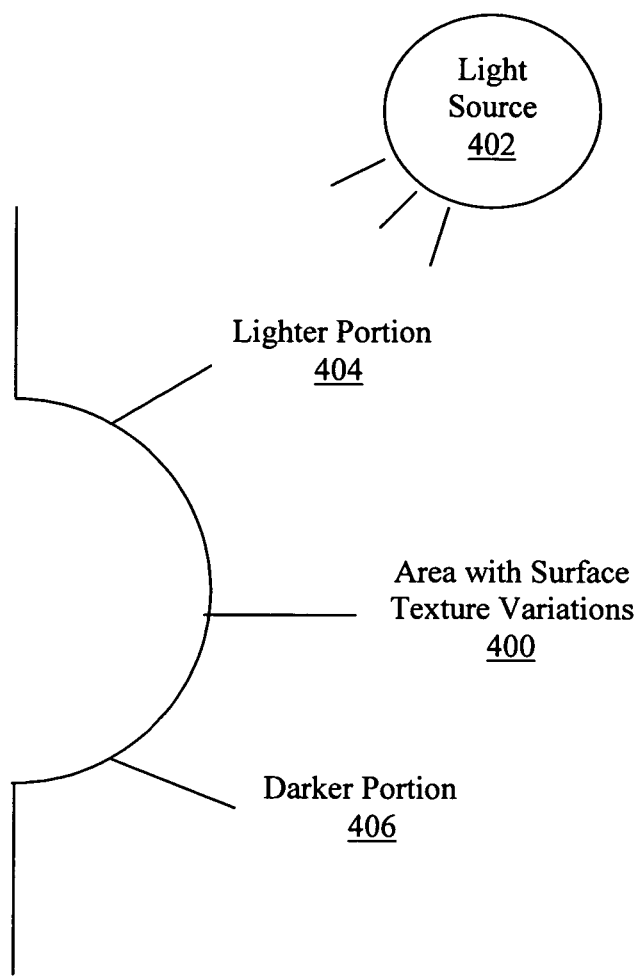
FIG. 12 is a block diagram that illustrates lighting from above on an area with surface texture variations.

The present invention can identify a very small area with surface texture variations 400, shown in FIG. 12, representing a tiny bump, for example. It can apply an ink or dye to the apparently lighter portion 404 of the bump 400, apparently lighter because it is receiving more illumination by virtue of the surface angle relative to the light source, and not darken the shaded, apparently darker portion 406 underneath the bump. This reduces the light and dark contrast associated with the dimensionality of the bump, making the skin look smoother.

Detailed Description of Embodiment—Handheld Mark Applicator

Figure 47:
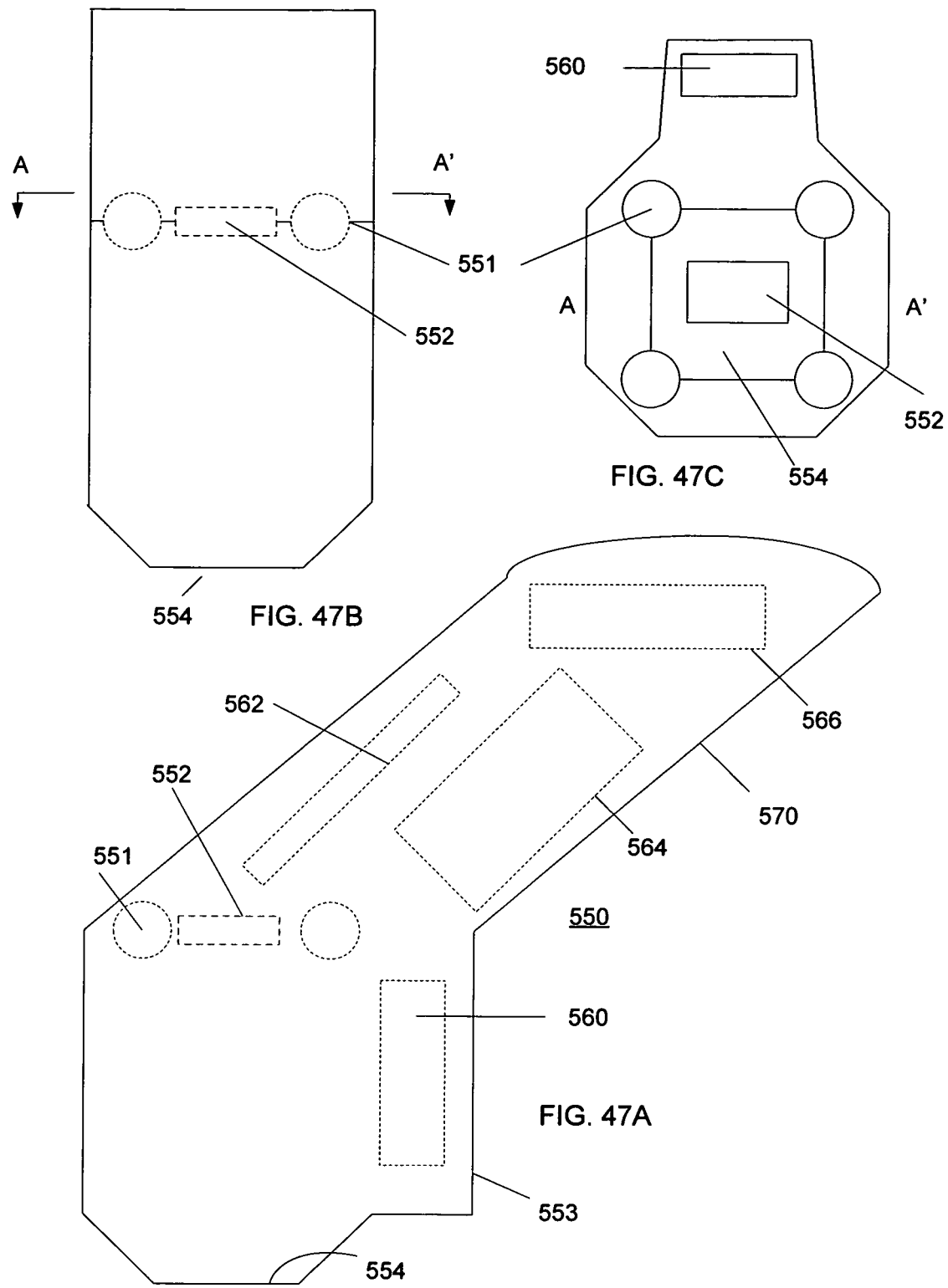
FIG. 47A is a side view of one embodiment of a handheld device for skin marks.
FIG. 47B is a front view of the device of FIG. 47A.
FIG. 47C is a top cross sectional view along section AA' of FIG. 47B.

FIG. 47A is a side view of one embodiment of a handheld device for skin marks such as age spots, small scars, and varicose vein. FIG. 47B is a front view of the device of FIG. 47A, and FIG. 47C is a top cross sectional view along section AA' of FIG. 47B.

The mark applicator device 550 includes a housing 553 which provides an upper handle portion and a lower skin application portion. In this example, the device is about 1½ by 2 inches (38-50 mm) wide and about 4-5 inches (100-127 mm) tall. In this example, an opening in bottom 554 of the housing is about ½ to ¾ inch square (12.7-19.2 mm square).

At least one light source is used. In this example, four light sources 551 are positioned in proximity to the 4 corners of a square tube. The light sources are typically white light LEDs, or combinations of LEDs such as red, green, and blue to produce a white light, but the sources may also be of varying wavelengths to provide additional data for mark recognition. In some cases, a single light source may be used. The advantages of using separate wavelength light sources include greater sensitivity, better color accuracy, and higher resolution. In the booth and movable handheld embodiments described above, however, these advantages may not overcome the practical difficulties and time required to sequence four different lighting conditions for each set of frexels. Most cameras are able to provide good color images from a white light source.

In the current embodiment, however, the camera is not moved, and it is more practical to obtain an image from each of several colors of light sources, and from the white light produced when all of the light sources are on. Thus some examples of this applicator include light sources of different wavelengths, thus providing a better white light and additional image data at a plurality of wavelengths in order to support more sophisticated feature recognition.

In general, the light source or sources in this and other embodiments may be of a variety of wavelengths including visible light, infrared, and ultraviolet. The infrared wavelengths provide a better penetration of the skin to support feature recognition.

The lower portion of the tube preferably has a reflective surface such as a shiny or brushed aluminum or steel so that the light sources reflect from the housing walls and provide a uniform lighting to the exposed skin area. These reflective surfaces are analogous to an optical fiber. A camera 552 captures images of the exposed area as described below. A print head 560 is moved across the opening in order to print a desired correction to the area, and to the mark in particular. Other components in the housing include a circuit board 562 and electronics; at least one RMA cartridge 564 and a battery 566. The term RMA is used here in the general sense and the cartridge or cartridges may contain pigments or other agents.

In operation, at step 7900 the device is placed over an area of skin which has a mark which the user desires to camouflage. The device is held in place for a predetermined period of time, or until the unit signals completion, such as with a status light or audible tone. The user then presses a switch on the housing (not shown) and the unit performs the following typical operations:

In response to the user pressing a switch on the housing at step 7910, the unit completes the following steps.

At step 7920, the camera captures a first image at ambient light with the camera of the area of skin exposed by the bottom opening. Even when the unit is pressed against the skin, some light travels through the skin and partially illuminates the area.

At step 7930, the light sources are turned on.

At step 7940, the camera captures a second image with the camera while the light sources are on.

At step 7950, the unit analyzes the images, which may include the following steps. Subtracting the first image from the second image at step 7952; identifying the mark at step 7954; and determining a desired modified reflectance for the mark and adjacent skin at step 7956.

At step 7960, determining a desired amount of RMA to print on the mark to achieve the desired modification. A generally opaque and white RMA would typically be used to camouflage the small marks of this embodiment. The substance would be similar to a classical makeup base, but typically lighter or more white that the base. In one example, the RMA is a pure white, or is white in one wavelength, such as a light pink. The RMA is preferably lighter than the skin so that small amounts may be used over a mark in a manner than matches surrounding skin.

At step 7970, printing the correction in one or more print head passes. One example print method includes printing a portion of the desired correction in a first pass at step 7972; taking an image of the area of skin after printing the first portion at step 7974; analyzing the image at step 7976; adjusting the amount to be printed in the second pass according to the analysis of the image at step 7978; and printing at least a portion of the remaining correction amounts in a second pass at step 7979. Additional passes may be performed if desired. A "pass" in this example refers to the print head being moved over the skin area. All other components and the housing remain stationary. The second pass provides an opportunity to compare the predicted correction to the actual correction, and to compensate for the difference. For instance if less correction is printed than desired, the unit may print more than the remaining calculated amount in a second pass; and if more correction is printed than desired, then the unit may print less than the remaining calculated amount in a second pass.

Detailed Description of Embodiment—Specialized Skin Region Applicator

In this embodiment, a unit is provided to print a specialized area of the skin such as lips, or around the eyes. The unit may be provided as a booth-type fixture, but is preferably portable, such as a handheld device. The device may include a portable support such as a chinrest to provide stability and alignment.

In an example embodiment for lips and surrounding skin areas, a device similar to the handheld mark applicator of the embodiment described above may be used. The unit typically has several differences to the mark applicator. In this example, the unit is typically larger than the mark applicator, and the opening, may be of a shape such as an ellipse which more closely matches the skin region. Since the skin region may have substantial curvature, the print head typically has a z-axis capability to be moved closer to the skin or further from the skin as the head is moved over the region.

The multiple light sources as described in the above embodiment are effective for providing a "shading" analysis of frexel orientation over small areas. Since a region like the lips has larger shape features as well as local features, it is desirable to supplement the shading analysis with stereoscopy methods. For instance the use of two camera permits a comparison of the images to develop a stereoscopic analysis of the region, as well as a local shading analysis. The two approaches are thus complimentary.

In this example, the device is placed over the lips; or in the case of a booth device, the lips are placed in the booth. Images are taken by a pair of cameras with multiple lights sources under various lighting conditions. The image data from one or both cameras can be used to determine frexel orientation as described above. The image data from both cameras can also be used to develop a stereoscopic analysis.

The analysis is used to develop a correction plan. The correction plan is executed by moving the print head over the region to apply one or more RMA—preferably in multiple passes. In this example, the print head has a z-axis control so that the head may be brought closer to the lips or further from the lips as necessary.

Alternate Embodiments
Other Hardware and Software

It will also be apparent to those skilled in the art that different embodiments of the present invention may employ a wide range of possible hardware and of software techniques. For example the communication between a Web service provider and client business computers could take place through any number of links, including wired, wireless, infrared, or radio ones, and through other communication networks beside those cited, including any not yet in existence.

Also, the term computer is used here in its broadest sense to include personal computers, laptops, telephones with computer capabilities, personal data assistants (PDAs) and servers, and it should be recognized that it could include multiple servers, with storage and software functions divided among the servers. A wide array of operating systems, compatible e-mail services, Web browsers and other communications systems can be used to transmit messages among client applications and Web services.

Detailed Description of Embodiment—Determining Reflectance and Topology of Skin Areas for Medical Monitoring In this embodiment, the devices and techniques for image acquisition and analysis which were described above for the cosmetic examples are provided to provide one or more image for medical analysis. These techniques, include providing multiple light sources to permit fine shading analysis to evaluate fine detail of skin morphology; providing two or more camera to permit stereoscopic analysis of a region of skin, providing both shading and stereoscopic analysis; developing a map of a region of skin, comparing a map or feature to a library to assist in the analysis; and comparing maps acquired at different times to determine and record changes over time.

These techniques may be provided in various housings including, but not limited to, a full body booth; a partial booth for a region of skin such as a face, arm, let, torso, or back; a handheld scanning device which is moved over the skin; or a smaller handheld device which is placed in a stationary manner over specific skin marks such as moles.

Detailed Description of Embodiment—Selectively Applying Medicinal Agents

In this embodiment, the devices and techniques for image acquisition and analysis further include at least one print head or other drop control device to apply one or more medicinal agent in response to the analysis.

These techniques may be provided in the full range of housings as described above.

Detailed Description of Embodiment—Adapting Cosmetic System to Medical Monitoring or to Selectively Apply Medicinal Agents In one embodiment, the monitoring of a region of skin is provided in the normal course of routine usage of a cosmetic device as described above.

In another embodiment, the monitoring of a region of skin is provided supplemental to the normal course of routine usage of a cosmetic device as described above.

In another embodiment, cosmetic device as described above is adapted to deliver one or more medicinal agent in one or more passes over a skin region, and in one or more treatment sessions. One or more additional application heads and reservoirs may be provided for the medicinal agents.

This patent application employs for medical monitoring and the optional application of medicines and other compounds beneficial to health the system and method explained by the patent application cross referenced above.

In accordance with the present invention, the data gathered by the cosmetics system and method of the cross-referenced application is repurposed for medical purposes. This process can provide frequent monitoring of all or portions of the external surface of the human body for the early detection and treatment of medical problems. For example, daily monitoring through the present invention to track all skin lesions in a precancerous range, so that such lesions can be treated early, might make untreatable skin cancers a thing of the past. To give another example, such daily monitoring may provide teenagers with early diagnoses of results of various behaviors, such as their getting acne from eating unhealthy foods and from improper skin care, in a manner analogous to biofeedback In addition, the system of the cross-referenced application may be used for the application of medicinal agents.

Process

Figure 48:
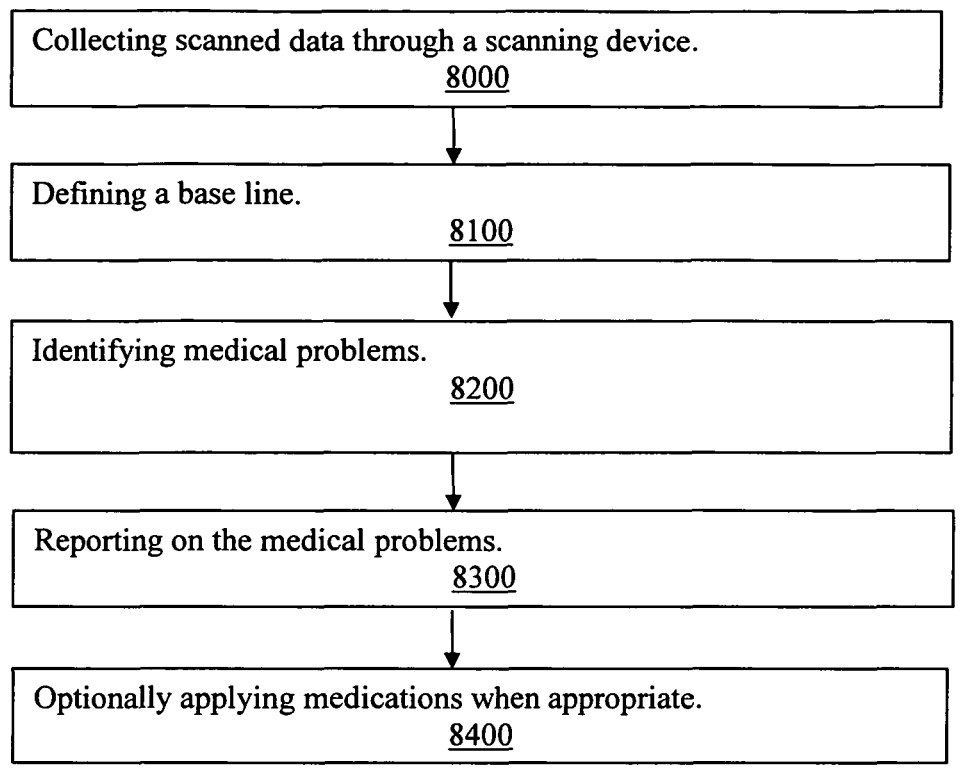
FIG. 48 is a flow chart that illustrates a process for medical monitoring and optional treatment.

In an embodiment, the present invention uses the following process, shown in FIG. 48.

Step 8000 in FIG. 48—Collecting scanned data through a scanning device;
Step 8100 in FIG. 48—Defining a base line;
Step 8200 in FIG. 48—Identifying medical problems;
Step 8300 in FIG. 48—Reporting on the medical problems; and
Step 8400 in FIG. 48—Optionally applying medications when appropriate.

Step 8000 in FIG. 48—Collecting Scanned Data through a Scanning Device

Any scanning device, known to those skilled in the art, may be used. In an embodiment, the scanning device may comprise the computer-controlled cosmetics system explained by the patent application cross referenced above, which may be a whole-body system. Whenever a person uses the cosmetics system, scanned data about all or part of the external surface of that person's body is collected and quantified. The cosmetics system puts the data into one or more spectral bands, where reflectance and surface topography data may be analyzed to identify medically relevant patterns and changes to previously identified characteristics.

Many people are highly motivated to use cosmetics daily or even multiple times a day. Because cosmetic use is much more frequent that the typical use of medical examinations, much more data can be collected about the person more frequently and more consistently than has typically been possible through prior methods.

Figure 50:
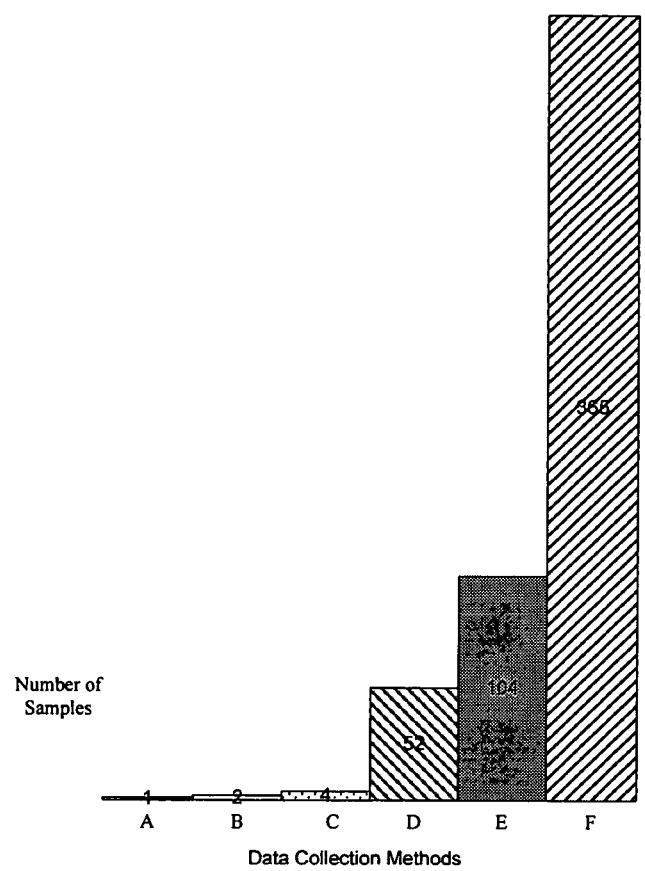
FIG. 50 is a bar graph showing the number of samples collected for medical monitoring of a person in a year by different data collection methods.

FIG. 50 is a bar graph showing the number of samples collected for medical monitoring of a person in a year by different data collection methods.

Method A represents a single yearly exam made by a general practitioner.

Method B shows exams made every six months by a medical specialist.

Method C shows exams made every three months by a specialist.

Method D represents data collected during weekly applications of makeup.

Method E shows data collected when makeup is applied twice a week.

Method F shows the much larger amount of data that can be collected when makeup is applied daily.

As FIG. 50 shows, a woman who applies makeup daily through the present invention would collect 365 times more medical information, in a much more statistically meaningful sample, than she would through a yearly medical exam. She would also collect medical data 365 times more frequently, which would greatly aid the early detection of medical problems.

More frequent monitoring may have many medical advantages. It can lead to earlier detection of medical problems. It can be used to create a better base line about various physical conditions in human beings than infrequent monitoring can, creating a history of these conditions over each person's whole lifetime. Many changes in physical conditions are normal. For example, muscles swell after exercise, and mosquito bites cause bumps on a person's skin. But a bump that keeps recurring in the same place over time may be of more concern medically.

Step 8100 in FIG. 48—Defining a Base Line

The system and method of the cross-referenced application cited above creates a 3-D model of the scanned exterior surface of all or a portion of a human body. The present invention uses feature recognition software to analyze the scanned data represented in the 3-D model and establish a medical base line of a person's physical characteristics as shown in reflectance data and surface topology data.

For example, reflectance data can show medically relevant colors of areas of skin and of other features. Light areas of skin may represent relatively healthy areas. Darker areas may represent moles and freckles. Very light areas may represent scars. Redness in cheeks may represent healthy coloring.

Surface topology data can show the relative depth of areas. For example, smooth areas of skin can be identified, as well as projections such as bumps and scars. Depressions such as pores and wrinkles can also be identified.

As a result, a base line of the scanned areas can be created and can be represented in a 3-D map showing medically relevant conditions.

Step 8200 in FIG. 48—Identifying Medical Problems

The feature recognition software can identify medical problems in several ways, as shown in FIG. 2.

Figure 49:
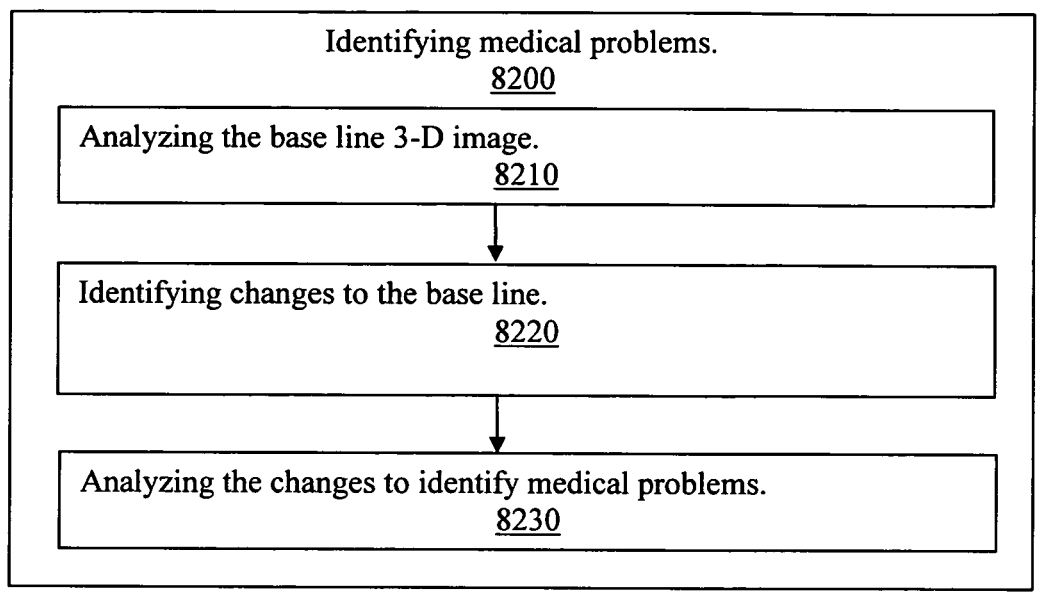
FIG. 49 is a flow chart that illustrates a process for identifying medical problems.

Step 8210 in FIG. 49—Analyzing the Base Line 3-D Image

The feature recognition software can potentially identify existing medical problems in the base line 3-D Image, such as acne, bruises, tumors, and melanoma, by their characteristic patterns of reflectance and surface topology. When medical problems are identified, the present invention reports on them, as explained below, so that the problems can be treated. For example, changes showing that an area of skin has become recessed over time may indicate structural deterioration as the result of malignant cells. If such changes are identified, they are reported. Bulges or depressions in large areas of skin may indicate cancer, atrophy, dropsy, and other more deeply positioned pathologies.

Step 8220 in FIG. 49—Identifying Changes to the Base Line

Each time additional scanned data about a person is collected through the cosmetics system, the present invention further uses feature recognition software to track changes to the medical base line, representing changes in physical characteristics. This can provide frequent phasic data about medically relevant conditions, and data as to what changes are cyclical for a particular individual.

For example, reflectance data can show medically relevant changes in the colors of areas of skin and other features. Blue areas that suddenly appear may indicate bruising. Sudden red areas may indicate acne or sunburns. Changes in the color and patterns of moles may indicate cancer. It may be medically relevant to determine whether such changes have occurred in a person previously.

With regard to surface topology data, swelling in formerly smooth areas of skin may indicate tumors, bumps may indicate bruises and new scars, and depressions in skin may indicate internal disease, for example.

Step 8230 in FIG. 49—Analyzing the Changes to Identify Medical Problems

Identified changes are further analyzed, for example through Bayesien probability equations, in comparison with a data in a software library showing the characteristics of medical problems as expressed in patterns of reflectance and of surface topology.

Examples of Unhealthy Characteristics

The following list presents a few examples of unhealthy characteristics in the external surface of the human body that the present invention identifies.

Acne

Analysis of reflectance data: Pigment changes can identify the reddish eruptions of acne, typically caused by viruses. Blackheads may be present. White pus may be discharged.

Analysis of surface topology data: Changes in morphology can identify the swelling of acne sores.

Breast Cancer

Analysis of reflectance data: Surface changes can identify rapid changes in vascularization characteristic of cancer. Thicker veins or changing vascular patterns seen through the skin are suspicious because in their early stages cancerous cells pull in blood to feed themselves. Sudden redness of the breast, especially when the redness is mottled, may be a further indication of pathological conditions, as conditioned by measurements elsewhere on the body indicating sun exposure.

Analysis of surface topology data: Thicker veins can produce swollen areas on the surface of the skin. Later, cancer can destroy surrounding tissues, so that an affected area shrinks or appears to sink. In general, lumps or thickening and changes in shape in the breast may indicate cancer Jaundice Analysis of reflectance data: A quick change in color to yellow may indicate a liver malfunction.

Melanoma

Analysis of reflectance data: The well-known ABCD patterns are indicators of melanoma:

Asymmetry—The two halves of a spot on the skin are unlike each other.

Border—The border of a spot is irregular, scalloped, or poorly defined.

Color—The color of a spot varies from one area to another. The shades of color are tan, brown, black, and sometimes white, red, or blue.

Diameter—The diameter of a spot is larger that 6 mm.

Analysis of surface topology data: Lumpiness, irregular growth changes.

Varicose Veins

Analysis of reflectance data: Reflectance changes to bluish can characterize varicose veins.

Analysis of surface topology data: Swelling and enlargement can also characterize varicose veins.

Step 8300 in FIG. 48—Reporting on the Medical Problems

The present invention identifies patterns potentially indicating medical problems, either during the creation of an initial 3-D map of medically relevant patterns or during subsequent comparison of changes to a base line 3-D map. After identifying medical problems, the present invention reports about them. The means of reporting can take different forms, known and not yet known, in different embodiments. For example, in different embodiments the means of reporting may be a printer, a computer display, or an e-mail.

Figure 51:
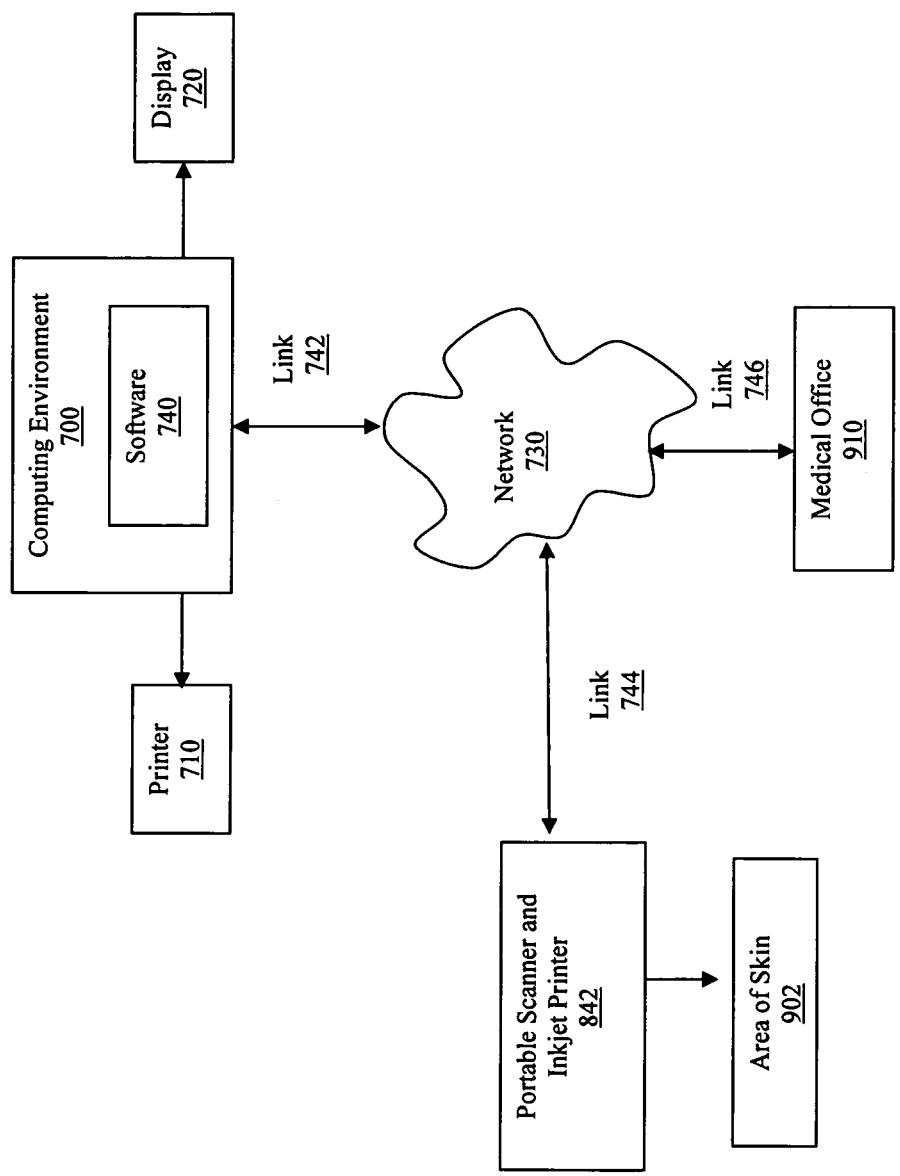
FIG. 51 is a block diagram that illustrates an operating environment for the present inventions, with reporting elements.

FIG. 51 shows an embodiment where the present invention comprises a computing environment 700 loosely connected through a network 730 to a portable scanner and inkjet printer 842 that represent an element of the cross-reference application mentioned above for scanning an area of skin 902. The computing environment 700 is directly connected to a printer 710 and a display 720 and is also connected to a medical office 910 through the network 730.

The computing environment 700 can communicate with portable scanner and inkjet printer 842 and the medical office 910 over network 730 and links 742, 744, and 746.

The network 730 may comprise the Internet, a private LAN (Local Area Network), a wireless network, a TCP/IP (Transmission Control Protocol/Internet Protocol) network, or other communications system, and may comprise multiple elements such as gateways, routers, and switches. The links 742, 744, and 746 are compatible with the technology used for network 730.

After identifying medical problems, the present invention employs software 740 on the computing environment 700 to report on those problems according to parameters in the software 730 specified by the user. For example, the user may specify that medical problems be displayed on display 720, printed on printer 710, or sent to a medical office 910 by e-mail for review.

Step 8400 in FIG. 48—Optionally Applying Medications when Appropriate

Applications of Medications

In an embodiment, the present invention may apply appropriate compounds to identified medical problems when appropriate. This can even be done without requiring the patient to take overt action. For example, an embodiment may automatically apply sun block to an area of skin that is frequently sunburned. Other embodiments may automatically apply acne medicine to acne at an early stage of the acne's development and antiseptic ointment to scratches. Still another embodiment may apply living skin cells or other replacement materials to burned areas of a patient's skin with great accuracy.

For some conditions, such as acne, medicine can be applied very precisely at the pixel level to only the areas that are affected with a disease or medical problem. This may allow stronger, more effective dosages of the medicine to be used than is typically possible through standard broadcast topical applications, as well as applications at an earlier stage of the medical condition, because of early detection. Standard acne medicines may be harmful if used in concentrated dosages over wide areas of skin. But with the present invention acne medicine may be applied specifically to the pores of acne spots in very small but concentrated dosages that are administered frequently, such as during daily makeup sessions. To cite another example, the present invention can apply a medical compound right to the pore into which a mosquito has bitten, to soothe the itching and reduce the swelling and redness.

This capability for precise application of medications allows varied application of them. For example, sun block may be applied selectively, so that an upturned surface which would receive more light or areas more often exposed to the sun and therefore age faster, such as the back of hands, can be protected more strongly. When used cosmetically, areas of skin that will be tanned can be corrected at the frexel level by the application of sun screen. For example, applying more sun screen to a pigmented area, such as damaged skin, would cause that area to be lightened relative to surrounding areas that received less sun screen. Regions burned by the sun can be avoided for aesthetic purposes similar and supplemental to the application of transparent cosmetics.

In addition, the medical compounds can themselves be used for cosmetic purposes. For example, a white-colored sun block ointment can be used to make an unattractive dark spot on skin light and thus more attractive.

System

To apply medicines and medically beneficial compounds, the present invention may use the system provided by the cross-referenced application mentioned above, in an embodiment. However, modifications may be made to that system for the medical applications of the present invention.

As shown in FIG. 52, for example, a second reservoir 870 and inkjet printer head 922 for medical compounds may be added to the reservoir 862 and printer head 920 of the cross-referenced application. Moreover, the second reservoir 870 can store multiple compounds, for example sun block 872 and acne medication 874.

The use of different reservoirs, one 862 for RMAs 864 and one 870 for medical compounds 872 and 874, can help prevent the accidental application or mixing of medical compounds or ink. The use of a second printer head 922 accomplishes the same purposes, and further allows the use of a second printer head 922 with a configuration appropriate for the application of medicinal compounds.

What is claimed is:

1. A method for monitoring a region of human skin using a handheld cosmetic application device, the method comprising:
generating, by the handheld cosmetic application device, one or more images of the region of human skin, the region of human skin allocated into a plurality of frexels, the one or more images generated at a first time;
storing the one or more images to computer memory, the computer memory also storing one or more images generated at a second time, the second time being earlier than the first time and during use of the handheld cosmetic application device for application of cosmetic compounds;
processing, by the handheld cosmetic application device, the one or more images generated at the first time to measure reflective properties of the region of human skin;
automatically determining, by the handheld cosmetic application device, an amount of one or more cosmetic compounds to apply to at least one frexel of the plurality of frexels based on the reflective properties;
automatically applying, by the handheld cosmetic application device, the amount of the one or more cosmetic compounds to the at least one frexel;
comparing, by the handheld cosmetic application device, at least one image generated at the first time to at least one image generated at the second time;
identifying, by the handheld cosmetic application device, an unhealthy characteristic of the region of human skin based on the comparing; and
reporting, by the handheld cosmetic application device, the unhealthy characteristic.

2. The method of claim 1, further comprising applying, using the handheld cosmetic application device, a curative medical compound to treat the unhealthy characteristic.

3. The method of claim 1, wherein determining an amount of one or more cosmetic compounds to apply comprises analyzing the region of human skin based on the reflective properties and a morphology.

4. The method of claim 3, wherein analyzing the region of human skin comprises defining a base line of medically relevant attributes from images, and identifying attributes that warrant preventative or curative medical attention or treatment.

5. The method of claim 4, wherein identifying attributes that warrant preventative or curative medical attention or treatment comprises:
analyzing the base line;
identifying changes in view of the base line; and
analyzing the changes to identify the attributes.

6. The method of claim 1, wherein generating the one or more images comprises:
generating a plurality of lighting conditions, each lighting condition comprising selecting an on or off state for each of a plurality of light sources;
scanning the region of skin to obtain image data while repeating the plurality of lighting conditions; and
generating the one or more images based on the image data.

7. The method of claim 6, further comprising determining a position of a frexel being scanned.

8. The method of claim 6, further comprising determining a tilt of the frexel with respect to a reference plane based on the image data.

9. The method of claim 8, further comprising determining a local skin morphology from the tilt of the frexel and tilts of other frexels in proximity to the frexel.

10. The method of claim 1, wherein comparing at least one image generated at the first time to at least one image generated at the second time comprises:
generating a first map of the region of human skin based on locations and reflectances of each of the plurality of frexels at the first time;
generating a second map of the region of human skin based on locations and reflectances of each of the plurality of frexels at the second time; and
comparing the first map to the second map.

11. The method of claim 1, wherein identifying, by the handheld cosmetic application device, an unhealthy characteristic of the region of human skin is further based on pattern recognition comprising a reflectance pattern and a surface topology of the region of human skin.

* * * * *